US008207167B2

(12) United States Patent
Greig et al.

(10) Patent No.: US 8,207,167 B2
(45) Date of Patent: Jun. 26, 2012

(54) ARYL-PHENYL-SULFONAMIDE-PHENYLENE COMPOUNDS AND THEIR USE

(75) Inventors: Iain Robert Greig, Aberdeen (GB); Rose Mary Sheridan, Northchurch (GB); Raymond Fisher, High Peak (GB); Matthew John Tozer, High Peak (GB); Juha Andrew Clase, High Peak (GB); Andrew Smith, High Peak (GB); Andrew Robert Tuffnell, High Peak (GB); Robert Jurgen Van 't Hof, Lothian (GB)

(73) Assignee: PIMCO 2664 Limited, London (GB)

( * ) Notice: Subject to any disclaimer, the term of this patent is extended or adjusted under 35 U.S.C. 154(b) by 0 days.

(21) Appl. No.: 13/063,950

(22) PCT Filed: Sep. 18, 2009

(86) PCT No.: PCT/GB2009/002223
§ 371 (c)(1),
(2), (4) Date: Mar. 15, 2011

(87) PCT Pub. No.: WO2010/032010
PCT Pub. Date: Mar. 25, 2010

(65) Prior Publication Data
US 2011/0190302 A1    Aug. 4, 2011

Related U.S. Application Data

(60) Provisional application No. 61/098,275, filed on Sep. 19, 2008.

(30) Foreign Application Priority Data

Sep. 19, 2008   (GB) .................................. 0817208.2

(51) Int. Cl.
*A61K 31/5375* (2006.01)
*A61K 31/18* (2006.01)
*C07D 265/30* (2006.01)
*C07C 311/01* (2006.01)

(52) U.S. Cl. ..................... 514/239.5; 514/601; 544/106; 564/92

(58) Field of Classification Search ................ 514/239.5, 514/601; 544/106; 564/92
See application file for complete search history.

(56) References Cited

U.S. PATENT DOCUMENTS

| 4,119,784 | A  | 10/1978 | Conrow |
| 4,948,809 | A  | 8/1990  | Witte |
| 5,760,028 | A  | 6/1998  | Jadhav et al. |
| 6,159,995 | A  | 12/2000 | Thorwart et al. |
| 6,451,824 | B1 | 9/2002  | Thorwart et al. |
| 2003/0144292 | A1 | 7/2003 | Natchus et al. |
| 2005/0119305 | A1 | 6/2005 | Naka et al. |
| 2005/0227987 | A1 | 10/2005 | Vicker |
| 2007/0191370 | A1 | 8/2007 | Devasagayaraj |
| 2011/0172189 | A1 | 7/2011 | Greig et al. |

FOREIGN PATENT DOCUMENTS

| DE | 10 46 220 | | 12/1958 |
| DE | 3000519 | A1 | 8/1980 |
| EP | 0877018 | A1 | 5/1998 |
| EP | 0 960 882 | | 12/1999 |
| EP | 0 877 019 | | 12/2001 |
| EP | 0 988 018 | | 3/2003 |
| EP | 1 431 267 | | 6/2004 |
| EP | 1 491 190 | | 12/2004 |
| EP | 1659113 | A1 | 5/2006 |
| JP | 11246527 | | 9/1999 |
| WO | WO 96/37492 | | 11/1996 |
| WO | WO 97/16433 | | 5/1997 |
| WO | WO 97/33887 | | 9/1997 |
| WO | WO 98/03166 | | 1/1998 |
| WO | WO 98/23608 | | 6/1998 |
| WO | WO 98/43962 | | 10/1998 |
| WO | WO 98/50342 | | 11/1998 |
| WO | WO 99/37621 | | 7/1999 |
| WO | WO 99/42443 | | 8/1999 |
| WO | WO 99/59992 | A1 | 11/1999 |
| WO | WO 01/16137 | | 3/2001 |
| WO | WO 01/90077 | | 11/2001 |
| WO | WO 02/060867 | | 8/2002 |
| WO | WO 02/074298 | | 9/2002 |
| WO | WO 03/037321 | | 5/2003 |

(Continued)

OTHER PUBLICATIONS

Armour K.J., et al., 2001, "Inhibition of bone resorption in vitro and prevention of ovariectomy-induced bone loss in vivo by flurbiprofen nitroxybutylester (HCT1026)," Arthritis and Rheumatism, vol. 44, No. 9, pp. 2185-2192.

(Continued)

*Primary Examiner* — Rebecca Anderson
*Assistant Examiner* — Samantha Shterengarts
(74) *Attorney, Agent, or Firm* — Swanson & Bratschun, L.L.C.

(57) ABSTRACT

The present invention pertains generally to the field of therapeutic compounds, and more specifically to certain aryl-phenyl-sulfonamido-phenylene compounds of the following formula (I) (collectively referred to herein as "APSAP compounds"). The present invention also pertains to pharmaceutical compositions comprising such compounds, and the use of such compounds and compositions, both in vitro and in vivo, in treatment, for example, of inflammation and/or joint destruction and/or bone loss; of disorders mediated by excessive and/or inappropriate and/or prolonged activation of the immune system; of inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like; of disorders associated with bone loss, such as bone loss associated with excessive osteoclast activity in rheumatoid arthritis, osteoporosis, cancer-associated bone disease, Paget's disease and the like, etc.; and of cancer, such as a haematological malignancy, a solid tumor, etc.

22 Claims, 2 Drawing Sheets

FOREIGN PATENT DOCUMENTS

| | | |
|---|---|---|
| WO | WO 2004/022561 | 3/2004 |
| WO | WO 2004/039784 | 5/2004 |
| WO | WO 2004/073619 | 9/2004 |
| WO | WO 2004/098582 | 11/2004 |
| WO | WO 2004/106290 A1 | 12/2004 |
| WO | WO 2005/060963 A1 | 7/2005 |
| WO | WO 2005/085189 A2 | 9/2005 |
| WO | WO 2005/105712 A1 | 11/2005 |
| WO | WO 2005/118528 | 12/2005 |
| WO | WO 2006/134467 A1 | 12/2006 |
| WO | WO 2007/008541 A2 | 1/2007 |
| WO | WO 2007/026962 A1 | 3/2007 |
| WO | WO 2008/114022 | 9/2008 |
| WO | WO 2010/032009 A1 | 3/2010 |

OTHER PUBLICATIONS

Augstein, J., et al., 1965, "Some cardiovascular effects of a series of aryloxyalkylamines 1", J. Med. Chem., vol. 8, pp. 356-367.

Baud et al., 1999, "Signaling by proinflammatory cytokines: oligomerization of TRAF2 and TRAF6 is sufficient for JNK and IKK activation and target gene induction via an amino-terminal effector domain", Genes Dev., vol. 13, pp. 1297-1308.

Baud et al., 2009, "Is NfkB a good target for cancer therapy? Hopes and pitfalls", Nat. Rev. Drug Disc., vol. 8, pp. 33-40.

Brennan et al., 1989, "Inhibitory effect of TNF alpha antibodies on synovial cell interleukin-1 production in rheumatoid arthritis", Lancet, vol. 2, pp. 244-247.

Brennan et al., 1992, "Enhanced expression of tumor necrosis factor receptor mRNA and protein in mononuclear cells isolated from rheumatoid arthritis synovial joints", Eur. J. Immunol., vol. 22, pp. 1907-1912.

Brennan et al., 1996, "Cytokines in autoimmunity", Curr. Opin. Immunol., vol. 8, pp. 872-877.

Corey EJ, Shibata S, Bakshi RK, 1988, "An effcicient and catalytically enantioselective route to (S)-(-)-Phenyloxirane," J. Org. Chem., vol. 53, pp. 2861-2863.

Coxon, F.P., et al., 2000, "Protein geranylgeranylation is required for osteoclast formation, function, and survival: inhibition by bisphosphonates and GGTI-298," J.Bone Miner.Res., vol. 15, pp. 1467-1476.

Degenhardt, C.R., et al., 1986, "Synthesis of Ethenylidenebis(phosphonic acid) and its Tetraalkyl Esters," J. Org. Chem., vol. 51, pp. 3488-3490.

Eberhard, A., et al., 1965, "Hydrolysis of Phostonates," J. Amer. Chem. Soc., vol. 87, pp. 253-260.

Elliott et al., 1994, "Randomised double-blind comparison of chimeric monoclonal antibody to tumour necrosis factor alpha (cA2) versus placebo in rheumatoid arthritis", Lancet, vol. 344, pp. 1105-1110.

Feldmann et al., 1994, "TNF alpha as a therapeutic target in rheumatoid arthritis," Circ. Shock, vol. 43, pp. 179-184.

Feldmann et al., 1996, "Rheumatoid arthritis", Cell, vol. 85, pp. 307-310.

Feldmann et al., 2001, "The role of TNF alpha and IL-1 in rheumatoid arthritis," Curr. Dir. Autoimmun., vol. 3, pp. 188-199.

Firestein et al., 1999, "Signal transduction and transcription factors in rheumatic disease", Arthritis Rheum., vol. 42, pp. 609-621.

Firestein, 1996, "Invasive fibroblast-like synoviocytes in rheumatoid arthritis. Passive responders or transformed aggressors?", Arthritis Rheum., vol. 39, pp. 1781-1790.

Firestein, 2005 "Immunologic mechanisms in the pathogenesis of rheumatoid arthritis", J. Clin. Rheumatol., vol. 11. pp. S39-S44.

Gottlieb, 2005, "Psoriasis: Emerging Therapeutic Strategies", Nat. Rev. Drug Disc., vol. 4, pp. 19-34.

Greig et al., 2006, "Development and characterization of biphenylsulfonamides as novel inhibitors of bone resorption", J. Med. Chem., vol. 49: pp. 7487-7492.

Ha-Duong, N-T, et al, 2001, "Synthesis of sulfaphenazole derivatives and their use as inhibitors and tools for comparing the active sites of human liver cytochromes P450 of the 2C subfamily", J. Med. Chem., vol. 44, pp. 3622-3631.

Herczegh, P., et al, 2002, "Osteoadsorptive Bisphosphonate Derivatives of Fluoroquinolone Antibacterials," J. Med. Chem., vol. 45, pp. 2338-2341.

Hughes, D.E., et al., 1997, "Apoptosis in bone physiology and disease," J. Clin. Pathol.: Molecular Pathology, vol. 50, pp. 132-137.

Jimi et al., 2004, "Selective inhibition of NF-kappa B blocks osteoclastogenesis and prevents inflammatory bone destruction in vivo", Nat. Med., vol. 10, pp. 617-624.

Joosten et al., 1996, "Anticytokine treatment of established type II collagen-induced arthritis in DBA/1 mice. A comparative study using anti-TNF alpha, anti-IL-1 alpha/beta, and IL-1Ra," Arthritis Rheum., vol. 39, pp. 797-809.

Klareskog et al., 2006, "A long-term, open-label trial of the safety and efficacy of etanercept (Enbrel) in patients with rheumatoid arthritis not treated with other disease-modifying antirheumatic drugs", Ann. Rheum. Dis., vol. 65, pp. 1578-1584.

Klareskog et al., 2006, "Mechanisms of disease: Genetic susceptibility and environmental triggers in the development of rheumatoid arthritis," Nat. Clin. Pract. Rheumatol., vol. 2, pp. 425-433.

Kong, Y.Y., et al., 1999, "OPGL is a key regulator of osteoclastogenesis, lymphocyte development and lymph-node organogenesis," Nature, vol. 397, pp. 315-323.

Korzenik et al., 2006, "Evolving knowledge and therpy of inflammatory bowel disease," Nat. Rev. Drug Disc., vol. 5, pp. 197-209.

Li et al., 2008, "A tumor necrosis factor-[alpha]-mediated pathway promoting autosomal dominant polycystic kidney disease", Nature Medicine, vol. 14(8), pp. 863-868.

Liu, 2005, "Molecular mechanism of TNF signaling and beyond," Cell Res., vol. 15(1), pp. 24-27.

Luckman et al.. 1998, "Heterocycle-containing bisphosphonates cause apoptosis and inhibit bone resorption by preventing protein prenylation: evidence from structure-activity relationships in J774 macrophages," J. Bone Miner. Res., vol. 13, pp. 1668-1678.

MacPherson, H; et al., 1999, "Expression and functional role of nitric oxide synthase isoforms in human osteoblast-like cells," Bone, vol. 24, pp. 179-185.

Mantovani, 2009, "Inflaming metastasis", Nature, vol. 457, pp. 36-37.

McInnes et al., 2005, "Targeting cytokines beyond tumor necrosis factor-alpha and interleukin-1 in rheumatoid arthritis", Curr. Pain Headache Rep., vol. 9, pp. 405-411.

Mount et al., 2005, "Rheumatoid arthritis market", Nat. Rev. Drug Disc., vol. 2, pp. 11-12.

Mundy, G.R., 1996, "Chapter 1: Bone Remodeling", in Bone Remodeling and its disorders (2nd edition), London, (Ed. Martin Dunitz), pp. 1-11.

Nociari et al., 1998, "A Novel one-step, highly sensitive fluorimetric assay to evaluate cell-mediated cytotoxicity", Journal of Immunological Methods, vol. 213, pp. 157-167.

Nyormoi, O., et al., 2003, "An MMP-2/MMP-9 inhibitor, 5a, enhances apoptosis induced by ligands of the TNF receptor superfamily in cancer cells", Cell Death and Differentiation, vol. 10, pp. 558-569.

O'Brien et al., 2000, "Structure-activity relationships and pharmacokinetic analysis for a series of potent, systemically available biphenylsulfonamide matrix metalloproteinase inhibitors". J. Med. Chem. vol. 43: pp. 156-166.

Peyman, A., et al., 2001, "αvβ3 antagonists based on a central thiophene scaffold", Bio. & Med. Chem. Letters, Vo. 11, pp. 2011-2015.

Philchenkov et al., 2004, "Caspases and cancer: mechanisms of inactivation and new treatment modalities", Exp. Oncol., vol. 26(2), pp. 82-97.

Raisz, L.G., 1988, "Local and systemic factors in the pathogenesis of osteoporosis," N. Engl. J. Med., vol. 318, pp. 818-828.

Ralston, S.H., 1997, "Science, Medicine and the Future: Osteoporosis," Br. Med. J., vol. 315, pp. 469-472.

Ramachandran PV, Gong B, Brown HC, 1995, "Chiral synthesis via organoboranes", J. Org. Chem., vol. 60, pp. 41-46.

Rodan, G.A., et al., 1997, "The missing bone," Cell, vol. 89, pp. 677-680.

Roodman, 2006, "Regulation of osteoclast differentiation", Ann. N. Y. Acad. Sci., vol. 1068, pp. 100-109.

Smolen et al., 2003, "Therapeutic Strategies for Rheumatoid Arthritis", Nat. Rev. Drug Disc., vol. 2, pp. 473-488.
Takahashi, N.; et al., 1988, "Osteoblastic cells are involved in osteoclast formation," Endocrinology, vol. 123, pp. 2600-2602.
Takasuka, M., et al., 1991, "FTIR spectral study of intramolecular hydrogen bonding in thromboxane A2 receptor antagonist S-145 and related compounds. 3. Conformation and activity of S-145 analogues", J. Med. Chem., vol. 34, pp. 1885-1891.
Tanaka et al., 2003, Signal transduction pathways regulating osteoclast differentiation and function, J. Bone Miner. Metab., vol. 21, pp. 123-133.
van den Berg et al., 1999, "Pathogenesis of joint damage in rheumatoid arthritis: evidence of a dominant role for interleukin-I", Baillieres Best Pract. Res. Clin. Rheumatol., vol. 13(4), pp. 577-597.
van den Berg, 2002, "Is there a rationale for combined TNF and IL-1 blocking in arthritis?", Clin. Exp. Rheumatol., vol. 20, pp. S21-S25.
van't Hof, R.J., et a;., 1997, "Cytokine-induced nitric oxide inhibits bone resorption by inducing apoptosis of osteoclast progenitors and suppressing osteoclast activity," J. Bone & Miner. Res., vol. 12(11), pp. 1797-1804.
Weissmann, 2006, "The pathogenesis of rheumatoid arthritis," Bull. Hosp. Jt. Dis., vol. 64, pp. 12-15.
Yasuda, H., et al, 1998, "Identity of osteoclastogenesis inhibitory factor (OCIF) and osteoprotegerin (OPG): a mechanism by which OPG/OCIF inhibits osteoclastogenesis in vitro", Endocrinology, vol. 139(3), pp. 1329-1337.
Ziff, 1990, "Rheumatoid arthritis—it's present and future", J. Rheumatol., vol. 17, pp. 127-133.
UK Search Report for GB 705400.0, Jul. 6, 2007.
International Search Report (ISR) and Written Opinion of International Searching Authority (WOISA) for PCT/GB2008/000989, 2009.
International Preliminary Report on Patentability (IPRP) for PCT/GB2008/000989, 2009.
UK Search Report for GB 0817207.4, Jan. 7, 2009.
International Search Report (ISR) and Written Opinion of International Searching Authority (WOISA) for PCT/GB2009/002221, 2009.
International Preliminary Report on Patentability (IPRP) for PCT/GB2009/002221.
UK Search Report for GB 0817208.2, Jan. 8, 2009.
International Search Report (ISR) and Written Opinion of International Searching Authority (WOISA) for PCT/GB2009/002223, Sep. 2, 2010.
International Preliminary Report on Patentability (IPRP) for PCT/GB2009/002223. Mar. 22, 2011.
UK Search Report for GB 0412553.0, Sep. 30, 2004.
International Search Report (ISR) and Written Opinion of International Searching Authority (WOISA) for PCT/GB2005/002043, 2006.
International Preliminary Report on Patentability (IPRP) for PCT/GB2005/002043) 2006.
Argus et al., 1958, "Distribution studies with sulphur 35-labelled disulfonamides in tumor-bearing and tumor-free mice", Brit. J. Cancer, vol. 12, pp. 636-644.
CHEMCATS record for Enamine Screening Library, Enamine, Kiev, Ukraine, publication date Jan. 17, 2008, CAS Registry No. 950020-41-4 (2 pages).
CHEMCATS record for LaboTest Stock Catalog, LaboTest, Niederschoena, Germany, publication date Jul. 24, 2007, CAS Registry No. 331653-75-9 (2 pages).
CHEMCATS records for Nanosyn Compound Library, Nanosyn Combinatorial Synthesis Inc., Menlo Park, CA, USA, publication date Apr. 17, 2007, CAS Registry Nos. 313495-94-2, 313521-07-2 (3 pages).
CHEMCATS record for Ryan Scientific Screening Library, Ryan Scientific, Inc., Mt. Pleasant, SC, USA, publication date Jan. 25, 2008, CAS Registry No. 302603-86-7 (2 pages).
CHEMCATS record for Scientific Exchange Product List, Scientific Exchange, Inc., Centre Ossipee, NH, USA, publication date Jan. 30, 2008, CAS Registry No. 312756-83-5 (2 pages).
CHEMCATS records for Spectrum Info Catalog, Spectrum Info Ltd., Kiev, Ukraine, publication date Sep. 5, 2007: CAS Registry No. 885269-21-6, 885269-32-9, 885269-42-1, 885269-85-2, 885269-88-5, 885269-91-0 (7 pages).
Mohan et al., 1993, "Structure-Activity Relationship Studies with Symmetric Naphthalenesulfonic Acid Derivatives. Synthesis and Influence of Spacer and Naphthalenesulfonic Acid Moiety on Anti-HIV-1 Activity", J. Med. Chem., vol. 36, pp. 1996-2003.

ARYL-PHENYL-SULFONAMIDE-PHENYLENE COMPOUNDS AND THEIR USE

RELATED APPLICATIONS

This application is 35 U.S.C. §371 national phase application of PCT/GB2009/002223, filed Sep. 18, 2009 (WO 2010/032010), entitled "Aryl-Phenyl-Sulfonamide-Phenylene Compounds and Their Use". PCT/GB2009/002223 is a nonprovisional application of U.S. provisional patent application No. 61/098,275 filed Sep. 19, 2008 and United Kingdom patent application number 0817208.2 filed Sep. 19, 2008, the contents of each of which are incorporated herein by reference in their entirety.

TECHNICAL FIELD

The present invention pertains generally to the field of therapeutic compounds, and more specifically to certain aryl-phenyl-sulfonamido-phenylene compounds (collectively referred to herein as "APSAP compounds"). The present invention also pertains to pharmaceutical compositions comprising such compounds, and the use of such compounds and compositions, both in vitro and in vivo, in treatment, for example, of inflammation and/or joint destruction and/or bone loss; of disorders mediated by excessive and/or inappropriate and/or prolonged activation of the immune system; of inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like; of disorders associated with bone loss, such as bone loss associated with excessive osteoclast activity in rheumatoid arthritis, osteoporosis, cancer-associated bone disease, Paget's disease and the like, etc.; and of cancer, such as a haematological malignancy, a solid tumour, etc.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Rheumatoid Arthritis

Rheumatoid arthritis (RA) is a chronic inflammatory disease characterised by painful swelling, stiffness, loss of movement and the destruction of cartilage and bone. RA is characterised by an inflammation of the synovial lining of multiple joints and commonly affects the joints of the wrist and hands and may also affect the elbows, shoulders, hips, neck and knees; the ultimate hallmark of RA is joint destruction. RA is a common disease, estimated to affect up to 1% of adults in the developed world, with women more than twice as likely to be affected and over 30% of patients likely to become severely disabled within 20 years (see, e.g., Feldmann et al., 2006). RA is one of the most important causes of disability in the western world and is associated with a significant reduction in quality of life as well as increased mortality if left untreated. The disease can start at any age, with individuals aged between 40 and 70 most commonly affected.

The exact cause of RA remains unclear, but is highly complex and may involve the combination of a number of factors which lead to the development of autoantibodies, formation of immune complexes, production of pro-inflammatory cytokines, angiogenesis and eventual bone and cartilage loss (see, e.g., Klareskog et al, 2006; Ziff et al, 1990; Weissmann et al, 2006; Firestein et al, 2005). These factors include an abnormal immune response caused by reduced self tolerance or a biological trigger such as reaction to environmental factors, infectious agents, or hormonal stimulus (see, e.g., Klareskog et al, 2006); antibodies to the Fc fragment of IgG, known as rheumatoid factor, are present in 60-80% of adults with RA (see, e.g., Weissmann et al, 2006) but it is not known whether this factor is responsible for initiating the inflammatory cascade or is generated at a later stage and propagates the process (see, e.g., Weissmann et al, 2006); there is also a notable genetic predisposition to the disease, as shown by the presence of HLA-DR4 antibody in 70% of patients (see, e.g., Klareskog et al, 2006). At the cellular level, development of RA usually commences with T-cells infiltrating the synovial membrane lining the affected joint; this then leads to the activation of macrophages, monocytes and synovial fibroblasts (see, e.g., Firestein, 1996) by way of cell-cell contact and release of various cytokines, including TNFα and IL-1 (see, e.g., Feldmann, 1996). Activation of these cells leads to the overproduction of a range of pro-inflammatory cytokines, of which the most important are TNFα, IL-1 and IL-6 (see, e.g., Brennan et al, 1996; McInnes et al, 2005). These pro-inflammatory cytokines are then instrumental in orchestrating several complex signal transduction cascades, including the NFκB, MAPK and Jak/STAT pathways (see, e.g., Firestein et al, 1999) which lead to the induction of genes coding for various products that propagate the inflammatory response and also promote tissue destruction. These products include tissue-degrading enzymes such as collagenases, matrix metalloproteases, cathepsins, and other pro-inflammatory factors such as selectins, integrins, leukotrienes, prostaglandins, chemokines, and other cytokines. Furthermore, TNFα and IL-1 also induce RANKL expression.

RANKL is an essential factor for the generation of osteoclasts (see, e.g., Tanaka et al, 2003; Roodman, 2006), and upregulated RANKL-production leads to increased osteoclast differentiation and ultimately bone destruction (see, e.g., Tanaka et al, 2003; Roodman, 2006). The inflammatory response leads to the accumulation of many leukocytes and immune factor populations within the affected joint and also to hyperplasia of the Type-A and Type-B synoviocytes (see, e.g., Firestein et al, 2005), leading to thickening and vascularisation of the synovium into a destructive and aggressive tissue known as a pannus. The pannus contains both osteoclasts, which destroy bone, and metalloproteases, which continue the destruction of cartilage.

Treatment of Rheumatoid Arthritis

Early therapies for RA focussed on controlling the symptoms of the disease, mainly by reduction of inflammation, rather than retarding disease progression. These drugs included NSAIDs such as aspirin, diclofenac and naproxen and, until recently, the COX-2 selective drugs Celebrex® and Vioxx® were also widely used. Inflammation was further controlled by glucocorticoids, and their combination with NSAIDs provided reasonably effective short-term control of the inflammation. More recently, a more aggressive approach to treating RA has been introduced starting at disease onset, using so-called disease-modifying anti-rheumatic drugs (DMARDs), which act to slow or even prevent disease progression. These include a number of older drugs, including gold salts; sulfasalazine; antimalarials such as hydroxychloroquine; D-penicillamine; immunosuppressants such as mycophenolic acid, azathioprine, cyclosporine A, tacrolimus and sirolimus; minocycline; leflunomide; and most importantly, methotrexate (see, e.g., Smolen et al, 2003).

Methotrexate is now the gold-standard therapy for clinical trial comparisons, and is generally used in combination with newer therapies. It is effective in most patients but, in common with all of the above agents, has significant gastrointestinal side effects, which lead to roughly 50% of patients eventually having to cease treatment with methotrexate (see, e.g., Mount et al, 2005). A further drawback of these older DMARDs is the length of time taken for the drug to start acting, ranging from weeks with methoxtrexate, to months with gold salts. Whilst full remissions only occur in about a quarter of patients, for those showing no effect it is not generally possible to stop therapy without suffering the risk of a more violent disease rebound (see, e.g., Smolen et al, 2003). In recent years, the treatment of RA has been revolutionised by the advent of biological agents which target specific inflammatory pathways. The first and most important of these are the anti-tumour necrosis factor (anti-TNF) agents (see, e.g., Elliott et al, 1994).

The Role of TNFα in RA

As discussed above, the TNF superfamily of receptors and ligands plays a key role in the causation of inflammation and associated local and systemic bone loss. TNFα production within the joint may in fact play the pivotal role in orchestrating the production of other factors which leads to the persistence of inflammation and tissue damage (see, e.g., Feldmann et al, 2001; Brennan et al, 1999; Brennan, 1992). The importance of TNFα in RA is highlighted by the finding that antibodies blocking TNFα can prevent inflammation in animal models of RA, and that anti-TNFα therapy is currently the most effective treatment for RA (see, e.g., Elliott et al, 1994; Feldmann et al, 1994; Joosten et al 1996, Klareskog et al, 2006). However, there is evidence that there are some TNFα-independent effects of IL-1 in RA, most notably bone destruction (see, e.g., van den Berg et al, 1999; van den Berg et al, 2002).

TNFα is a cytokine that effects many different functions, including the alteration of tissue remodelling, changes to the permeability of the epithelial cell barrier, activation of macrophages, up-regulation of adhesion molecules, recruitment of other immune response effectors and, most importantly in RA, it instigates the signalling cascade which leads to the activation of the transcription factors NFκB and AP-1 (see, e.g., Liu, 2005; Baud et al, 1999). Binding of TNFα and IL-1 to their respective receptors leads to the recruitment of downstream signal transducers called TRAFs. Further kinases are recruited by the TRAFs, and the resulting kinase complex activates the MAP-kinase pathway, ultimately leading to activation of AP-1, and the phosphorylation of IκB kinase. IκB is the inhibitor of NFκB, which acts by preventing translocation of NFκB to the nucleus. Phosphorylation of IκB by IκB kinase leads to degradation of IκB. Once IκB has been degraded, NFκB migrates to the nucleus, where it promotes transcription of anti-apoptotic genes, which promote survival of T and B-cells, thereby prolonging the immune response. This prolongation of the inflammatory response is central to the chronic nature of RA. The importance of NFκB activation is demonstrated by the fact that inhibition of NFκB activity by inhibitory peptides can prevent arthritis in animal models of RA (see, e.g., Jimi et al, 2004).

Anti-TNFα Therapy

Anti-TNFα therapy represents the market-leading therapies for RA, and is performed either with neutralising antibodies such as infliximab (Remicade® J&J and Schering Plough) and adalimumab (Humira®, Abbott) or decoy receptors such as etanercept (Enbrel® Amgen and Wyeth), both which represent validated and highly effective treatments for RA. Anti-TNFα biologicals are already licensed for RA, Crohn's disease, and psoriasis. A number of other inflammatory and autoimmune disorders are also being investigated as potential targets. Other approaches to blocking the action of TNFα include the pegylated anti-TNFα fragment certolizumab (Cimzia®, UCB); inhibition of proximal signalling intermediates such as MAP kinase; interference with the synthesis of TNFα via inhibition of TNFα converting enzyme (TACE); and inhibition of the metalloproteases responsible for cleaving TNFα from the cell surface (see, e.g., Smolen et al, 2003; Mount et al, 2005).

Other Inhibitors of NFκB Activation

As described above, the binding of IL-1 and RANKL to their receptors also initiates a signalling cascade, which eventually leads to the activation of NFκB and subsequent inflammatory response. The efficacy of inhibitors of these ligands has been validated by the use of the IL-1 receptor antagonist anakinra (Kineret® Amgen) for the treatment of RA, and the completion of clinical trials for the monoclonal antibody against RANKL AMG-162 (Denosumab® Amgen) for osteoporosis (it is also in clinical trials for RA and psoriasis).

Other Common Inflammatory Diseases Mediated by TNFα

There are several other common inflammatory diseases in which TNFα has been shown to play a major role and in which TNFα inhibitors have found therapeutic use. These include inflammatory bowel disease (IBD) and psoriasis.

IBD is an inflammatory disorder of the gut affecting about 0.25% of the population in the western world, of which the two main forms are: ulcerative colitis (UC), in which the lining of the colon becomes inflamed and ulcerated; and Crohn's disease (CD), which can occur anywhere within the gastrointestinal tract, but most often the ileum, and commonly involves inflammation of the entire gut wall. Common symptoms of IBD are bloody diarrhea and abdominal pain.

Psoriasis is an inflammatory response of the skin affecting 1-3% of the population in the western world. The disease is characterised by raised, red, scaly plaques on the skin, which may be itchy and also cause significant psychological distress by their unsightly nature. A further complication of psoriasis is the development of psoriatic arthritis, an inflammatory arthritis of the joints, in up to 40% of patients, which develops on average 10 years after the first symptoms of skin disease are seen (see, e.g., Gottlieb, 2005).

As with RA, the aetiology of IBD and psoriasis are unknown and may involve a complex combination of infectious agents, environmental, and genetic factors, generating an inappropriate and prolonged inflammatory response.

Treatment of IBD and psoriasis has followed a similar pattern to that of RA, with the past use of immunoregulatory agents such as NSAIDs, methotrexate, cyclosporine, steroids, and antimetabolites such as 6-mercaptopurine for IBD (see, e.g., Korzenik et al, 2006) and methotrexate and cyclosporine for psoriasis (see, e.g., Gottlieb, 2005). The treatment of both has been revolutionised by the advent of biological agents, in particular those which block TNFα signalling. Etanercept is licensed for the treatment of psoriasis and psoriatic arthritis; both infliximab and adalimumab are licensed for psoriatic arthritis, IBD, and psoriasis.

Cancer

There is growing evidence that activation of NFκB can play a major role in the promotion and progression of both haematological malignancies, such as myeloma and lymphomas, and solid tumours, such as breast, prostate and lung cancer (see, e.g., Baud and Karin, 2009). There is also rising awareness of the role and importance of inflammation in cancer and in the development of resistance to radiotherapy and to chemotherapeutic agents, and it has been suggested that inflammation is in fact one of the basic hallmarks of cancer (see, e.g., Mantovani, 2009). Improving the efficacy of anti-cancer treatments by prevention of NFκB activation is therefore a promising strategy to augment existing therapeutic regimes and is currently under investigation, most notably for the treatment of multiple myeloma.

Defects in the normal apoptotic pathways are also implicated in the development and progression of tumour cell growth. Apoptosis (programmed cell death) plays a key role in the removal of abnormal cells; defects in the signalling cascades, which would normally lead to its induction, play a key role in oncogenesis. Radiotherapy and many chemotherapeutic agents act by causing cellular damage, which would normally induce apoptosis; defects in the pathway will therefore also reduce the effectiveness of such agents. The most important effector molecules in the signalling pathway leading to apoptosis are known as the caspases, which may be triggered by a number of stimuli, including TNFα binding to its receptor. Mutations in the genes which encode for the caspases have been found in a number of tumour types, including gastric, breast, renal cell and cervical cancers as well as commonly in T-cell lymphoblastic lymphoma and basal cell ameloblastomas (see, e.g., Philchenkov et al., 2004). Compounds which activate caspases, and thus sensitise cells to apoptosis, would be highly effective as cancer therapies either as single agents or in enhancing the effectiveness of existing cancer chemotherapy and radiotherapy.

Common Bone Diseases

Osteoporosis is a common disease characterised by reduced bone density, deterioration of bone tissue, and an increased risk of fracture. Many factors contribute to the pathogenesis of osteoporosis including poor diet, lack of exercise, smoking, and excessive alcohol intake. Osteoporosis may also arise in association with inflammatory diseases such as rheumatoid arthritis, endocrine diseases such as thyrotoxicosis, and with certain drug treatments such as treatment with glucocorticoids. However one of the most important factors in the pathogenesis of osteoporosis is heredity.

Paget's disease of bone is a common condition of unknown cause, characterised by increased bone turnover and disorganised bone remodelling, with areas of increased osteoclastic and osteoblast activity. Although Pagetic bone is often denser than normal, the abnormal architecture causes the bone to be mechanically weak, resulting in bone deformity and increased susceptibility to pathological fracture.

Many types of cancer affect bone. Cancer-associated bone disease can be manifest by the occurrence of hypercalcaemia or the development of osteolytic and/or osteosclerotic metastases. Increased osteoclastic bone resorption plays a key role in the pathogenesis of both conditions. Whilst almost any cancer can be complicated by bone metastases, the most common sources are multiple myeloma, breast carcinoma, and prostate carcinoma. The most common tumours associated with hypercalcaemia are multiple myeloma, breast carcinoma, and lung carcinoma.

RANKL signalling has been shown to play a major role in osteoclast over-activity and a consequent increase in bone loss (see, e.g., Tanaka et al, 2003; Roodman, 2006). The use of drugs which affect this pathway has been validated by the completion of clinical trials of the monoclonal antibody against RANKL AMG-162 (Denosumab® Amgen) for the treatment of osteoporosis/multiple myeloma.

As described previously, bone loss also plays a major role in the pathophysiology of rheumatoid arthritis and drugs which prevent activation of the signalling pathways described (e.g. TNFα blockers) are also able to prevent this bone loss.

Agents that Prevent Inflammation and/or Bone Loss

The inventors have identified a new class of compounds which, for example, prevent inflammation and/or bone loss, and thus may be used in the treatment of diseases with an inflammatory or autoimmune component, including, for example, rheumatoid arthritis, inflammatory bowel disease, psoriasis, and psoriatic arthritis; diseases which involve bone loss, including, for example, bone loss associated with rheumatoid arthritis, osteoporosis, Paget's disease of bone, and multiple myeloma; as well as cancer associated with activation of NFκB, with aberrant NFκB signaling, or with inflammation, including haematological malignancies such as multiple myeloma, leukaemia, T-cell lymphoblastic lymphoma, and other lymphoma (e.g., non-Hodgkin Lymphoma), and solid tumours such as cancer of the bladder, breast cancer (female and/or male), colon cancer, kidney cancer, lung cancer, pancreatic cancer, prostate cancer, brain cancer, skin cancer, thyroid cancer, and melanoma; and cancer associated with the inactivation or impairment of caspase-mediated cell death, such as gastric cancer, breast cancer, renal cancer, cervical cancer, and basal cell ameloblastomas.

Without wishing to be bound by any particular theory, the inventors believe that this action may be via a mechanism that involves blocking TNFα and/or IL-1 and/or RANKL-signalling.

Biphenyl Sulfonamides

Greig et al., 2004 and Greig et al., 2006 describe a class of biphenyl alkyl sulfonamides as anti-resorptive agents for the treatment of bone diseases, including, for example, 2',4'-difluoro-biphenyl-4-sulfonic acid (5-hydroxy-pentyl)-amide (ABD248) and 2',4'-difluoro-biphenyl-4-sulfonic acid (4-hydroxy-butyl)-amide (ABD256) (shown below).

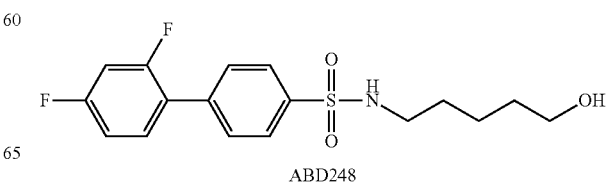

ABD248

-continued

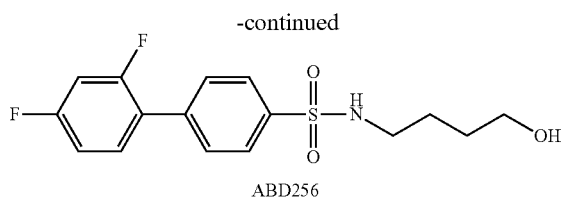

ABD256

Greig et al., 2008 (not yet published), describes a class of biphenyl alkyl sulfonamides, as anti-resorptive agents for the treatment of bone diseases including, for example, 2',4'-difluoro-biphenyl-4-sulfonic acid (3-hydroxymethyl-phenyl)-amide (ABD456), 2',4'-difluoro-biphenyl-4-sulfonic acid (4-hydroxymethyl-phenyl)-amide (ABD466), and 2',4'-difluoro-biphenyl-4-sulfonic acid [3-(2-hydroxy-ethyl)-phenyl]-amide (ABD628), shown below.

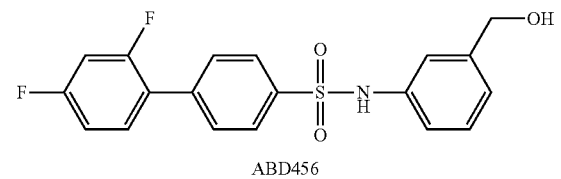

ABD456

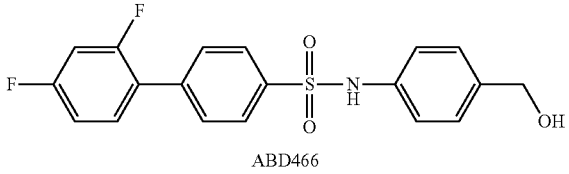

ABD466

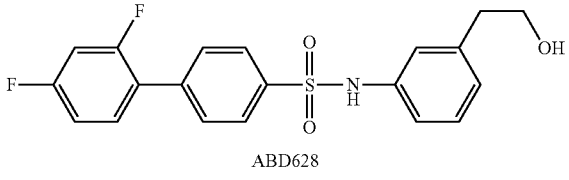

ABD628

It appears that compounds of the following formulae may be known:

| No. | Structure | Registry No. |
|---|---|---|
| 1 | 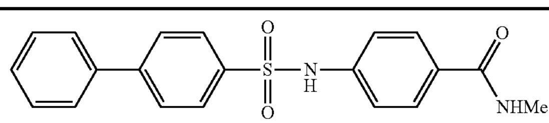 | 1022865-56-9 |
| 2 | ![structure](biphenyl-sulfonamide-morpholine) | 313238-50-5 |

The present inventors have identified a new a class of aryl sulfonamides, as defined herein, that have surprising and unexpected properties.

The present inventors have identified a new a class of aryl sulfonamides, as defined herein, that have, inter alia, one or more surprising and unexpected properties.

Without wishing to be bound to any particular theory, the inventors believe that the new compounds have been protected against the major route of metabolism acting upon the previous biphenyl aryl sulfonamides (specifically, oxidation of the terminal alcohol to give a carboxylic acid) by the addition of a suitable blocking group in this region. In addition to the resulting substantial improvement in metabolic stability, these blocking groups have also been selected to provide a further substantial enhancement in the aqueous solubility of the compounds. If a drug is to show oral activity, it must first be solvated, to permit absorption from the gastrointestinal tract. Second, the drug must be sufficiently resistant to first pass metabolism by metabolic enzymes contained within the liver so as to be able to enter the circulation and permit sufficient quantities to reach the biological target. Third, the drug must be sufficiently potent against the biological target to give the desired therapeutic effect.

The optimization of pharmacokinetic properties (action of the body on the drug) of a drug is a developmental barrier of equal challenge as compared to the optimization of pharmacodynamic properties (action of the drug on the body). By improving both solubility and stability, with little or no loss of potency against the biological target, the new compounds disclosed herein show substantial improvements in their properties as oral therapeutic agents, as compared to previous compounds identified above. The new compounds combine the characteristics required of orally active agents for the treatment of inflammatory diseases and/or for the treatment of bone loss.

SUMMARY OF THE INVENTION

One aspect of the invention pertains to certain aryl-phenyl-sulfonamido-phenylene compounds (for convenience, collectively referred to herein as "APSAP compounds"), as described herein.

Another aspect of the invention pertains to a composition (e.g., a pharmaceutical composition) comprising an APSAP compound, as described herein, and a pharmaceutically acceptable carrier or diluent.

Another aspect of the invention pertains to method of preparing a composition (e.g., a pharmaceutical composition) comprising the step of admixing an APSAP compound, as described herein, and a pharmaceutically acceptable carrier or diluent.

Another aspect of the invention pertains to a method of inhibiting an inflammatory response, in vitro or in vivo, comprising contacting an immune system component with an effective amount of an APSAP compound, as described herein.

Another aspect of the invention pertains to a method of inhibiting cellular and/or molecular pathways leading to joint destruction, in vitro or in vivo, comprising contacting cells associated with an immune response with a therapeutically-effective amount of an APSAP compound, as described herein.

Another aspect of the invention pertains to a method of inhibiting osteoclast survival, formation, and/or activity, in vitro or in vivo, comprising contacting an osteoclast with an effective amount of an APSAP compound, as described herein.

Another aspect of the invention pertains to a method of inhibiting bone resorption, in vitro or in vivo, comprising contacting cells in the bone microenvironment with a therapeutically-effective amount of an APSAP compound, as described herein.

Another aspect of the present invention pertains to a method of treatment comprising administering to a subject in need of treatment a therapeutically-effective amount of an APSAP compound, as described herein, preferably in the form of a pharmaceutical composition.

Another aspect of the present invention pertains to an APSAP compound as described herein for use in a method of treatment of the human or animal body by therapy.

Another aspect of the present invention pertains to use of an APSAP compound, as described herein, in the manufacture of a medicament for use in treatment.

In one embodiment, the treatment is treatment of inflammation and/or joint destruction and/or bone loss.

In one embodiment, the treatment is treatment of disorders mediated by excessive and/or inappropriate and/or prolonged activation of the immune system.

In one embodiment, the treatment is treatment of inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like.

In one embodiment, the treatment is treatment of inflammatory and autoimmune disorders, for example, rheumatoid arthritis, psoriasis, psoriatic arthritis, inflammatory bowel disease, ankylosing spondylitis, and the like.

In one embodiment, the treatment is treatment of disorders associated with bone loss, such as bone loss associated with excessive osteoclast activation in rheumatoid arthritis; osteoporosis; cancer-associated bone disease; Paget's disease; and the like.

In one embodiment, the treatment is treatment of a haematological malignancy, e.g., multiple myeloma, leukaemia, or lymphoma (e.g., non-Hodgkin Lymphoma), e.g., a haematological malignancy, multiple myeloma, leukaemia, or lymphoma (e.g., non-Hodgkin Lymphoma) associated with activation of NFκB, with aberrant NFκB signalling, or with inflammation, e.g., alone, or in combination with, and to augment the efficacy of, radiotherapy or chemotherapy.

In one embodiment, the treatment is treatment of a solid tumour cancer, e.g., cancer of the bladder, breast cancer (female and/or male), colon cancer, kidney cancer, lung cancer, pancreatic cancer, prostate cancer, brain cancer, skin cancer, thyroid cancer, or melanoma, e.g., a solid tumour cancer, cancer of the bladder, breast cancer (female and/or male), colon cancer, kidney cancer, lung cancer, pancreatic cancer, prostate cancer, brain cancer, skin cancer, thyroid cancer, and melanoma associated with activation of NFκB, with aberrant NFκB signalling, or with inflammation, e.g., alone, or in combination with, and to augment the efficacy of, radiotherapy or chemotherapy.

In one embodiment, the treatment is treatment of a haematological malignancy, e.g., T-cell lymphoblastic lymphoma, mantle cell lymphoma, or acute lymphoblastic leukemia, e.g., a haematological malignancy, T-cell lymphoblastic lymphoma, mantle cell lymphoma, or acute lymphoblastic leukemia associated with inactivation or impairment of caspase induction or with aberrant caspase signalling, e.g., alone or in combination with, and to augment the efficacy of, radiotherapy or chemotherapy.

In one embodiment, the treatment is treatment of a solid tumour cancer, e.g., renal cell carcinoma, breast cancer (female and/or male), gastric cancer, prostate cancer, colon cancer, or basal cell ameloblastoma, e.g., a solid tumour cancer, e.g., renal cell carcinoma, breast cancer (female and/or male), gastric cancer, prostate cancer, colon cancer, or basal cell ameloblastoma associated with inactivation or impairment of caspase induction or with aberrant caspase signalling, e.g., alone, or in combination with, and to augment the efficacy of, radiotherapy or chemotherapy.

In one embodiment, the treatment is part of treatment by combination therapy, e.g., in combination with, and to augment the efficacy of, radiotherapy or chemotherapy.

Another aspect of the present invention pertains to a kit comprising (a) an APSAP compound, as described herein, preferably provided as a pharmaceutical composition and in a suitable container and/or with suitable packaging; and (b) instructions for use, for example, written instructions on how to administer the compound.

Another aspect of the present invention pertains to an APSAP compound obtainable by a method of synthesis as described herein, or a method comprising a method of synthesis as described herein.

Another aspect of the present invention pertains to an APSAP compound obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

Figure 1:
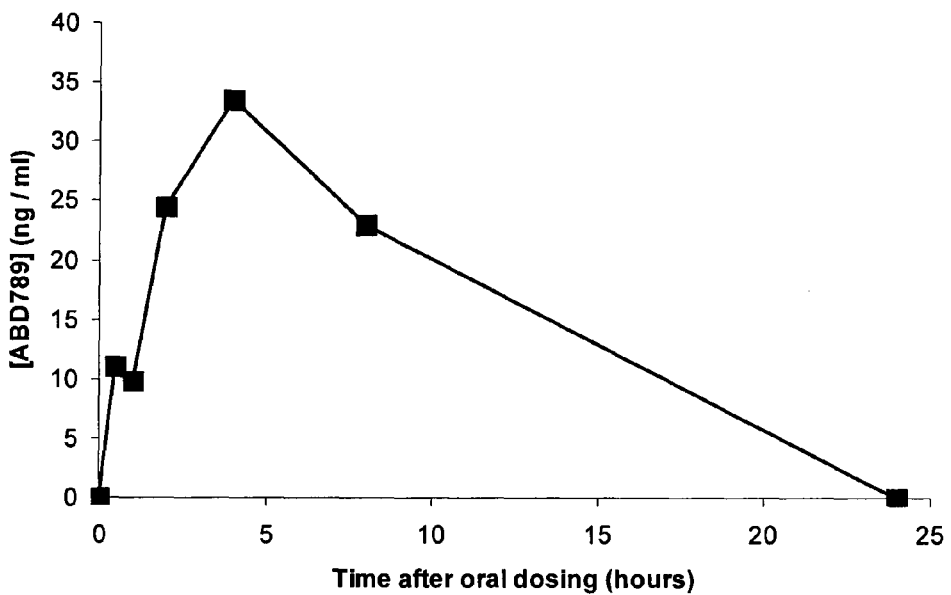
FIG. 1 is a graph showing mean plasma concentration (ng/mL) of the APSAP compound ABD789 (■) after oral administration (1 mg/kg) to a rat model.

The compounds of the present invention are structurally related to 1-(aryl)-phenyl-4-sulfonic acid (3-substituted-phenyl)amide:

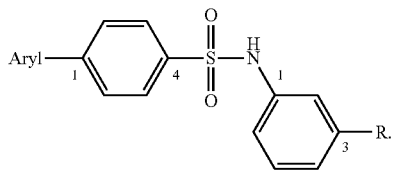

One aspect of the present invention pertains to compounds of the following formula, and pharmaceutically acceptable salts, hydrates, and solvates thereof (collectively referred to herein as "aryl-phenyl-sulfonamido-phenylene" or "APSAP compounds"):

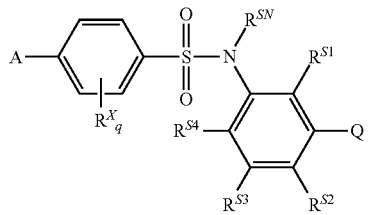

wherein:
-A is independently:

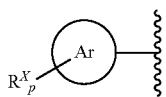

—Ar is independently phenyl, pyridinyl, or pyrimidinyl; and
p is independently an integer from 0 to 3;
and wherein:
q is independently an integer from 0 to 3;
and wherein:
—$R^{SN}$ is independently —H or saturated aliphatic $C_{1-4}$alkyl;
and wherein:
—$R^{S1}$ is independently —H or saturated aliphatic $C_{1-4}$alkyl;
—$R^{S2}$ is independently —H or saturated aliphatic $C_{1-4}$alkyl;
—$R^{S3}$ is independently —H or saturated aliphatic $C_{1-4}$alkyl;
—$R^{S4}$ is independently —H or saturated aliphatic $C_{1-4}$alkyl;
and wherein -Q is independently selected from:

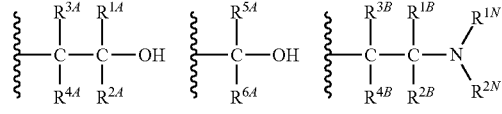

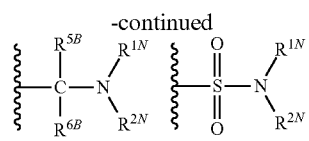

wherein:
each —$R^{1N}$ is independently —H or —$R^{CN}$;
each —$R^{2N}$ is independently —H or —$R^{CN}$;
each —$R^{CN}$ is independently saturated aliphatic $C_{1-4}$alkyl;
or:
—$NR^{1N}R^{2N}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl;
—$R^{1A}$ is independently —H, —$R^C$, or —$R^F$; and
—$R^{2A}$ is independently —H, —$R^C$, or —$R^F$;
or —$R^{1A}$ and —$R^{2A}$ together form a saturated aliphatic $C_{2-4}$alkylene group;
—$R^{3A}$ is independently —$R^C$, —$R^F$, or —$R^J$; and
—$R^{4A}$ is independently —H, —$R^C$, or —$R^F$;
or —$R^{3A}$ and —$R^{4A}$ together form a saturated aliphatic $C_{2-4}$alkylene group;
—$R^{5A}$ is independently —$R^C$ or —$R^F$; and
—$R^{6A}$ is independently —H, —$R^C$, or —$R^F$;
or —$R^{5A}$ and —$R^{6A}$ together form a saturated aliphatic $C_{2-4}$alkylene group;
—$R^{1B}$ is independently —H, —$R^C$, or —$R^F$; and
—$R^{2B}$ is independently —H, —$R^C$, or —$R^F$;
or —$R^{1B}$ and —$R^{2B}$ together form a saturated aliphatic $C_{2-4}$alkylene group;
—$R^{3B}$ is independently —H, —$R^C$, —$R^F$, —OH, or —$R^O$; and
—$R^{4B}$ is independently —H, —$R^C$, or —$R^F$;
or —$R^{3B}$ and —$R^{4B}$ together form a saturated aliphatic $C_{2-4}$alkylene group;
—$R^{5B}$ is independently —H, —$R^C$, or —$R^F$; and
—$R^{6B}$ is independently —H, —$R^C$, or —$R^F$;
or —$R^{5B}$ and —$R^{6B}$ together form a saturated aliphatic $C_{2-4}$alkylene group;
each —$R^C$ is independently saturated aliphatic $C_{1-4}$alkyl;
each —$R^F$ is independently saturated aliphatic $C_{1-4}$fluoroalkyl;
—$R^O$ is independently saturated aliphatic $C_{1-4}$alkyl;
—$R^J$ is independently —$NH_2$, —$NHR^{JN1}$, —$NR^{JN1}_2$, or —$NR^{JN2}R^{JN3}$;
each —$R^{JN1}$ is independently —$R^{J1}$, —$R^{J2}$—OH, —$R^{J2}$—O—$R^{J1}$;
each —$R^{J1}$ is independently saturated aliphatic $C_{1-4}$alkyl;
each —$R^{J2}$— is independently saturated aliphatic $C_{2-4}$alkylene;
—$NR^{JN2}R^{JN3}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl;
and wherein each —$R^X$ is independently:
—F, —Cl, —Br, —I,
—$R^{XX}$,
—OH, —$OR^{XX}$,
—SH, —$SR^{XX}$,
—$CF_3$, —$OCF_3$, —$SCF_3$,
—$NH_2$, —$NHR^{XX}$, —$NR^{XX}_2$, —$NR^{YY}R^{ZZ}$,
—C(=O)$R^{XX}$, —OC(=O)$R^{XX}$,
—C(=O)OH, —C(=O)$OR^{XX}$, —C(=O)NH$_2$, —C(=O)NHR$^{XX}$, —C(=O)NR$^{XX}_2$,
—C(=O)NR$^{YY}$R$^{ZZ}$,
—OC(=O)NH$_2$, —OC(=O)NHR$^{XX}$, —OC(=O)NR$^{XX}_2$,
—OC(=O)NR$^{YY}$R$^{ZZ}$,
—NHC(=O)R$^{XX}$, —NR$^{XX}$C(=O)R$^{XX}$,
—NHC(=O)OR$^{XX}$, —NR$^{XX}$C(=O)OR$^{XX}$,
—NHC(=O)NH$_2$, —NHC(=O)NHR$^{XX}$, —NHC(=O)NR$^{XX}_2$, —NHC(=O)NR$^{YY}$R$^{ZZ}$,
—NR$^{XX}$C(=O)NH$_2$, —NR$^{XX}$C(=O)NHR$^{XX}$, —NR$^{XX}$C(=O)NR$^{XX}_2$, —NR$^{XX}$C(=O)NR$^{YY}$R$^{ZZ}$,
—CN
—NO$_2$,
—S(=O)$_2$NH$_2$, —S(=O)$_2$NHR$^{XX}$, —S(=O)$_2$NR$^{XX}_2$,
—S(=O)$_2$NR$^{YY}$R$^{ZZ}$,
—S(=O)R$^{XX}$, —S(=O)$_2$R$^{XX}$, —OS(=O)$_2$R$^{XX}$,
—S(=O)$_2$OH, or —S(=O)$_2$OR$^{XX}$;

wherein:

each —R$^{XX}$ is independently saturated aliphatic C$_{1-6}$alkyl, phenyl, or benzyl, wherein said phenyl and benzyl are optionally substituted with one or more groups selected from: —F, —Cl, —Br, —I, —CF$_3$, —OCF$_3$, —R$^{XXX}$, —OH, —OR$^{XXX}$, or —SR$^{XXX}$, wherein each —R$^{XXX}$ is independently saturated aliphatic C$_{1-4}$alkyl; and each —NR$^{YY}$R$^{ZZ}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic C$_{1-4}$alkyl.

The Group -A

In one embodiment, -A is independently:

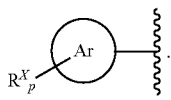

In one embodiment, —Ar is independently phenyl, pyridinyl, or pyrimidinyl.
In one embodiment, —Ar is independently phenyl.
In one embodiment, —Ar is independently pyridinyl.
In one embodiment, —Ar is independently pyridin-2-yl.
In one embodiment, —Ar is independently pyridin-3-yl.
In one embodiment, —Ar is independently pyridin-4-yl.

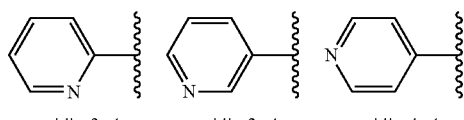

pyridin-2-yl    pyridin-3-yl    pyridin-4-yl

In one embodiment, —Ar is independently pyrimidinyl.
In one embodiment, —Ar is independently pyrimidin-2-yl.
In one embodiment, —Ar is independently pyrimidin-4-yl.
In one embodiment, —Ar is independently pyrimidin-5-yl.

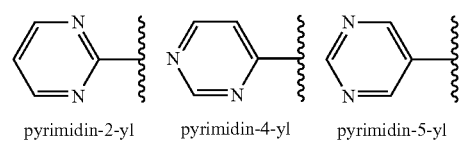

pyrimidin-2-yl    pyrimidin-4-yl    pyrimidin-5-yl

Substituents on —Ar

In one embodiment, p is independently an integer from 0 to 3.
In one embodiment, p is independently an integer from 1 to 3.
In one embodiment, p is independently 0.
In one embodiment, p is independently 1.
In one embodiment, p is independently 2.
In one embodiment, p is independently 3.

The Group -A: Phenyl and Pyridinyl

In one embodiment, -A is independently:

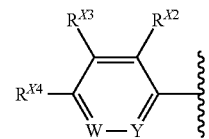

wherein:
=W— is —CH= or —CR$^W$= and —Y= is —CH= or —CR$^Y$=; or
=W— is —CH= or —CR$^W$= and —Y= is —N=; or
=W— is —N= and —Y= is —CH= or —CR$^Y$=;
—R$^W$ is independently saturated aliphatic C$_{1-4}$alkyl;
—R$^Y$ is independently saturated aliphatic C$_{1-4}$alkyl;
—R$^{X2}$ is independently —H or —R$^{X2S}$;
—R$^{X3}$ is independently —H or —R$^{X3S}$;
—R$^{X4}$ is independently —H or —R$^{X4S}$;
—R$^{X2S}$ is independently —R$^X$;
—R$^{X3S}$ is independently —R$^X$; and
—R$^{X4S}$ is independently —R$^X$.

In one embodiment, -A is independently:

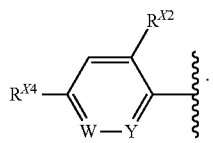

In one embodiment, -A is independently:

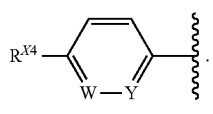

In one embodiment, -A is independently:

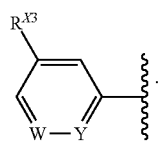

The Group -A: Phenyl and Pyridinyl: the Groups =W— and —Y=

In one embodiment, =W— is —CH= or —CR$^W$= and —Y= is —CH= or —CR$^Y$=.
In one embodiment, =W— is —CH= and —Y= is —CH=, as in, for example:

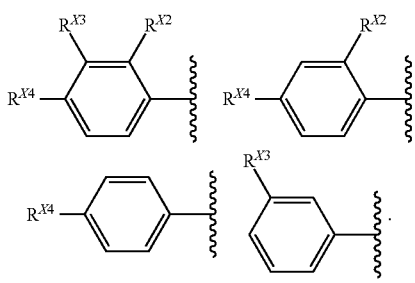

In one embodiment, =W— is —CH= or —CR$^W$= and —Y= is —N=.

In one embodiment, =W— is —CH= and —Y= is —N=, as in, for example:

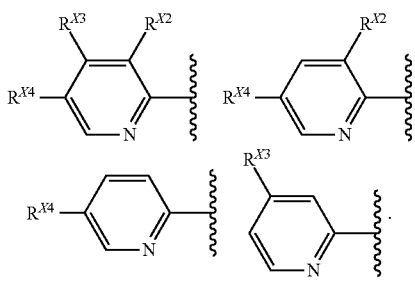

In one embodiment, =W— is —N= and —Y= is —CH= or —CR$^Y$=.

In one embodiment, =W— is —N= and —Y= is —CH=, as in, for example:

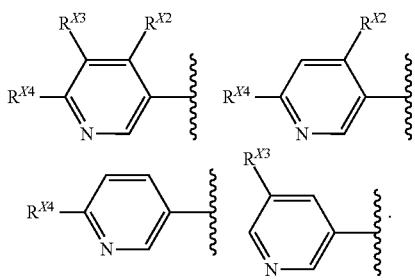

In one embodiment, —R$^W$, if present, is independently saturated aliphatic C$_{1-4}$alkyl.

In one embodiment, —R$^W$, if present, is independently -Me.

In one embodiment, —R$^Y$, if present, is independently saturated aliphatic C$_{1-4}$alkyl.

In one embodiment, —R$^Y$, if present, is independently -Me.

The Group -A: Phenyl: R$^{X2}$ and R$^{X4}$

In one embodiment, -A is independently:

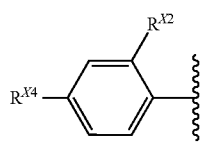

wherein:
—R$^{X2}$ is independently —H or —R$^{X2S}$;
—R$^{X4}$ is independently —H or —R$^{X4S}$;
—R$^{X2S}$ is independently —R$^X$; and
—R$^{X4S}$ is independently —R$^X$.

The Group —R$^{X2}$

In one embodiment, —R$^{X2}$, if present, is independently —H or —R$^{X2S}$.

In one embodiment, —R$^{X2}$, if present, is independently —R$^{X2S}$.

In one embodiment, —R$^{X2}$, if present, is independently —H.

The Group —R$^{X3}$

In one embodiment, —R$^{X3}$, if present, is independently —H or —R$^{X3S}$.

In one embodiment, —R$^{X3}$, if present, is independently —R$^{X3S}$.

In one embodiment, —R$^{X3}$, if present, is independently —H.

The Group —R$^{X4}$

In one embodiment, —R$^{X4}$, if present, is independently —H or —R$^{X4S}$.

In one embodiment, —R$^{X4}$, if present, is independently —R$^{X4S}$.

In one embodiment, —R$^{X4}$, if present, is independently —H.

Leading Phenylene Group

For the avoidance of doubt, the leading phenylene group is the phenylene group that links the group -A, on the left, with the group —S(=O)$_2$N(R$^S$N)(DQ), on the right.

And so, in one embodiment, the leading phenylene group is:

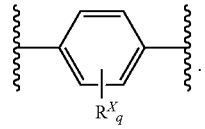

In one embodiment, q is independently an integer from 0 to 3.

In one embodiment, q is independently an integer from 1 to 3.

In one embodiment, q is independently 0.
In one embodiment, q is independently 1.
In one embodiment, q is independently 2.
In one embodiment, the leading phenylene group is:

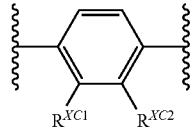

wherein:
—R$^{XC1}$ is independently —H or —R$^X$; and
—R$^{XC2}$ is independently —H or —R$^X$.

In one embodiment:
—R$^{XC1}$ is independently —H or —R$^X$; and
—R$^{XC2}$ is independently —H;

or:
—R$^{XC1}$ is independently —H; and
—R$^{XC2}$ is independently —H or —R$^X$;

or:
- $-R^{XC1}$ is independently $-H$; and
- $-R^{XC2}$ is independently $-H$.

In one embodiment:
- $-R^{XC1}$ is independently $-H$; and
- $-R^{XC2}$ is independently $-H$ or $-R^X$.

In one embodiment:
- $-R^{XC1}$ is independently $-H$ or $-R^X$; and
- $-R^{XC2}$ is independently $-H$.

In one embodiment:
- $-R^{XC1}$ is independently $-H$; and
- $-R^{XC2}$ is independently $-H$.

The Group $-R^X$

In one embodiment, each $-R^X$, if present, is independently:
- $-F, -Cl, -Br, -I$,
- $-R^{XX}$,
- $-OH, -OR^{XX}$,
- $-SH, -SR^{XX}$,
- $-CF_3, -OCF_3, -SCF_3$,
- $-NH_2, -NHR^{XX}, -NR^{XX}_2, -NR^{YY}R^{ZZ}$,
- $-C(=O)R^{XX}, -OC(=O)R^{XX}$,
- $-C(=O)OH, -C(=O)OR^{XX}$,
- $-C(=O)NH_2, -C(=O)NHR^{XX}, -C(=O)NR^{XX}_2, -C(=O)NR^{YY}R^{ZZ}$,
- $-OC(=O)NH_2, -OC(=O)NHR^{XX}, -OC(=O)NR^{XX}_2, -OC(=O)NR^{YY}R^{ZZ}$,
- $-NHC(=O)R^{XX}, -NR^{XX}C(=O)R^{XX}$,
- $-NHC(=O)OR^{XX}, -NR^{XX}C(=O)OR^{XX}$,
- $-NHC(=O)NH_2, -NHC(=O)NHR^{XX}, -NHC(=O)NR^{XX}_2, -NHC(=O)NR^{YY}R^{ZZ}$,
- $-NR^{XX}C(=O)NH_2, -NR^{XX}C(=O)NHR^{XX}, -NR^{XX}C(=O)NR^{XX}_2, -NR^{XX}C(=O)NR^{YY}R^{ZZ}$,
- $-CN$,
- $-NO_2$,
- $-S(=O)_2NH_2, -S(=O)_2NHR^{XX}, -S(=O)_2NR^{XX}_2, -S(=O)_2NR^{YY}R^{ZZ}$,
- $-S(=O)R^{XX}, -S(=O)_2R^{XX}, -OS(=O)_2R^{XX}$,
- $-S(=O)_2OH$, or $-S(=O)_2OR^{XX}$;

wherein:
each $-R^{XX}$ is independently saturated aliphatic $C_{1-6}$alkyl, phenyl, or benzyl, wherein said phenyl and benzyl are optionally substituted with one or more groups selected from: $-F, -Cl, -Br, -I, -CF_3, -OCF_3, -R^{XXX}$, $-OH, -OR^{XXX}$, or $-SR^{XXX}$, wherein each $-R^{XXX}$ is independently saturated aliphatic $C_{1-4}$alkyl; and each $-NR^{YY}R^{ZZ}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl.

In one embodiment, each $-R^X$, if present, is independently:
- $-F, -Cl, -Br, -I$,
- $-R^{XX}$,
- $-OH, -OR^{XX}$,
- $-SH, -SR^{XX}$,
- $-CF_3, -OCF_3, -SCF_3$,
- $-NH_2, -NHR^{XX}, -NR^{XX}_2, -NR^{YY}R^{ZZ}$,
- $-C(=O)R^{XX}, -OC(=O)R^{XX}$,
- $-C(=O)OH, -C(=O)OR^{XX}$,
- $-C(=O)NH_2, -C(=O)NHR^{XX}, -C(=O)NR^{XX}_2, -C(=O)NR^{YY}R^{ZZ}$,
- $-CN$,
- $-NO_2$,
- $-S(=O)_2NH_2, -S(=O)_2NHR^{XX}, -S(=O)_2NR^{XX}_2$, or $-S(=O)_2NR^{YY}R^{ZZ}$.

In one embodiment, each $-R^X$, if present, is independently $-F, -Cl, -Br, -I, -R^{XX}, -OH, -OR^{XX}, -SR^{XX}, -CF_3, -OCF_3, -SCF_3, -C(=O)R^{XX}, -CN$, or $-NO_2$.

In one embodiment, each $-R^X$, if present, is independently $-F, -Cl, -Br, -I, -R^{XX}, -OH, -OR^{XX}, -SR^{XX}, -CF_3, -OCF_3, -SCF_3, -CN$, or $-NO_2$.

In one embodiment, each $-R^X$, if present, is independently $-F, -Cl, -Br, -I, -R^{XX}, -OH, -OR^{XX}, -SR^{XX}, -CF_3, -OCF_3, -CN$, or $-NO_2$.

In one embodiment, each $-R^X$, if present, is independently $-F, -Cl, -Br, -I, -R^{XX}, -OR^{XX}, -SR^{XX}, -CF_3$, or $-OCF_3$.

In one embodiment, each $-R^{XX}$, if present, is independently saturated aliphatic $C_{1-6}$alkyl, phenyl, or benzyl.

In one embodiment, each $-R^{XX}$, if present, is independently saturated aliphatic $C_{1-6}$alkyl.

In one embodiment, each $-R^{XX}$, if present, is independently saturated aliphatic $C_{1-4}$alkyl.

In one embodiment, each $-NR^{YY}R^{ZZ}$, if present, is independently pyrrolidino, imidazolidino, pyrazolidino, piperidino, piperazino, or morpholino, each optionally substituted with one or more groups independently selected from saturated aliphatic $C_{1-4}$alkyl.

In one embodiment, each $-NR^{YY}R^{ZZ}$, if present, is independently pyrrolidino, piperidino, piperazino, or morpholino, each optionally substituted with one or more groups independently selected from saturated aliphatic $C_{1-4}$alkyl.

Substituents on the Leading Phenylene Group

In one embodiment, the leading phenylene group is:

wherein:
- $-R^{XC1}$ is independently $-H$ or $-R^{XCC}$; and
- $-R^{XC2}$ is independently $-H$ or $-R^{XCC}$;

wherein each $-R^{XCC}$ is independently:
- $-F, -Cl, -R^{XCCC}, -OR^{XCCC}, -CF_3$;

wherein each $-R^{XCCC}$ is independently saturated aliphatic $C_{1-4}$alkyl.

In one embodiment:
- $-R^{XC1}$ is independently $-H$ or $-R^{XCC}$; and
- $-R^{XC2}$ is independently $-H$;

or:
- $-R^{XC1}$ is independently $-H$; and
- $-R^{XC2}$ is independently $-H$ or $-R^{XCC}$;

or:
- $-R^{XC1}$ is independently $-H$; and
- $-R^{XC2}$ is independently $-H$.

In one embodiment:
- $-R^{XC1}$ is independently $-H$; and
- $-R^{XC2}$ is independently $-H$ or $-R^{XCC}$.

In one embodiment:
- $-R^{XC1}$ is independently $-H$ or $-R^{XCC}$; and
- $-R^{XC2}$ is independently $-H$.

In one embodiment:
- $-R^{XC1}$ is independently $-H$; and
- $-R^{XC2}$ is independently $-H$.

In one embodiment, each $-R^{XCC}$, if present, is independently $-F, -Cl$, or $-R^{XCCC}$.

In one embodiment, each $-R^{XCC}$, if present, is independently $-R^{XCCC}$.

In one embodiment, each —$R^{XCCC}$, if present, is independently -Me, -Et, -nPr, or -iPr.

In one embodiment, each —$R^{XCCC}$, if present, is independently -Me or -Et.

The Group —$R^{X2S}$

In one embodiment, —$R^{X2S}$, if present, is independently —$R^X$.

In one embodiment, —$R^{X2S}$, if present, is independently —F, —Cl, —Br, —I, —$R^{XA}$, —$OR^{XA}$, —$SR^{XA}$, —$CF_3$, or —$OCF_3$, wherein each —$R^{XA}$ is independently saturated aliphatic $C_{1-4}$alkyl.

In one embodiment, —$R^{X2S}$, if present, is independently —F, —Cl, —Br, —I, —$R^{XA}$, —$OR^{XA}$, —$CF_3$, or —$OCF_3$.

In one embodiment, —$R^{X2S}$, if present, is independently —F, —Cl, —Br, —I, —$CF_3$, or —$OCF_3$.

In one embodiment, —$R^{X2S}$, if present, is independently —F, —Cl, or —$CF_3$.

In one embodiment, —$R^{X2S}$, if present, is independently —F or —Cl.

In one embodiment, —$R^{X2S}$, if present, is independently —F.

In one embodiment, —$R^{X2S}$, if present, is independently —Cl.

The Group —$R^{X3S}$

In one embodiment, —$R^{X3S}$, if present, is independently —$R^X$.

In one embodiment, —$R^{X3S}$, if present, is independently —F, —Cl, —Br, —I, —$R^{XA}$, —$OR^{XA}$, —$SR^{XA}$, —$CF_3$, or —$OCF_3$, wherein each —$R^{XA}$ is independently saturated aliphatic $C_{1-4}$alkyl.

In one embodiment, —$R^{X3S}$, if present, is independently —F, —Cl, —Br, —I, —$R^{XA}$, —$OR^{XA}$, —$CF_3$, or —$OCF_3$.

In one embodiment, —$R^{X3S}$, if present, is independently —F, —Cl, —Br, —I, —$CF_3$, or —$OCF_3$.

In one embodiment, —$R^{X3S}$, if present, is independently —F, —Cl, or —$CF_3$.

In one embodiment, —$R^{X3S}$, if present, is independently —F or —Cl.

In one embodiment, —$R^{X3S}$, if present, is independently —F.

In one embodiment, —$R^{X3S}$, if present, is independently —Cl.

The Group —$R^{X4S}$

In one embodiment, —$R^{X4S}$, if present, is independently —$R^X$.

In one embodiment, —$R^{X4S}$, if present, is independently —F, —Cl, —Br, —I, —$R^{XA}$, —$OR^{XA}$, —$SR^{XA}$, —$CF_3$, or —$OCF_3$, wherein each —$R^{XA}$ is independently saturated aliphatic $C_{1-4}$alkyl.

In one embodiment, —$R^{X4S}$, if present, is independently —F, —Cl, —Br, —I, —$R^{XA}$, —$OR^{XA}$, —$CF_3$, or —$OCF_3$.

In one embodiment, —$R^{X4S}$, if present, is independently —F, —Cl, —Br, —I, —$CF_3$, or —$OCF_3$.

In one embodiment, —$R^{X4S}$, if present, is independently —F, —Cl, or —$CF_3$.

In one embodiment, —$R^{X4S}$, if present, is independently —F or —Cl.

In one embodiment, —$R^{X4S}$, if present, is independently —F.

In one embodiment, —$R^{X4S}$, if present, is independently —Cl.

In one embodiment, —$R^{X2S}$ and —$R^{X4S}$, if present, are each independently —F.

In one embodiment, —$R^{X2S}$ and —$R^{X4S}$, if present, are each independently —Cl.

The Group —$R^{XA}$

In one embodiment, each —$R^{XA}$, if present, is independently saturated aliphatic $C_{1-4}$alkyl.

In one embodiment, each —$R^{XA}$, if present, is independently -Me or -Et.

In one embodiment, each —$R^{XA}$, if present, is independently -Me.

The Group -Q

In one embodiment, -Q is independently selected from:

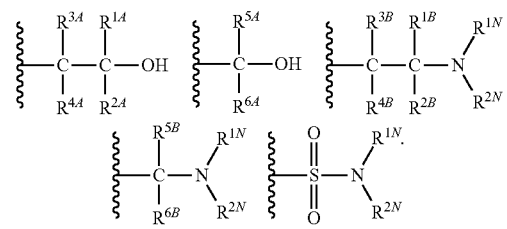

In one embodiment, -Q is independently selected from:

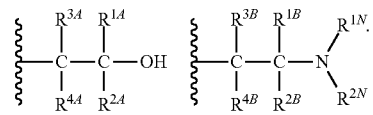

In one embodiment, -Q is independently selected from:

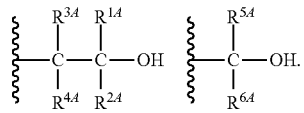

In one embodiment, -Q is independently:

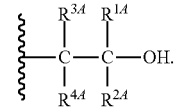

In one embodiment, -Q is independently:

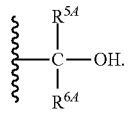

In one embodiment, -Q is independently selected from:

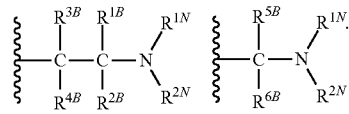

In one embodiment, -Q is independently:

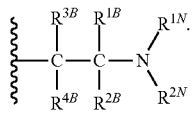

In one embodiment, -Q is independently:

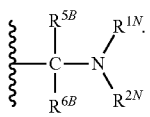

In one embodiment, -Q is independently:

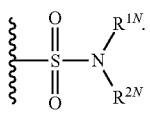

For the avoidance of doubt, where no stereochemistry is indicated, all possible conformations are encompassed.

For example, the group described as —CH(Me)OH or as any of the following:

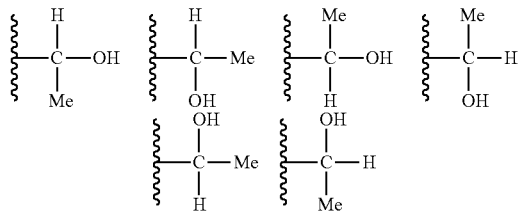

encompasses both stereoisomers:

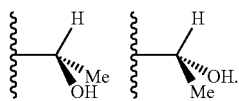

The Groups —$R^{1N}$ and —$R^{2N}$
In one embodiment:
each —$R^{1N}$, if present, is independently —H or —$R^{CN}$;
each —$R^{2N}$, if present, is independently —H or —$R^{CN}$; and
each —$R^{CN}$, if present, is independently saturated aliphatic $C_{1-4}$alkyl;
or:
—$NR^{1N}R^{2N}$, if present, is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl.
In one embodiment:
each —$R^{1N}$, if present, is independently —H or —$R^{CN}$; and
each —$R^{2N}$, if present, is independently —H or —$R^{CN}$.

In one embodiment:
each —$R^{1N}$, if present, is independently —H or —$R^{CN}$; and
each —$R^{2N}$, if present, is independently —H.
In one embodiment:
each —$R^{1N}$, if present, is independently —$R^{CN}$; and
each —$R^{2N}$, if present, is independently —H.
In one embodiment:
each —$R^{1N}$, if present, is independently —$R^{CN}$; and
each —$R^{2N}$, if present, is independently —$R^{CN}$.
In one embodiment:
each —$R^{1N}$, if present, is independently —H; and
each —$R^{2N}$, if present, is independently —H.
In one embodiment, —$NR^{1N}R^{2N}$, if present, is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl.
In one embodiment, —$NR^{1N}R^{2N}$, if present, is independently piperidino, piperazino, or morpholino, each optionally substituted with one or more groups independently selected from saturated aliphatic $C_{1-4}$alkyl.
In one embodiment, —$NR^{1N}R^{2N}$, if present, is independently morpholino.
In one embodiment, each —$R^{CN}$, if present, is independently -Me or -Et.
In one embodiment, each —$R^{CN}$, if present, is independently -Me.
In one embodiment, —$NR^{1N}R^{2N}$, if present, is independently —$NH_2$, —NHMe, —$NMe_2$, —NHEt, —$NEt_2$, pyrrolidino, or morpholino.
In one embodiment, —$NR^{1N}R^{2N}$, if present, is independently —$NH_2$, —NHMe, —$NMe_2$, or morpholino.
The Groups —$R^{1A}$ and —$R^{2A}$
In one embodiment:
—$R^{1A}$, if present, is independently —H, —$R^C$, or —$R^F$; and
—$R^{2A}$, if present, is independently —H, —$R^C$, or —$R^F$;
or —$R^{1A}$ and —$R^{2A}$, if present, together form a saturated aliphatic $C_{2-4}$alkylene group.
In one embodiment:
—$R^{1A}$, if present, is independently —H, —$R^C$, or —$R^F$; and
—$R^{2A}$, if present, is independently —H, —$R^C$, or —$R^F$.
In one embodiment:
—$R^{1A}$, if present, is independently —H or —$R^C$; and
—$R^{2A}$, if present, is independently —H or —$R^C$.
In one embodiment:
—$R^{1A}$, if present, is independently —H or —$R^C$; and
—$R^{2A}$, if present, is independently —H.
In one embodiment:
—$R^{1A}$, if present, is independently —$R^C$; and
—$R^{2A}$, if present, is independently —H.
In one embodiment:
—$R^{1A}$, if present, is independently —$R^C$; and
—$R^{2A}$, if present, is independently —$R^C$.
In one embodiment:
—$R^{1A}$, if present, is independently —H; and
—$R^{2A}$, if present, is independently —H.
In one embodiment, —$R^{1A}$ and —$R^{2A}$, if present, together form a saturated aliphatic $C_{2-4}$alkylene group.
In one embodiment, —$R^{1A}$ and —$R^{2A}$, if present, together form —$CH_2CH_2$—, —$CH_2CH_2CH_2$—, or —$CH_2CH_2CH_2CH_2$—.
In one embodiment, —$R^{1A}$ and —$R^{2A}$, if present, together form —$CH_2CH_2$—.

The Groups —$R^{3A}$ and —$R^{4A}$

In one embodiment:
—$R^{3A}$, if present, is independently —$R^C$, —$R^F$, or —$R^J$; and
—$R^{4A}$, if present, is independently —H, —$R^C$, or —$R^F$;
or —$R^{3A}$ and —$R^{4A}$, if present, together form a saturated aliphatic $C_{2-4}$alkylene group.

In one embodiment:
—$R^{3A}$, if present, is independently —$R^C$ or —$R^J$; and
—$R^{4A}$, if present, is independently —H or —$R^C$.

In one embodiment:
—$R^{3A}$, if present, is independently —$R^J$; and
—$R^{4A}$, if present, is independently —H or —$R^C$.

In one embodiment:
—$R^{3A}$, if present, is independently —$R^J$; and
—$R^{4A}$, if present, is independently —H.

In one embodiment:
—$R^{3A}$, if present, is independently —$R^J$; and
—$R^{4A}$, if present, is independently —$R^C$.

In one embodiment:
—$R^{3A}$, if present, is independently —$R^C$; and
—$R^{4A}$, if present, is independently —H or —$R^C$.

In one embodiment:
—$R^{3A}$, if present, is independently —$R^C$; and
—$R^{4A}$, if present, is independently —H.

In one embodiment:
—$R^{3A}$, if present, is independently —$R^C$; and
—$R^{4A}$, if present, is independently —$R^C$.

In one embodiment, —$R^{3A}$ and —$R^{4A}$, if present, together form a saturated aliphatic $C_{2-4}$alkylene group.

In one embodiment, —$R^{3A}$ and —$R^{4A}$, if present, together form —$CH_2CH_2$—, —$CH_2CH_2CH_2$—, or —$CH_2CH_2CH_2CH_2$—.

In one embodiment, —$R^{3A}$ and —$R^{4A}$, if present, together form —$CH_2CH_2$—.

The Groups —$R^{5A}$ and —$R^{6A}$

In one embodiment:
—$R^{5A}$, if present, is independently —$R^C$ or —$R^F$; and
—$R^{6A}$, if present, is independently —H, —$R^C$, or —$R^F$;
or —$R^{6A}$ and —$R^{6A}$, if present, together form a saturated aliphatic $C_{2-4}$alkylene group.

In one embodiment:
—$R^{5A}$, if present, is independently —$R^C$ or —$R^F$; and
—$R^{6A}$, if present, is independently —H, —$R^C$, or —$R^F$.

In one embodiment:
—$R^{5A}$, if present, is independently —$R^C$; and
—$R^{6A}$, if present, is independently —H or —$R^C$.

In one embodiment:
—$R^{5A}$, if present, is independently —$R^C$; and
—$R^{6A}$, if present, is independently —H.

In one embodiment:
—$R^{5A}$, if present, is independently —$R^C$; and
—$R^{6A}$, if present, is independently —$R^C$.

In one embodiment:
—$R^{5A}$, if present, is independently —$R^F$; and
—$R^{6A}$, if present, is independently —H.

In one embodiment, —$R^{5A}$ and —$R^{6A}$, if present, together form a saturated aliphatic $C_{2-4}$alkylene group.

In one embodiment, —$R^{5A}$ and —$R^{6A}$, if present, together form —$CH_2CH_2$—, —$CH_2CH_2CH_2$—, or —$CH_2CH_2CH_2CH_2$—.

In one embodiment, —$R^{5A}$ and —$R^{6A}$, if present, together form —$CH_2CH_2$—.

The Groups —$R^{1B}$ and —$R^{2B}$

In one embodiment:
—$R^{1B}$, if present, is independently —H, —$R^C$, or —$R^F$; and
—$R^{2B}$, if present, is independently —H, —$R^C$, or —$R^F$;
or —$R^{1B}$ and —$R^{2B}$, if present, together form a saturated aliphatic $C_{2-4}$alkylene group.

In one embodiment:
—$R^{1B}$, if present, is independently —H, —$R^C$, or —$R^F$; and
—$R^{2B}$, if present, is independently —H, —$R^C$, or —$R^F$.

In one embodiment:
—$R^{1B}$, if present, is independently —H or —$R^C$; and
—$R^{2B}$, if present, is independently —H or —$R^C$.

In one embodiment:
—$R^{1B}$, if present, is independently —H or —$R^C$; and
—$R^{2B}$, if present, is independently —H.

In one embodiment:
—$R^{1B}$, if present, is independently —H; and
—$R^{2B}$, if present, is independently —$R^C$.

In one embodiment:
—$R^{1B}$, if present, is independently —$R^C$; and
—$R^{2B}$, if present, is independently —$R^C$.

In one embodiment:
—$R^{1B}$, if present, is independently —H; and
—$R^{2B}$, if present, is independently —H.

In one embodiment, —$R^{1B}$ and —$R^{2B}$, if present, together form a saturated aliphatic $C_{2-4}$alkylene group.

In one embodiment, —$R^{1B}$ and —$R^{2B}$, if present, together form —$CH_2CH_2$—, —$CH_2CH_2CH_2$—, or —$CH_2CH_2CH_2CH_2$—.

In one embodiment, —$R^{1B}$ and —$R^{2B}$, if present, together form —$CH_2CH_2$—.

The Groups —$R^{3B}$ and —$R^{4B}$

In one embodiment:
—$R^{3B}$, if present, is independently —H, —$R^C$, —$R^F$, —OH, or —$OR^O$; and
—$R^{4B}$, if present, is independently —H, —$R^C$, or —$R^F$;
or —$R^{3B}$ and —$R^{4B}$, if present, together form a saturated aliphatic $C_{2-4}$alkylene group.

In one embodiment:
—$R^{3B}$, if present, is independently —H, —$R^C$, —$R^F$, —OH, or —$OR^O$; and
—$R^{4B}$, if present, is independently —H, —$R^C$, or —$R^F$.

In one embodiment:
—$R^{3B}$, if present, is independently —H, —OH, or —$OR^O$; and
—$R^{4B}$, if present, is independently —H or —$R^C$.

In one embodiment:
—$R^{3B}$, if present, is independently —OH or —$OR^O$; and
—$R^{4B}$, if present, is independently —H or —$R^C$.

In one embodiment:
—$R^{3B}$, if present, is independently —OH or —$OR^O$; and
—$R^{4B}$, if present, is independently —H.

In one embodiment:
—$R^{3B}$, if present, is independently —OH; and
—$R^{4B}$, if present, is independently —H.

In one embodiment:
—$R^{3B}$, if present, is independently —H or —$R^C$; and
—$R^{4B}$, if present, is independently —H or —$R^C$.

In one embodiment:
—$R^{3B}$, if present, is independently —H or —$R^C$; and
—$R^{4B}$, if present, is independently —H.

In one embodiment:
—$R^{3B}$, if present, is independently —H; and
—$R^{4B}$, if present, is independently —$R^C$.

In one embodiment:
—$R^{3B}$, if present, is independently —$R^C$; and
—$R^{4B}$, if present, is independently —$R^C$.

In one embodiment:
—$R^{3B}$, if present, is independently —H; and
—$R^{4B}$, if present, is independently —H.
In one embodiment, —$R^{3B}$ and —$R^{4B}$, if present, together form a saturated aliphatic $C_{2-4}$alkylene group.
In one embodiment, —$R^{3B}$ and —$R^{4B}$, if present, together form —$CH_2CH_2$—, —$CH_2CH_2CH_2$—, or —$CH_2CH_2CH_2CH_2$—.
In one embodiment, —$R^{3B}$ and —$R^{4B}$, if present, together form —$CH_2CH_2$—.

The Groups —$R^{5B}$ and —$R^{6B}$
In one embodiment:
—$R^{5B}$, if present, is independently —H, —$R^C$, or —$R^F$; and
—$R^{6B}$, if present, is independently —H, —$R^C$, or —$R^F$; or —$R^{5B}$ and —$R^{6B}$, if present, together form a saturated aliphatic $C_{2-4}$alkylene group.
In one embodiment:
—$R^{5B}$, if present, is independently —H, —$R^C$, or —$R^F$; and
—$R^{6B}$, if present, is independently —H, —$R^C$, or —$R^F$.
In one embodiment:
—$R^{5B}$, if present, is independently —H or —$R^C$; and
—$R^{6B}$, if present, is independently —H or —$R^C$.
In one embodiment:
—$R^{5B}$, if present, is independently —H or —$R^C$; and
—$R^{6B}$, if present, is independently —H.
In one embodiment:
—$R^{5B}$, if present, is independently —H; and
—$R^{6B}$, if present, is independently —$R^C$.
In one embodiment:
—$R^{5B}$, if present, is independently —$R^C$; and
—$R^{6B}$, if present, is independently —$R^C$.
In one embodiment:
—$R^{5B}$, if present, is independently —H; and
—$R^{6B}$, if present, is independently —H.
In one embodiment, —$R^{5B}$ and —$R^{6B}$, if present, together form a saturated aliphatic $C_{2-4}$alkylene group.
In one embodiment, —$R^{5B}$ and —$R^{6B}$, if present, together form —$CH_2CH_2$—, —$CH_2CH_2CH_2$—, or —$CH_2CH_2CH_2CH_2$—.
In one embodiment, —$R^{5B}$ and —$R^{6B}$, if present, together form —$CH_2CH_2$—.

The Group —$R^O$
In one embodiment, —$R^O$, if present, is independently saturated aliphatic $C_{1-4}$alkyl.
In one embodiment, —$R^O$, if present, is independently -Me or -Et.
In one embodiment, —$R^O$, if present, is independently -Me.

The Group —$R^C$
In one embodiment, each —$R^C$, if present, is independently saturated aliphatic $C_{1-4}$alkyl.
In one embodiment, each —$R^C$, if present, is independently -Me or -Et.
In one embodiment, each —$R^C$, if present, is independently -Me.

The Group —$R^F$
In one embodiment, each —$R^F$, if present, is independently saturated aliphatic $C_{1-4}$fluoroalkyl.
In one embodiment, each —$R^F$, if present, is independently —$CF_3$, —$CH_2CF_3$, or —$CH_2CH_2F$.
In one embodiment, each —$R^F$, if present, is independently —$CF_3$.

The Group —$R^J$
In one embodiment, —$R^J$, if present, is independently —$NH_2$, —$NHR^{JN1}$, —$NR^{JN1}{}_2$, or —$NR^{JN2}R^{JN3}$.

In one embodiment, —$R^J$, if present, is independently —$NH_2$, —$NHR^{JN1}$, or —$NR^{JN1}{}_2$.
In one embodiment, —$R^J$, if present, is independently —$NH_2$ or —$NHR^{JN1}$.
In one embodiment, —$R^J$, if present, is independently —$NH_2$.
In one embodiment, —$R^J$, if present, is independently —$NHR^{JN1}$.
In one embodiment, —$R^J$, if present, is independently —$NR^{JN1}{}_2$.
In one embodiment, —$R^J$, if present, is independently —$NR^{JN2}R^{JN3}$.
In one embodiment:
each —$R^{JN1}$, if present, is independently —$R^{J1}$, —$R^{J2}$—OH, —$R^{J2}$—O—$R^{J1}$;
each —$R^{J1}$, if present, is independently saturated aliphatic $C_{1-4}$alkyl; and
each —$R^{J2}$—, if present, is independently saturated aliphatic $C_{2-4}$alkylene.
In one embodiment, each —$R^{JN1}$, if present, is independently —$R^{J1}$.
In one embodiment, each —$R^{J1}$, if present, is independently saturated aliphatic $C_{1-4}$alkyl.
In one embodiment, each —$R^{J1}$, if present, is independently -Me, -Et, or -iPr.
In one embodiment, each —$R^{J1}$, if present, is independently -Me or -Et.
In one embodiment, each —$R^{J1}$, if present, is independently -Me.
In one embodiment, each —$R^{J2}$—, if present, is independently saturated aliphatic $C_{2-4}$alkylene.
In one embodiment, each —$R^{J2}$—, if present, is independently —$CH_2CH_2$— or —$CH_2CH_2CH_2$—.
In one embodiment, each —$R^{J2}$—, if present, is independently —$CH_2CH_2$—.
In one embodiment, each —$R^{JN1}$, if present, is independently saturated aliphatic $C_{1-4}$alkyl.
In one embodiment, each —$R^{JN1}$, if present, is independently -Me, -Et, or -iPr.
In one embodiment, each —$R^{JN1}$, if present, is independently -Me or -Et.
In one embodiment, each —$R^{JN1}$, if present, is independently -Me.
In one embodiment, —$NR^{JN2}R^{JN3}$, if present, is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl.
In one embodiment, —$NR^{JN2}R^{JN3}$, if present, is independently piperidino, piperazino, or morpholino, each optionally substituted with one or more groups independently selected from saturated aliphatic $C_{1-4}$alkyl.
In one embodiment, —$NR^{JN2}R^{JN3}$, if present, is independently morpholino.
In one embodiment, —$R^J$, if present, is independently —$NH_2$, —NHMe, —$NMe_2$, —NHEt, —$NEt_2$, —NH(nPr), —N(nPr)$_2$, —NH(iPr), —N(iPr)$_2$, —NH($CH_2CH_2OH$), —NH($CH_2CH_2OCH_3$), piperidino, piperazino, or morpholino.
In one embodiment, —$R^J$, if present, is independently —$NH_2$, —NHMe, —$NMe_2$, —NHEt, —$NEt_2$, —NH(nPr), —N(nPr)$_2$, —NH(iPr), —N(iPr)$_2$, piperidino, piperazino, or morpholino.
In one embodiment, —$R^J$, if present, is independently —$NH_2$, —NHMe, —$NMe_2$, or morpholino.

In one embodiment, —$R^J$, if present, is independently —$NH_2$, —NHMe, or —$NMe_2$.

The Group -Q: Some Preferred Embodiments

In one embodiment, -Q is independently:
—CH(Me)OH, —C(Me)$_2$OH, —CH(CF$_3$)OH, -(cycloprop-1,1-di-yl)OH,
—CH(NH$_2$)CH$_2$OH, —CH(NHMe)CH$_2$OH, —CH(NMe$_2$)CH$_2$OH,
—CH(NHEt)CH$_2$OH, —CH(NEt$_2$)CH$_2$OH,
—CH(morpholino)CH$_2$OH,
—CH(NHCH$_2$CH$_2$OH)CH$_2$OH, —CH(NHCH$_2$CH$_2$OMe)CH$_2$OH,
—C(Me)(NH$_2$)CH$_2$OH,
—CH$_2$NH$_2$, —CH$_2$NHMe, —CH$_2$NMe$_2$, —CH$_2$NHEt, —CH$_2$NEt$_2$,
—CH$_2$CH$_2$NH$_2$, —CH$_2$CH$_2$NHMe, —CH$_2$CH$_2$NMe$_2$,
—CH(OH)CH$_2$NH$_2$, —CH(OH)CH$_2$NHMe, —CH(OH)CH$_2$NMe$_2$, —CH(OH)CH$_2$(morpholino),
—S(=O)$_2$NH$_2$, or —S(=O)$_2$(pyrrolidino).

In one embodiment, -Q is independently:
—CH(Me)OH, —C(Me)$_2$OH, —CH(CF$_3$)OH, -(cycloprop-1,1-di-yl)OH,
—CH(NH$_2$)CH$_2$OH, —CH(NHMe)CH$_2$OH, —CH(NMe$_2$)CH$_2$OH, —CH(morpholino)CH$_2$OH,
—CH$_2$NH$_2$, —CH$_2$NHMe, —CH$_2$NMe$_2$,
—CH$_2$CH$_2$NH$_2$, —CH$_2$CH$_2$NHMe, —CH$_2$CH$_2$NMe$_2$,
—CH(OH)CH$_2$NH$_2$, —CH(OH)CH$_2$NHMe, —CH(OH)CH$_2$NMe$_2$, —CH(OH)CH$_2$(morpholino), or
—S(=O)$_2$NH$_2$.

In one embodiment, -Q is independently:
—CH(NH$_2$)CH$_2$OH, —CH(NHMe)CH$_2$OH, —CH(NMe$_2$)CH$_2$OH, —CH(NHEt)CH$_2$OH, —CH(NEt$_2$)CH$_2$OH, —CH(morpholino)CH$_2$OH,
—CH(OH)CH$_2$NH$_2$, —CH(OH)CH$_2$NHMe, —CH(OH)CH$_2$NMe$_2$, or —CH(OH)CH$_2$(morpholino).

In one embodiment, -Q is independently:
—CH(NH$_2$)CH$_2$OH, —CH(NHMe)CH$_2$OH, —CH(NMe$_2$)CH$_2$OH, —CH(morpholino)CH$_2$OH,
—CH(OH)CH$_2$NH$_2$, —CH(OH)CH$_2$NHMe, —CH(OH)CH$_2$NMe$_2$, or —CH(OH)CH$_2$(morpholino).

In one embodiment, -Q is independently —CH(Me)OH, —C(Me)$_2$OH, —CH(CF$_3$)OH, or -(cycloprop-1,1-di-yl)OH.

In one embodiment, -Q is independently —CH(NH$_2$)CH$_2$OH, —CH(NHMe)CH$_2$OH, —CH(NMe$_2$)CH$_2$OH, —CH(NHEt)CH$_2$OH, —CH(NEt$_2$)CH$_2$OH, or —CH(morpholino)CH$_2$OH.

In one embodiment, -Q is independently —CH(NH$_2$)CH$_2$OH, —CH(NHMe)CH$_2$OH, —CH(NMe$_2$)CH$_2$OH, or —CH(morpholino)CH$_2$OH.

In one embodiment, -Q is independently —CH$_2$NH$_2$, —CH$_2$NHMe, —CH$_2$NMe$_2$, —CH$_2$NHEt, or —CH$_2$NEt$_2$.

In one embodiment, -Q is independently —CH$_2$NH$_2$, —CH$_2$NHMe, or —CH$_2$NMe$_2$.

In one embodiment, -Q is independently —CH$_2$CH$_2$NH$_2$, —CH$_2$CH$_2$NHMe, —CH$_2$CH$_2$NMe$_2$, —CH$_2$CH$_2$NHEt, or —CH$_2$CH$_2$NEt$_2$.

In one embodiment, -Q is independently —CH$_2$CH$_2$NH$_2$, —CH$_2$CH$_2$NHMe, or —CH$_2$CH$_2$NMe$_2$.

In one embodiment, -Q is independently —CH(OH)CH$_2$NH$_2$, —CH(OH)CH$_2$NHMe, —CH(OH)CH$_2$NMe$_2$, —CH(OH)CH$_2$(morpholino).

In one embodiment, -Q is independently —S(=O)$_2$NH$_2$, or —S(=O)$_2$(pyrrolidino).

In one embodiment, -Q is independently —S(=O)NH$_2$.

The Group —$R^{SN}$

In one embodiment, —$R^{SN}$ is independently —H or saturated aliphatic $C_{1-4}$alkyl.

In one embodiment, —$R^{SN}$ is independently —H, -Me, or -Et.

In one embodiment, —$R^{SN}$ is independently —H.

The Groups —$R^{S1}$, —$R^{S2}$, —$R^{S3}$, and —$R^{S4}$

In one embodiment, —$R^{S1}$ is independently —H or saturated aliphatic $C_{1-4}$alkyl.

In one embodiment, —$R^{S1}$ is independently —H or -Me.

In one embodiment, —$R^{S1}$ is independently —H.

In one embodiment, —$R^{S1}$ is independently -Me.

In one embodiment, —$R^{S2}$ is independently —H or saturated aliphatic $C_{1-4}$alkyl.

In one embodiment, —$R^{S2}$ is independently —H.

In one embodiment, —$R^{S3}$ is independently —H or saturated aliphatic $C_{1-4}$alkyl.

In one embodiment, —$R^{S3}$ is independently —H.

In one embodiment, —$R^{S4}$ is independently —H or saturated aliphatic $C_{1-4}$alkyl.

In one embodiment, —$R^{S4}$ is independently —H.

In one embodiment:
—$R^{S1}$ is independently —H or saturated aliphatic $C_{1-4}$alkyl;
—$R^{S2}$ is independently —H;
—$R^{S3}$ is independently —H; and
—$R^{S4}$ is independently —H.

In one embodiment:
—$R^{S1}$ is independently —H or -Me;
—$R^{S2}$ is independently —H;
—$R^{S3}$ is independently —H; and
—$R^{S4}$ is independently —H.

In one embodiment:
—$R^{S1}$ is independently —H;
—$R^{S2}$ is independently —H;
—$R^{S3}$ is independently —H; and
—$R^{S4}$ is independently —H.

Some Preferred Combinations—1

In one preferred embodiment:
-A is independently:

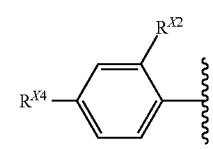

-Q is independently:

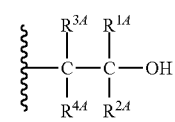

—$R^{1A}$ is independently —H;
—$R^{2A}$ is independently —H;
—$R^{3A}$ is independently —$R^J$; and
—$R^{4A}$ is independently —H.

In one preferred embodiment:
-A is independently:

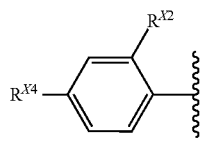

-Q is independently:

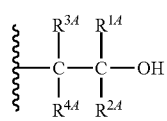

—$R^{1A}$ is independently —H;
—$R^{2A}$ is independently —H;
—$R^{3A}$ is independently —$R^{J}$;
—$R^{4A}$ is independently —H;
—$R^{X2}$ is independently —F or —Cl;
—$R^{X4}$ is independently —F or —Cl; and
—$R^{SN}$ is independently —H or -Me.

In other preferred embodiments, additionally, —$R^{J}$ is independently —$NH_2$, —NHMe, —$NMe_2$, —NHEt, —$NEt_2$, —NH(nPr), —$N(nPr)_2$, —NH(iPr), —$N(iPr)_2$, piperidino, piperazino, or morpholino.

In other preferred embodiments, additionally, —$R^{J}$ is independently —$NH_2$, —NHMe, —$NMe_2$, or morpholino.

In other preferred embodiments, additionally, —$R^{J}$ is independently —$NH_2$, —NHMe, or —$NMe_2$.

In other preferred embodiments, additionally, —$R^{J}$ is independently —NHMe.

In other preferred embodiments, additionally, —$R^{X2}$ is independently —F and —$R^{X4}$ is independently —F.

In other preferred embodiments, additionally, —$R^{SN}$ is independently —H.

For example, in one embodiment, the compound is selected from compounds of the following formula, and pharmaceutically acceptable salts, hydrates, and solvates thereof:

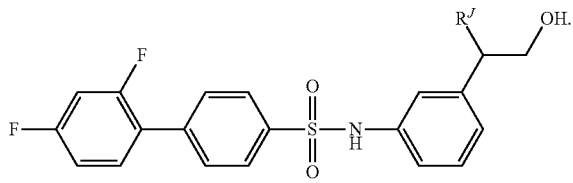

Some Preferred Combinations—2
In one preferred embodiment:
-A is independently:

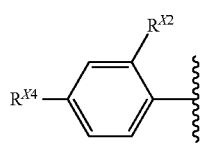

-Q is independently:

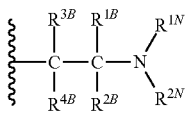

—$R^{1B}$ is independently —H;
—$R^{2B}$ is independently —H;
—$R^{3B}$ is independently —OH or —$OR^{O}$; and
—$R^{4B}$ is independently —H.

In one preferred embodiment:
-A is independently:

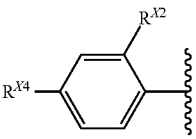

-Q is independently:

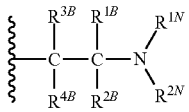

—$R^{1B}$ is independently —H;
—$R^{2B}$ is independently —H;
—$R^{3B}$ is independently —OH; and
—$R^{4B}$ is independently —H.

In one preferred embodiment:
-A is independently:

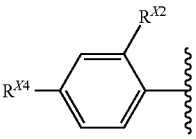

-Q is independently:

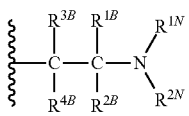

—$R^{1B}$ is independently —H;
—$R^{2B}$ is independently —H;
—$R^{3B}$ is independently —OH;
—$R^{4B}$ is independently —H;
each —$R^{1N}$ is independently —H or —$R^{CN}$; and
each —$R^{2N}$ is independently —H or —$R^{CN}$.

In one preferred embodiment:
-A is independently:

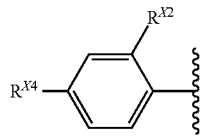

-Q is independently:

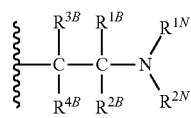

—$R^{1B}$ is independently —H;
—$R^{2B}$ is independently —H;
—$R^{3B}$ is independently —OH;
—$R^{4B}$ is independently —H;
each —$R^{1N}$ is independently —H or —$R^{CN}$;
each —$R^{2N}$ is independently —H or —$R^{CN}$;
—$R^{X2}$ is independently —F or —Cl;
—$R^{X4}$ is independently —F or —Cl; and
—$R^{SN}$ is independently —H or -Me.

In one preferred embodiment:
-A is independently:

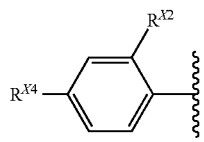

-Q is independently:

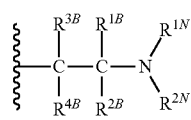

—$R^{1B}$ is independently —H;
—$R^{2B}$ is independently —H;
—$R^{3B}$ is independently —OH;
—$R^{4B}$ is independently —H;
each —$R^{1N}$ is independently —H or -Me;
each —$R^{2N}$ is independently —H or -Me;
—$R^{X2}$ is independently —F or —Cl;
—$R^{X4}$ is independently —F or —Cl; and
—$R^{SN}$ is independently —H or -Me.

Molecular Weight

In one embodiment, the APSAP compound has a molecular weight of from 338 to 1200.

In one embodiment, the bottom of range is 350, 375, 400, 425, 450, 500.

In one embodiment, the top of range is 1100, 1000, 900, 800, 700, or 600.

In one embodiment, the range is from 375 to 700.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., -A, —Ar, —$R^X$, p, q, —$R^{SN}$, —$R^{S1}$, —$R^{S2}$, —$R^{S3}$, —$R^{S4}$, -Q, —$R^{1A}$, —$R^{2A}$, —$R^{3A}$, —$R^{4A}$, —$R^{5A}$, —$R^{6A}$, —$R^{1B}$, —$R^{2B}$, —$R^{3B}$, —$R^{4B}$, —$R^{5B}$, —$R^{6B}$, —$R^{1N}$, —$R^{2N}$, —$R^{CN}$, —$NR^{1N}R^{2N}$, —$R^C$, $R^F$, —$R^J$, —$R^O$, —$R^{JN1}$, —$R^{J1}$, —$R^{J2}$, —$NR^{JN2}R^{JN3}$, —$R^{XX}$, —$NR^{YY}R^{ZZ}$, —$R^{XXX}$, =W—, —Y=, —$R^W$, —$R^Y$, —$R^{X2}$, —$R^{X3}$, —$R^{X4}$, $R^{X2S}$, —$R^{X3S}$, —$R^{X4S}$, —$R^{X4}$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

Specific Embodiments

In one embodiment, the compounds are selected from compounds of the following formulae and pharmaceutically acceptable salts, hydrates, and solvates thereof:

| Compound No. | Structure |
|---|---|
| ABD707 | 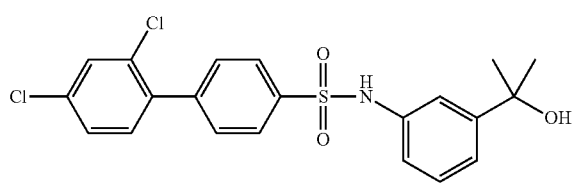 |

| Compound No. | Structure |
|---|---|
| ABD708 | 2',4'-dichloro-N-(3-(1-hydroxyethyl)phenyl)-[1,1'-biphenyl]-4-sulfonamide |
| ABD709 | 2',4'-dichloro-N-(3-(1-hydroxycyclopropyl)phenyl)-[1,1'-biphenyl]-4-sulfonamide |
| ABD766 | 2',4'-dichloro-N-(3-(2,2,2-trifluoro-1-hydroxyethyl)phenyl)-[1,1'-biphenyl]-4-sulfonamide |

In one embodiment, the compounds are selected from compounds of the following formulae and pharmaceutically acceptable salts, hydrates, and solvates thereof:

| Compound No. | Structure |
|---|---|
| ABD723 | 2',4'-dichloro-N-(3-((methylamino)methyl)phenyl)-[1,1'-biphenyl]-4-sulfonamide |
| ABD724 | 2',4'-dichloro-N-(3-((dimethylamino)methyl)phenyl)-[1,1'-biphenyl]-4-sulfonamide |
| ABD788 | N-(3-(aminomethyl)phenyl)-2',4'-difluoro-[1,1'-biphenyl]-4-sulfonamide |
| ABD829 | 2',4'-difluoro-N-(3-((methylamino)methyl)phenyl)-[1,1'-biphenyl]-4-sulfonamide |

-continued
| Compound No. | Structure |
|---|---|
| ABD830 | 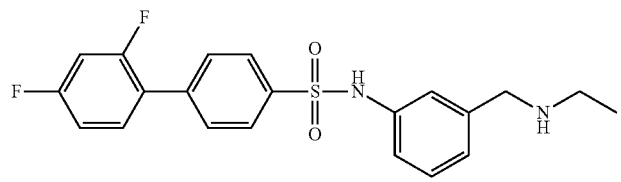 |
| ABD831 | 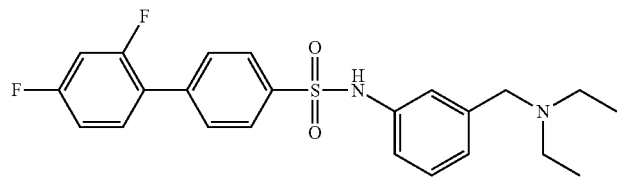 |
| ABD833 | 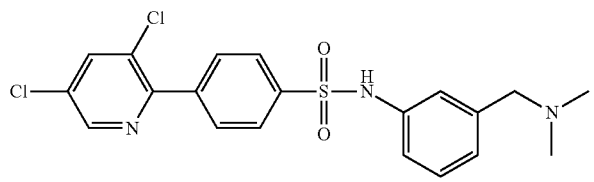 |
| ABD834 | 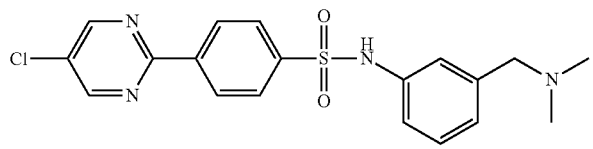 |
| ABD860 | 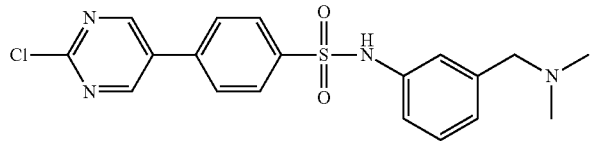 |
| ABD880 | 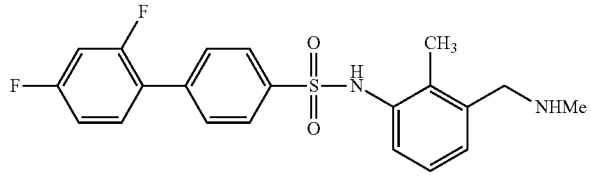 |
| ABD881 | 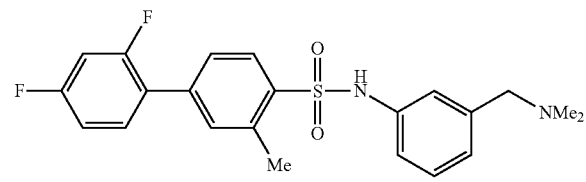 |
| ABD882 | 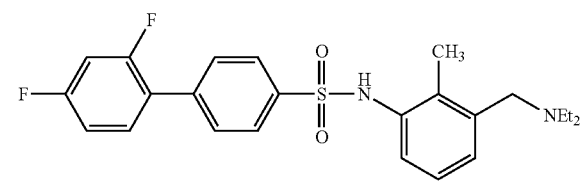 |

In one embodiment, the compounds are selected from compounds of the following formulae and pharmaceutically acceptable salts, hydrates, and solvates thereof:

| Compound No. | Structure |
|---|---|
| ABD782 | 2',4'-difluorobiphenyl-4-sulfonamide linked to 3-(2-amino-1-hydroxyethyl)phenyl |
| ABD783 | 2',4'-difluorobiphenyl-4-sulfonamide linked to 3-(1-hydroxy-2-(methylamino)ethyl)phenyl |
| ABD784 | 2',4'-difluorobiphenyl-4-sulfonamide linked to 3-(2-(dimethylamino)-1-hydroxyethyl)phenyl |
| ABD785 | 2',4'-difluorobiphenyl-4-sulfonamide linked to 3-(1-hydroxy-2-morpholinoethyl)phenyl |
| ABD832 | 2',4'-difluorobiphenyl-4-sulfonamide linked to 3-(2-(methylamino)ethyl)phenyl |

In one embodiment, the compounds are selected from compounds of the following formulae and pharmaceutically acceptable salts, hydrates, and solvates thereof:

| Compound No. | Structure |
|---|---|
| ABD789 | 2',4'-difluorobiphenyl-4-sulfonamide linked to 3-(2-hydroxy-1-(methylamino)ethyl)phenyl |
| ABD790 | 2',4'-difluorobiphenyl-4-sulfonamide linked to 3-(1-amino-2-hydroxyethyl)phenyl |

-continued

| Compound No. | Structure |
|---|---|
| ABD791 | 2,4-difluoro-biphenyl-4'-sulfonamide linked to 3-[1-(dimethylamino)-2-hydroxyethyl]phenyl |
| ABD792 | 2,4-difluoro-biphenyl-4'-sulfonamide linked to 3-[1-(morpholin-4-yl)-2-hydroxyethyl]phenyl |
| ABD810 | 2,4-difluoro-biphenyl-4'-sulfonamide linked to 3-[(1S)-1-(methylamino)-2-hydroxyethyl]phenyl |
| ABD811 | 2,4-difluoro-biphenyl-4'-sulfonamide linked to 3-[(1R)-1-(methylamino)-2-hydroxyethyl]phenyl |
| ABD850 | 3,5-dichloropyridin-2-yl-phenyl-sulfonamide linked to 3-[1-(methylamino)-2-hydroxyethyl]phenyl |
| ABD851 | 4-chloro-2-fluoro-biphenyl-4'-sulfonamide linked to 3-[1-(methylamino)-2-hydroxyethyl]phenyl |
| ABD852 | 5-chloropyridin-2-yl-phenyl-sulfonamide linked to 3-[1-(methylamino)-2-hydroxyethyl]phenyl |
| ABD853 | 2,4-dichloro-biphenyl-4'-sulfonamide linked to 3-[1-(methylamino)-2-hydroxyethyl]phenyl |

| Compound No. | Structure |
|---|---|
| ABD854 | 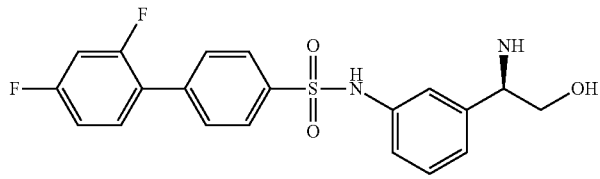 |
| ABD855 | 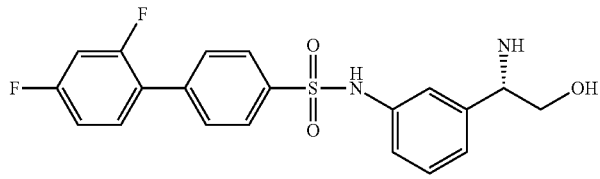 |
| ABD857 | 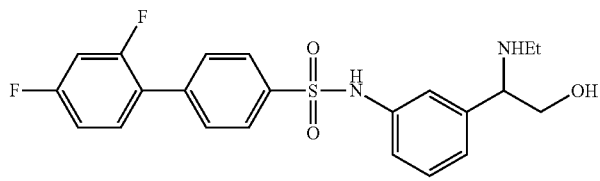 |
| ABD858 | 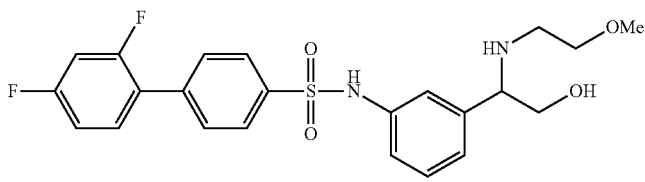 |
| ABD859 | 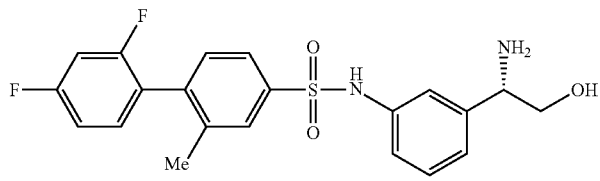 |
| ABD862 | 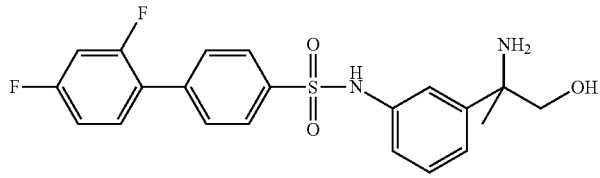 |
| ABD885 | 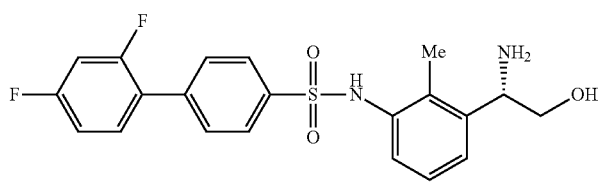 |

In one embodiment, the compounds are selected from compounds of the following formulae and pharmaceutically acceptable salts, hydrates, and solvates thereof:
| Compound No. | Structure |
|---|---|
| ABD751 | 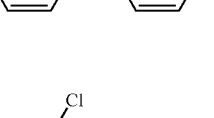 |
| ABD758 | 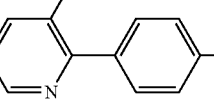 |
| ABD760 | 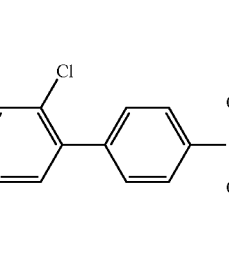 |
| ABD805 | 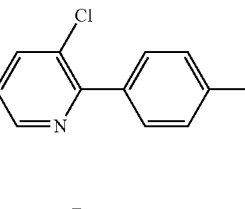 |
| ABD866 | 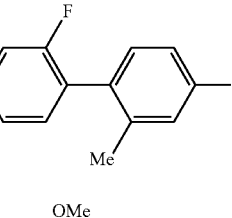 |
| ABD867 | 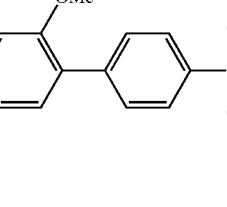 |
| ABD869 | 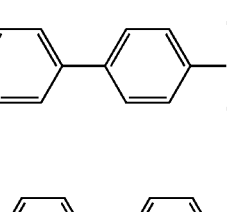 |
| ABD870 | 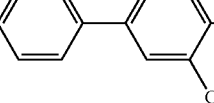 |

-continued

| Compound No. | Structure |
|---|---|
| ABD871 | Me-biphenyl-SO2-NH-phenyl-SO2NH2 |
| ABD872 | 3,5-bis(CF3)-phenyl-(2-Cl-phenyl)-SO2-NH-phenyl-SO2NH2 |
| ABD873 | 3,4-difluoro-biphenyl-SO2-NH-phenyl-SO2NH2 |
| ABD874 | 2-Cl-biphenyl-SO2-NH-phenyl-SO2NH2 |
| ABD875 | 2,4-difluoro-phenyl-(3-Me-phenyl)-SO2-NH-phenyl-SO2NH2 |
| ABD879 | biphenyl-SO2-NH-phenyl-SO2NH2 |

Chirality

In some embodiments (for example, according to the choices for —$R^{1A}$ and —$R^{2A}$; the choices for —$R^{3A}$ and —$R^{4A}$; the choices for —$R^{5A}$ and —$R^{6A}$; the choices for —$R^{1B}$ and —$R^{2B}$; the choices for —$R^{3B}$ and —$R^{4B}$; the choices for —$R^{5B}$ and —$R^{6B}$), the compound may have one or more chiral centres.

The chiral centre, or each chiral centre, if more than one is present, is independently in the R-configuration or the S-configuration.

If no configuration is indicated, then both configurations are encompassed.

Substantially Purified Forms

One aspect of the present invention pertains to APSAP compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

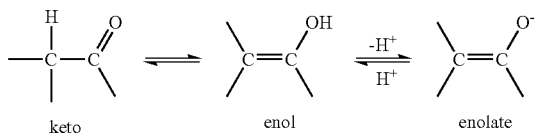

keto    enol    enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperizine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemical Synthesis

Methods for the chemical synthesis of APSAP compounds of the present invention are described herein. These and/or other well-known methods may be modified and/or adapted in known ways in order to facilitate the synthesis of additional APSAP compounds of the present invention.

In one approach, an appropriate biphenyl compound is prepared from a boronic acid and bromobenzene via a Suzuki coupling, for example, as described by O'Brien et al., 2000.

The biphenyl is sulfonylated using chlorosulfonic acid to give the corresponding sulfonic acid. The acid is then reacted with thionyl chloride to give the corresponding aryl sulfonyl chloride. Finally the sulfonyl chloride is coupled with an amine to give the corresponding sulfonamide. An example of such a method is shown in the following scheme.

Scheme 1

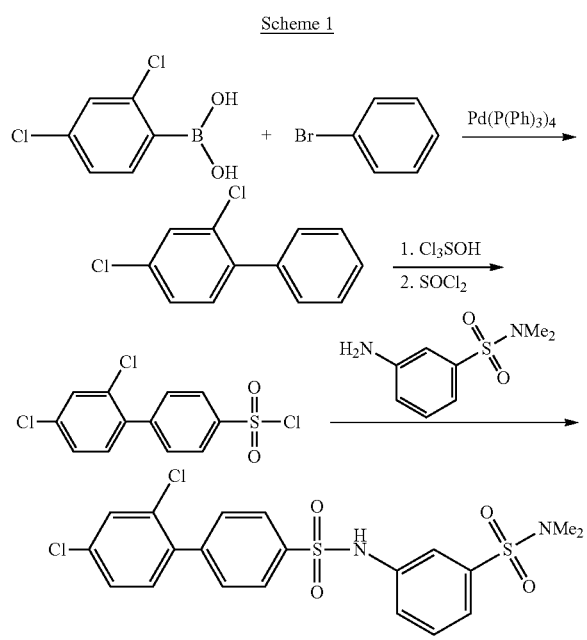

In another approach, the sulfonamide can be formed first, from a suitable bromobenzene sulfonyl chloride and amine and the biphenyl compound then prepared by similar Suzuki methodology. An example of such a method is shown in the following scheme.

Scheme 2

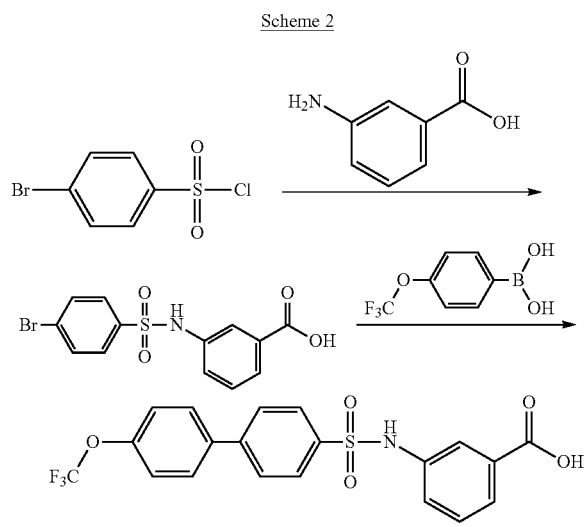

In another approach, the carboxylic acid can be replaced by an amide, by chlorination of the acid followed by coupling with the desired amine. For example the acid can be chlorinated by reflux with thionyl chloride or oxalyl chloride in a solvent such as toluene or DCM, followed by coupling with ammonia or methylamine in a solvent such as THF. An example of such a method is shown in the following scheme.

Scheme 3

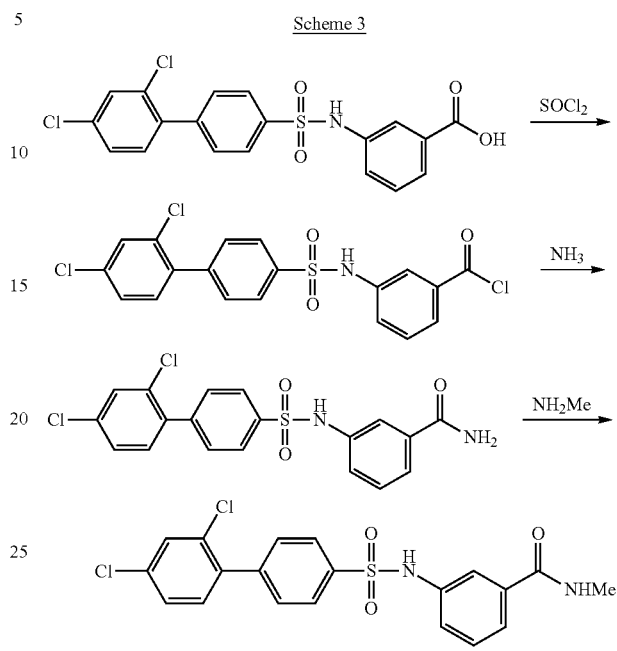

In another approach, the amide is reduced to the corresponding amine by reaction with a suitable reducing agent. For example, the amide can be reduced by lithium aluminium hydride in a solvent such as THF. An example of such a method is shown in the following scheme.

Scheme 4

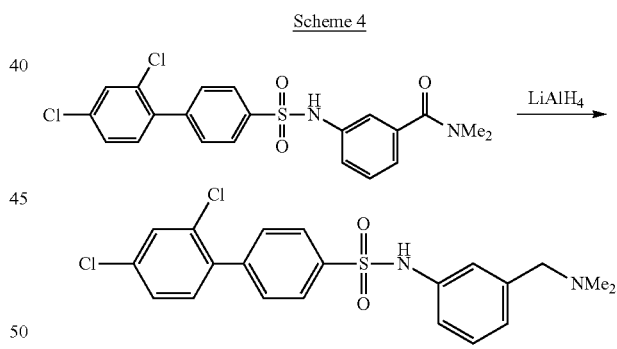

In another approach, the amino group is prepared by reduction of the corresponding cyanophenyl derivative, for example, with a reducing agent such as lithium aluminium hydride in a solvent such as THF. An example of such a method is shown in the following scheme.

Scheme 5

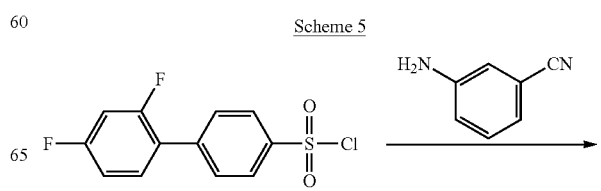

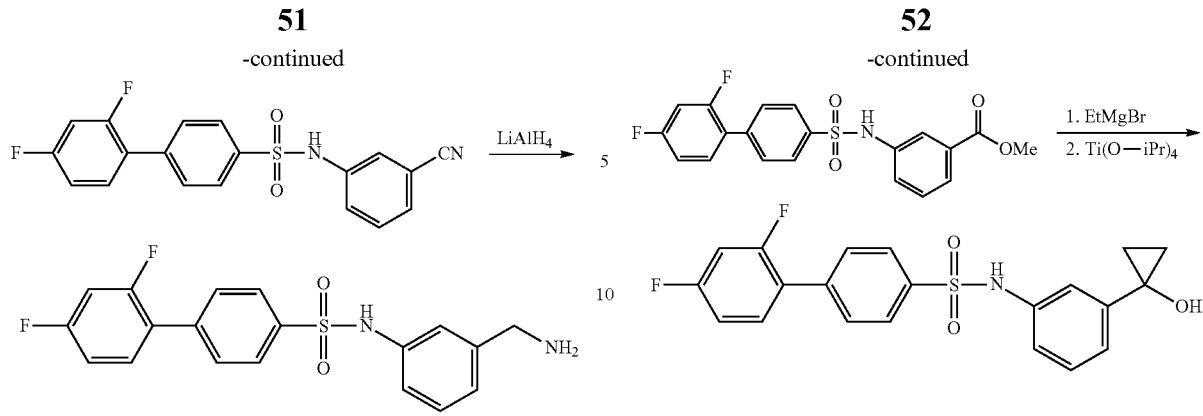

In another approach, further substitutions may be made on a benzyl alcohol, by nucleophilic attack on an acetophenone derivative. This may be done, for example, with a reducing agent such as sodium borohydride in a solvent such as methanol, or with a Grignard reagent such as methyl magnesium bromide, in a solvent such as THF. An example of such a method is shown in the following scheme.

In another approach, the benzyl alcohol can be selectively oxidised to give the aldehyde, and then further substituted by reaction with an appropriate nucleophile. For example, the aldehyde can be prepared by oxidation of the benzyl alcohol with Dess-Martin periodinane (1,1,1-triacetoxy-1,1-dihydro-1,2-benzoiododoxol-3-(1H)-one) in a solvent such as DCM, and then reacted with (trifluoromethyl)trimethyl silane to give a trifluoromethyl substituted benzyl alcohol. An example of such a method is shown in the following scheme.

Scheme 6

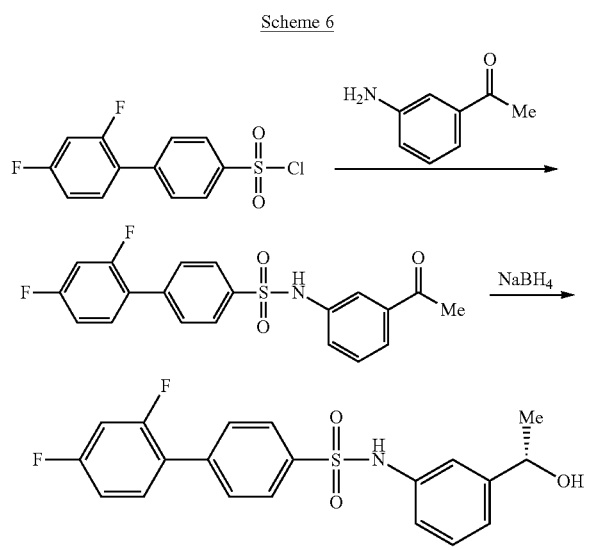

Scheme 8

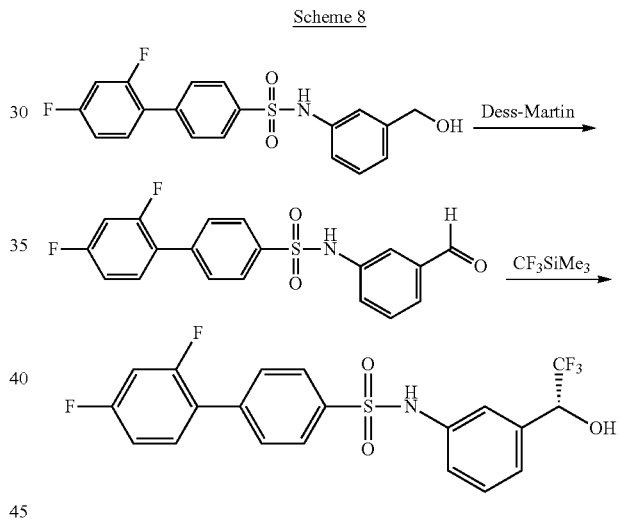

In another approach, further substitutions may be made on a benzyl alcohol, by nucleophilic attack on a carboxylic ester derivative and subsequent cyclisation. This may be done, for example, with a Grignard reagent such as ethyl magnesium bromide in a solvent such as THF, followed by cyclisation with a reagent such as titanium isopropoxide (Sharpless epoxidation) in a solvent such as THF. An example of such a method is shown in the following scheme.

In another approach, a range of amino-substituted benzyl alcohols and hydroxyl-substituted benzylamines can be prepared by nucleophilic attack on an epoxide. For example, the epoxide can be prepared from the corresponding alkene by reaction with a peroxide, such as m-chloroperoxybenzoic acid, in a solvent such as DCM. The epoxide can then be further reacted with an amine, for example ammonia, methylamine or ethylamine, in a solvent such as methanol. This methodology gives a mixture of ring-opening positions and two different regioisomers, which can be separated by column chromatography or HPLC. An example of such a method is shown in the following scheme.

Scheme 7

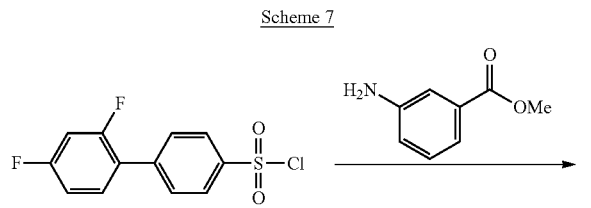

Scheme 9

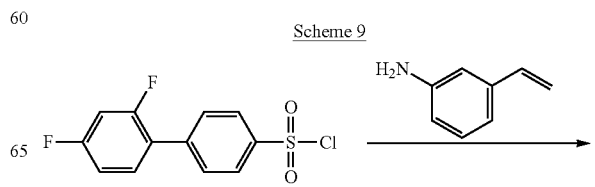

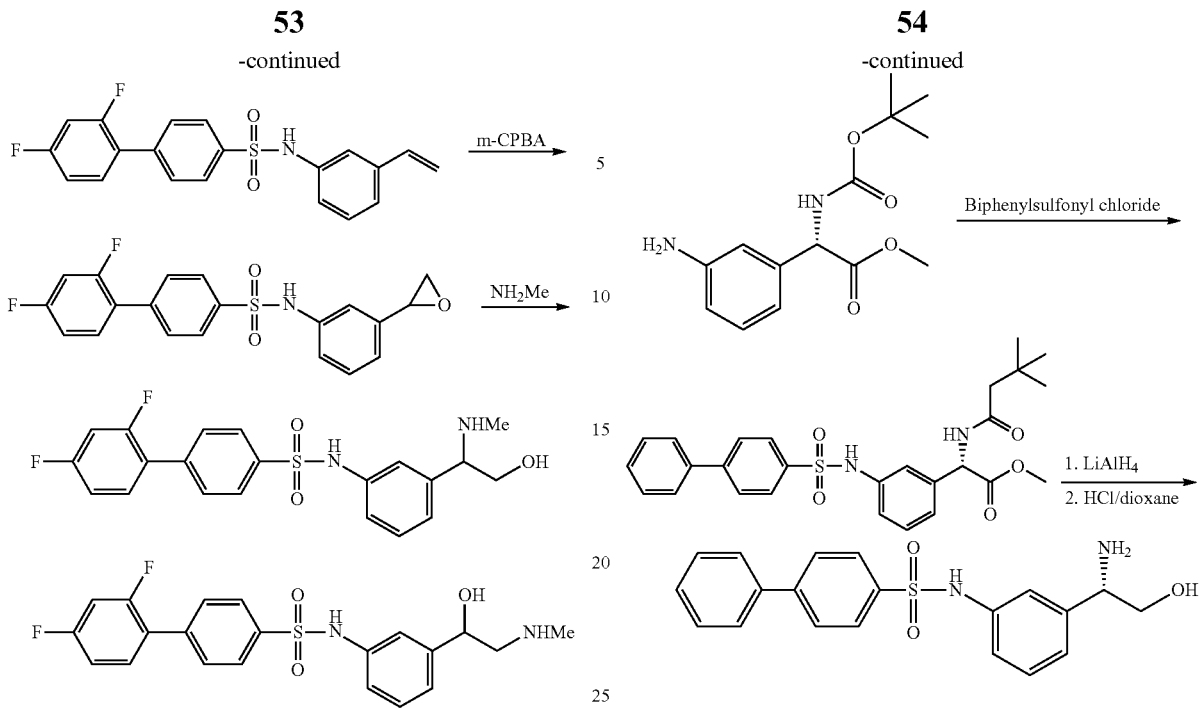

In another approach, the separate stereoisomers generated by such a reaction as shown above in Scheme 9 can be prepared directly using chiral starting materials, for example (R) or (S)-methyl phenylglycine. A nitro group can be introduced, by reaction with nitric acid, and then hydrogenated to give the desired aniline, which may then be coupled with an appropriately substituted phenylsulfonyl chloride as previously described. Then finally, the methyl ester can be reduced and the amide hydrolysed, to give the free alcohol and amine respectively. An example of such a method is shown in the following scheme.

Scheme 10

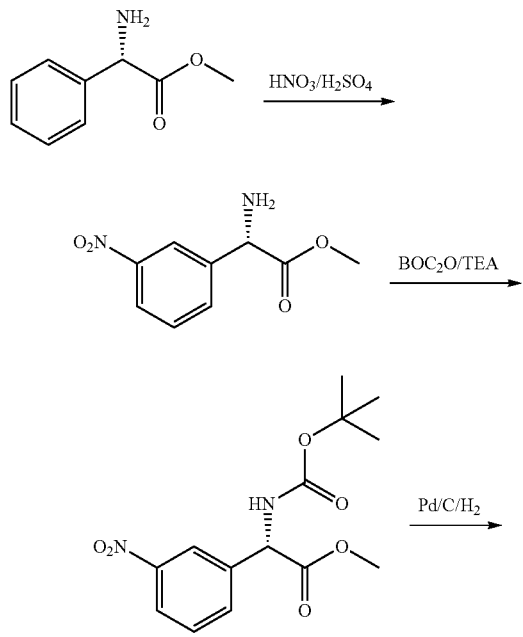

In another approach, a methyl group can be introduced onto the primary amine, by use of the desired chiral phenyloxazolidinone starting material. Reduction of the carbonyl leads to ring opening and the formation of an N-methyl derivative whilst retaining chirality. The required aromatic amine can again be introduced by nitration and reduction as described in Scheme 10, whilst the aliphatic amine is protected by re-cyclisation. Coupling with the required biphenylsulfonyl chloride and ring opening can then be used to give the final N-methyl derivative. For example, (R)-4-phenyloxazolidin-2-one can be reduced with LiAlH$_4$, nitrated with HNO$_3$/H$_2$SO$_4$, protected as a cyclic intermediate by reaction with carbonyl diimidazole, reduced and coupled as described in Scheme 10 and finally hydrolysed with LiOH to give the free alcohol and amine. An example of such a method is shown in the following scheme.

Scheme 11

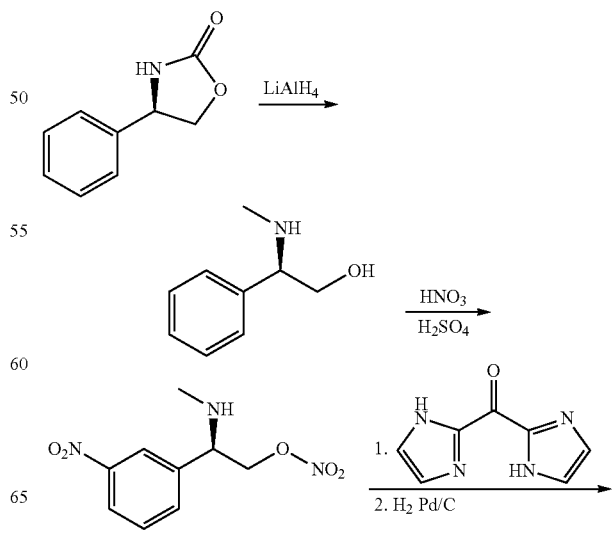

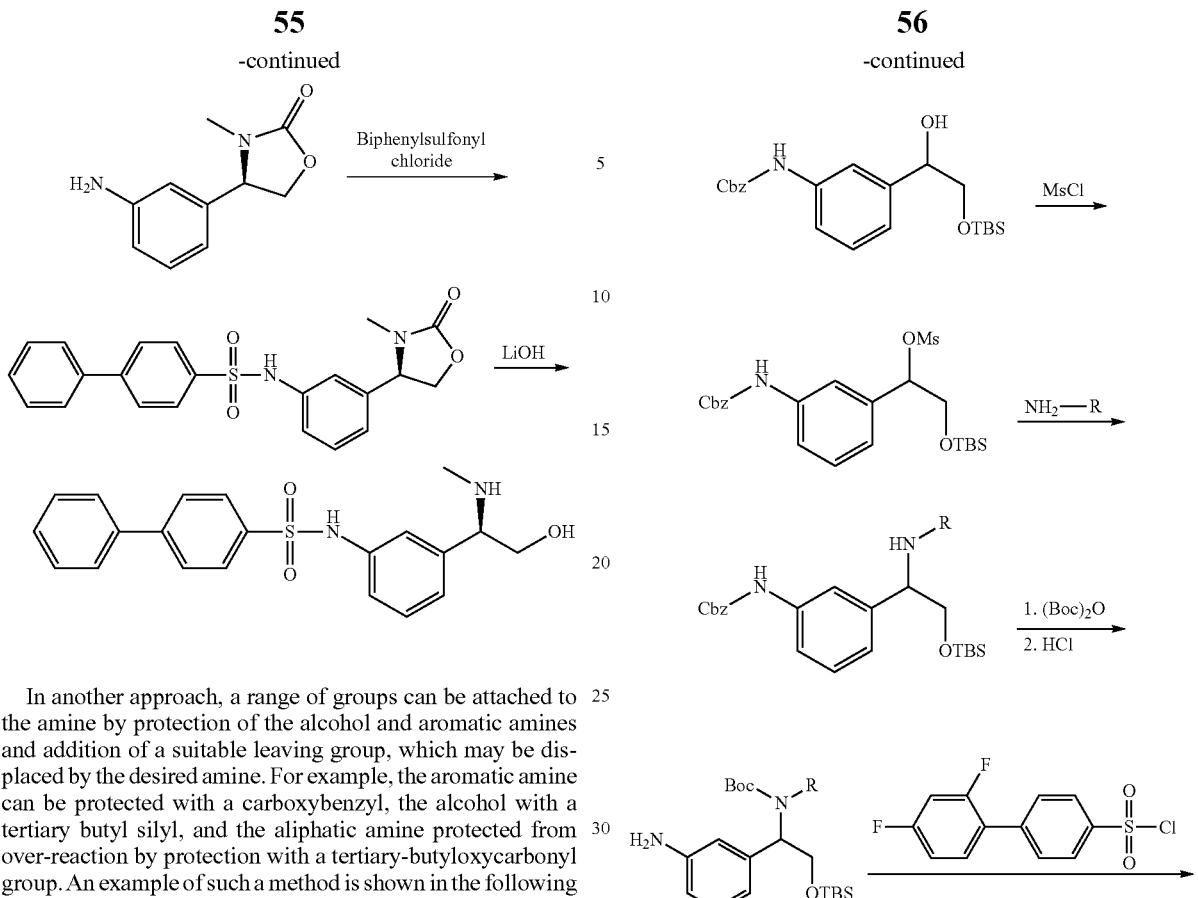

In another approach, a range of groups can be attached to the amine by protection of the alcohol and aromatic amines and addition of a suitable leaving group, which may be displaced by the desired amine. For example, the aromatic amine can be protected with a carboxybenzyl, the alcohol with a tertiary butyl silyl, and the aliphatic amine protected from over-reaction by protection with a tertiary-butyloxycarbonyl group. An example of such a method is shown in the following scheme.

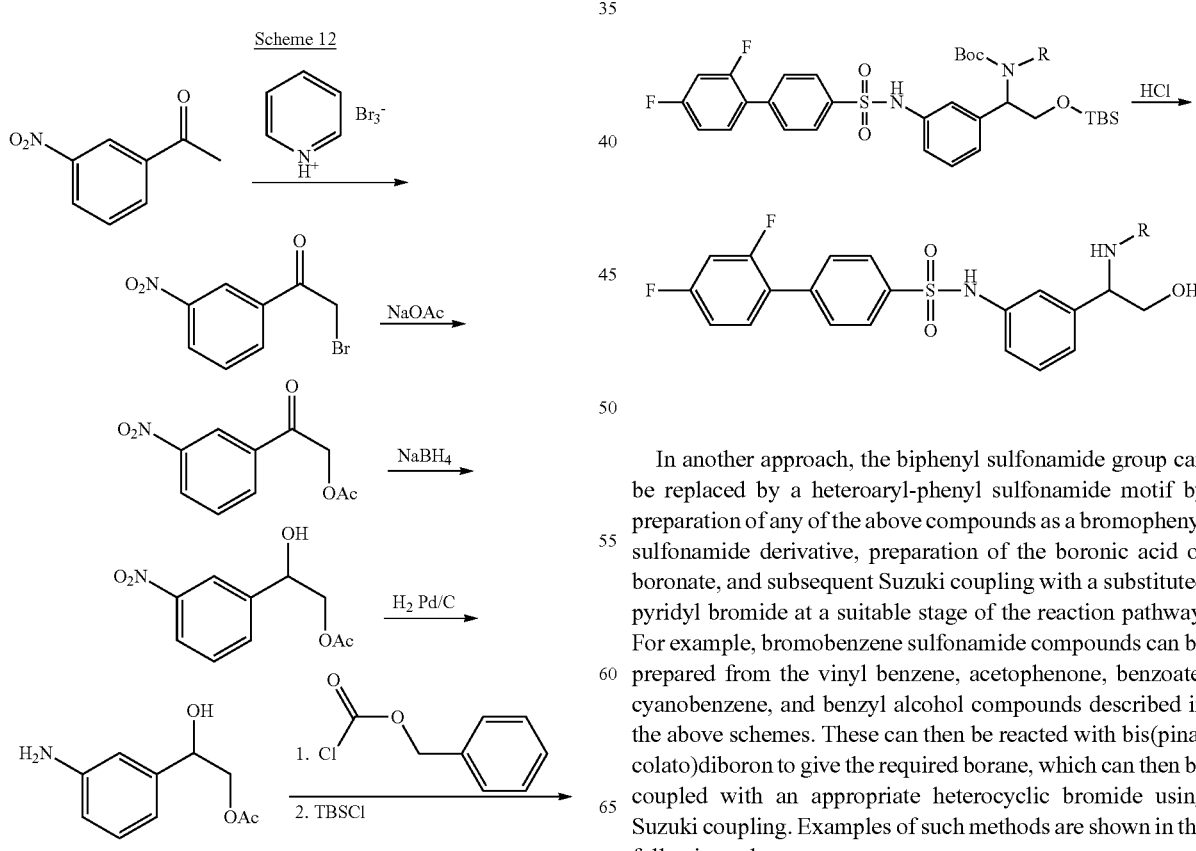

In another approach, the biphenyl sulfonamide group can be replaced by a heteroaryl-phenyl sulfonamide motif by preparation of any of the above compounds as a bromophenyl sulfonamide derivative, preparation of the boronic acid or boronate, and subsequent Suzuki coupling with a substituted pyridyl bromide at a suitable stage of the reaction pathway. For example, bromobenzene sulfonamide compounds can be prepared from the vinyl benzene, acetophenone, benzoate, cyanobenzene, and benzyl alcohol compounds described in the above schemes. These can then be reacted with bis(pinacolato)diboron to give the required borane, which can then be coupled with an appropriate heterocyclic bromide using Suzuki coupling. Examples of such methods are shown in the following schemes.

Scheme 13
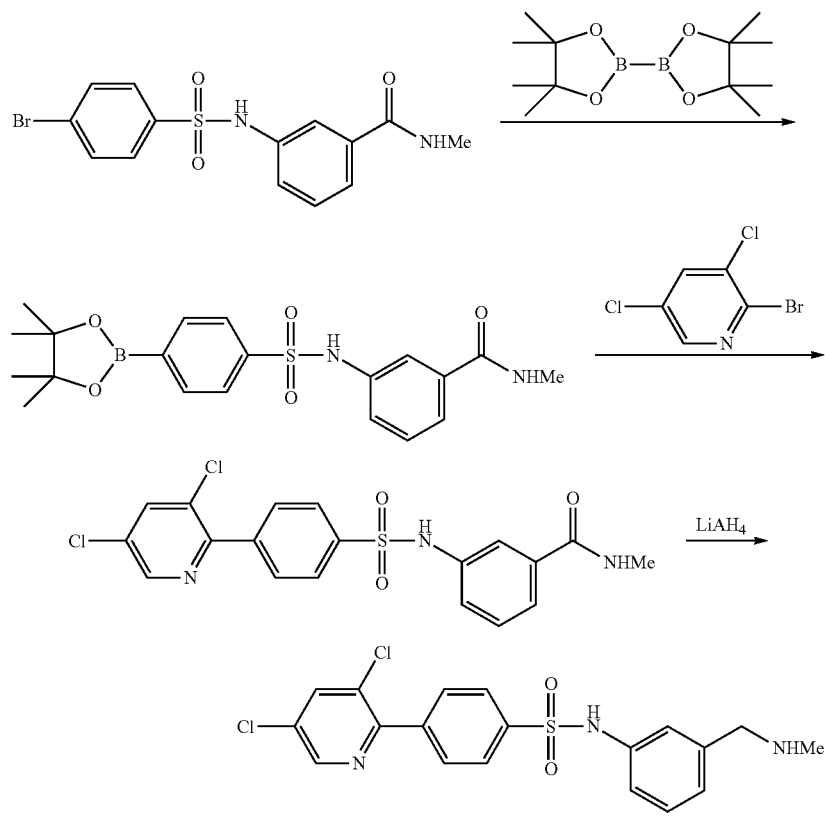
Scheme 14
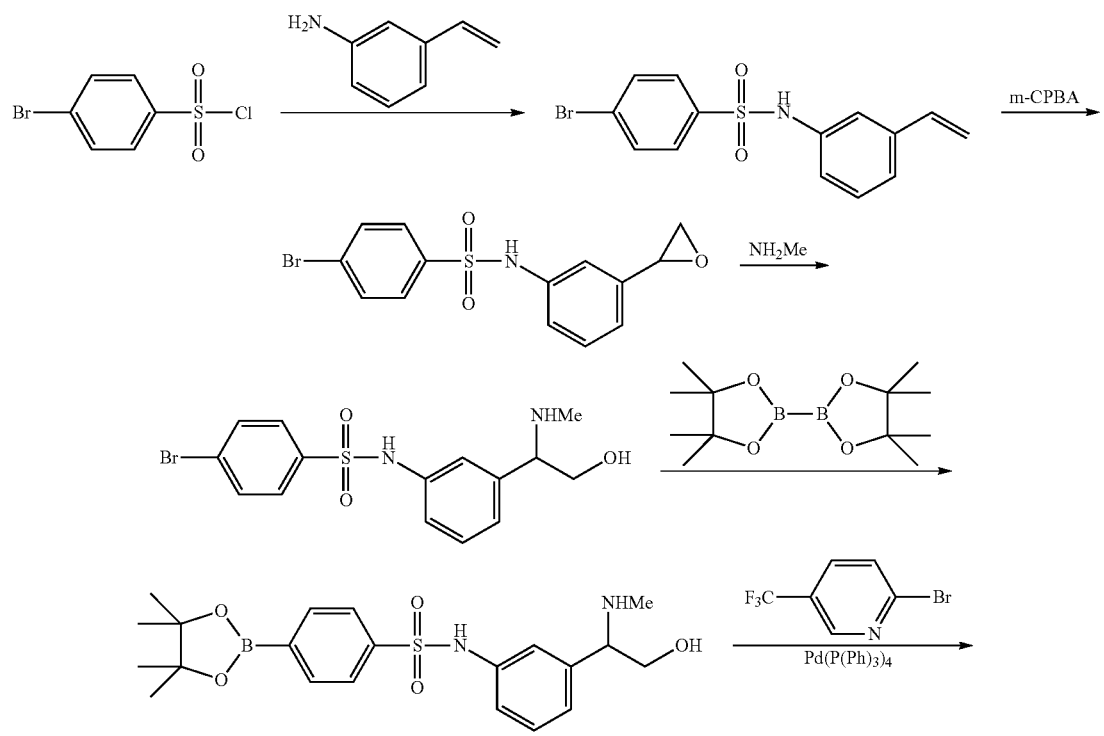

-continued

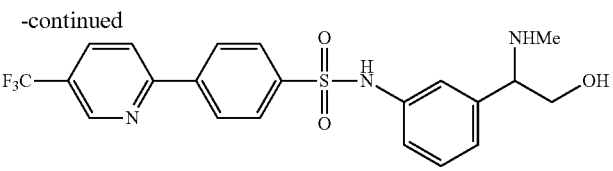

In another approach, a range of substituents can be introduced onto the phenyl rings, by use of the appropriate starting material. For example, a substituted aniline can be reacted with a substituted bromobenzene sulfonyl chloride, which may in turn be coupled with the required boronic acid, to give the desired final substitution pattern. An example of such a method is shown in the following scheme.

Scheme 15

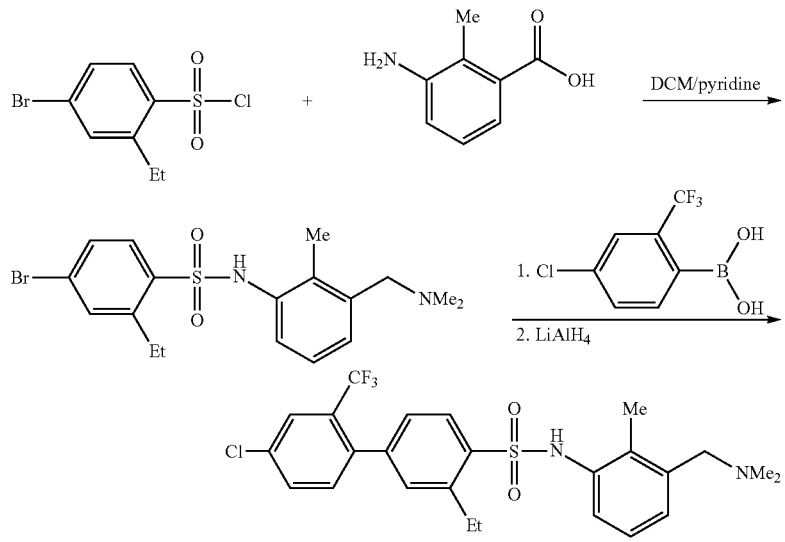

Compositions

One aspect of the present invention pertains to a composition (e.g., a pharmaceutical composition) comprising an APSAP compound, as described herein, and a pharmaceutically acceptable carrier, diluent, or excipient.

Another aspect of the present invention pertains to a method of preparing a composition (e.g., a pharmaceutical composition) comprising admixing an APSAP compound, as described herein, and a pharmaceutically acceptable carrier, diluent, or excipient.

Uses

The APSAP compounds described herein are believed to be anti-inflammatory agents, which may act by blockade or modification of pro-inflammatory signalling pathways (for example those mediated by TNFα signalling and NFκB or AP-1 activation) and thus may prevent inflammation or suppress autoimmune responses or offer protection against joint destruction and other effects of chronic inflammatory disease.

The APSAP compounds described herein are also believed to be anti-resorptive agents, which may act by blockade or modification of pathways that lead to excessive osteoclast activity (for example those mediated by RANKL, TNFα, and IL-1 signalling and NFκB activation) and thereby protect against the bone loss seen in osteoporosis and many chronic inflammatory conditions.

Thus, the APSAP compounds described herein are believed to be useful in the treatment of inflammation and/or joint destruction and/or bone loss.

Thus, the APSAP compounds described herein are believed to be useful in the treatment of disorders mediated by excessive and/or inappropriate and/or prolonged activation of the immune system.

Thus, the APSAP compounds described herein are believed to be useful in the treatment of, inflammatory and autoimmune disorders, for example, rheumatoid arthritis, psoriasis, psoriatic arthritis, chronic obstructive pulmonary disease (COPD), atherosclerosis, inflammatory bowel disease, ankylosing spondylitis, and the like.

Thus, the APSAP compounds described herein are believed to be useful in the treatment of disorders associated with bone loss, such as bone loss associated with excessive osteoclast activation in rheumatoid arthritis, osteoporosis, cancer-associated bone disease, Paget's disease and the like.

Thus, the APSAP compounds described herein are believed to be useful in the treatment of haematological malignancies, e.g., multiple myeloma, leukaemia, or lymphoma (e.g., non-Hodgkin Lymphoma), e.g., haematological malignancies, multiple myeloma, leukaemia, or lymphoma (e.g., non-Hodgkin Lymphoma) associated with activation of NFκB, with aberrant NFκB signalling, or with inflammation.

Thus, the APSAP compounds described herein are believed to be useful in the treatment of solid tumour cancers, e.g., cancer of the bladder, breast cancer (female and/or male), colon cancer, kidney cancer, lung cancer, pancreatic cancer, prostate cancer, brain cancer, skin cancer, thyroid cancer, or melanoma, e.g., solid tumour cancers, cancer of the bladder, breast cancer (female and/or male), colon cancer, kidney cancer, lung cancer, pancreatic cancer, prostate cancer, brain cancer, skin cancer, thyroid cancer, and melanoma associated with activation of NFκB, with aberrant NFκB signalling, or with inflammation.

Thus, the APSAP compounds described herein are believed to be useful in the treatment of a haematological malignancy, e.g., T-cell lymphoblastic lymphoma, mantle cell lymphoma, or acute lymphoblastic leukemia, e.g., a haematological malignancy, T-cell lymphoblastic lymphoma, mantle cell lymphoma, or acute lymphoblastic leukemia associated with inactivation or impairment of caspase induction or with aberrant caspase signalling, e.g., alone, or in combination with, and to augment the efficacy of, radiotherapy or chemotherapy.

Thus, the APSAP compounds described herein are believed to be useful in the treatment of a solid tumour cancer, e.g., renal cell carcinoma, breast cancer (female and/or male), gastric cancer, prostate cancer, colon cancer or basal cell ameloblastoma, e.g., a solid tumour cancer, e.g., renal cell carcinoma, breast cancer (female and/or male), gastric cancer, prostate cancer, colon cancer, or basal cell ameloblastoma associated with inactivation or impairment of caspase induction or with aberrant caspase signalling, e.g., alone or in combination with, and to augment the efficacy of, radiotherapy or chemotherapy.

Use in Methods of Inhibition

One aspect of the invention pertains to a method of inhibiting an inflammatory response, in vitro or in vivo, comprising contacting an immune system component with an effective amount of an APSAP compound, as described herein.

One aspect of the invention pertains to a method of inhibiting cellular and/or molecular pathways leading to joint destruction, in vitro or in vivo, comprising contacting cells associated with an immune response with a therapeutically-effective amount of an APSAP compound, as described herein.

One aspect of the invention pertains to a method of inhibiting osteoclast survival, formation, and/or activity, in vitro or in vivo, comprising contacting an osteoclast with an effective amount of an APSAP compound, as described herein.

One aspect of the invention pertains to a method of inhibiting bone resorption, in vitro or in vivo, comprising contacting cells in the bone microenvironment with a therapeutically-effective amount of an APSAP compound, as described herein.

The term "immune system component," as used herein, relates to, but is not restricted to, cells such as macrophages, T-cells, B-cells, NK-cells, monocytes, neutrophils, dendritic cells, lymphocytes, leukocytes, granulocytes, antigen-presenting cells, and other cells of the haematopoietic lineage including osteoclasts.

The term "cells in the bone microenvironment," as used herein, pertains to cells such as osteoblasts, osteoclasts, osteocytes, and bone marrow stromal cells, which are located in close proximity to bone (e.g., within one hundred micrometers of the bone surface).

Use in Methods of Therapy

Another aspect of the present invention pertains to an APSAP compound, as described herein, for use in a method of treatment of the human or animal body by therapy.

Use in the Manufacture of Medicaments

Another aspect of the present invention pertains to use of an APSAP compound, as described herein, in the manufacture of a medicament for use in treatment.

In one embodiment, the medicament comprises the APSAP compound.

Methods of Treatment

Another aspect of the present invention pertains to a method of treatment comprising administering to a patient in need of treatment a therapeutically effective amount of an APSAP compound, as described herein, preferably in the form of a pharmaceutical composition.

Diseases and Disorders

In one embodiment, the treatment is treatment of an inflammatory disorder or an autoimmune disorder.

In one embodiment, the treatment is treatment of a disorder associated with inflammation and/or activation of the immune system.

In one embodiment, the treatment is treatment of a disorder mediated by excessive and/or inappropriate and/or prolonged activation of the immune system.

In one embodiment, the treatment is treatment of inflammation.

In one embodiment, the treatment is treatment of a disorder associated with inflammation or activation of the immune system.

In one embodiment, the treatment is treatment of rheumatoid arthritis.

In one embodiment, the treatment is treatment of psoriasis.

In one embodiment, the treatment is treatment of psoriatic arthritis.

In one embodiment, the treatment is treatment of chronic obstructive pulmonary disease (COPD).

In one embodiment, the treatment is treatment of atherosclerosis.

In one embodiment, the treatment is treatment of ankylosing spondylitis.

In one embodiment, the treatment is treatment of inflammatory bowel disease.

In one embodiment, the treatment is prevention of an immune response leading to organ or graft rejection following transplant.

In one embodiment, the treatment is treatment of a tumour which over expresses TNFα, IL-1, RANKL, or NFκB, or in which inhibition of TNFα, IL-1, RANKL, or NFκB facilitates or improves the action of cytotoxic tumouricidal agents.

In one embodiment, the treatment is treatment of a haematological malignancy, e.g., multiple myeloma, leukaemia, or lymphoma (e.g., non-Hodgkin Lymphoma), e.g., a haematological malignancy, multiple myeloma, leukaemia, or lymphoma (e.g., non-Hodgkin Lymphoma) associated with activation of NFκB, with aberrant NFκB signalling, or with inflammation, e.g., alone, or in combination with, and to augment the efficacy of, radiotherapy or chemotherapy.

In one embodiment, the treatment is treatment of a solid tumour cancer, e.g., cancer of the bladder, breast cancer (female and/or male), colon cancer, kidney cancer, lung cancer, pancreatic cancer, prostate cancer, brain cancer, skin cancer, thyroid cancer, or melanoma, e.g., a solid tumour cancer, cancer of the bladder, breast cancer (female and/or male), colon cancer, kidney cancer, lung cancer, pancreatic cancer, prostate cancer, brain cancer, skin cancer, thyroid cancer, and melanoma associated with activation of NFκB, with aberrant NFκB signalling, or with inflammation, e.g., alone, or in combination with, and to augment the efficacy of, radiotherapy or chemotherapy.

In one embodiment, the treatment is treatment of a haematological malignancy, e.g., T-cell lymphoblastic lymphoma, mantle cell lymphoma, or acute lymphoblastic leukemia, e.g., a haematological malignancy, T-cell lymphoblastic lymphoma, mantle cell lymphoma, or acute lymphoblastic leukemia associated with inactivation or impairment of caspase induction or with aberrant caspase signalling, e.g., alone or in combination with, and to augment the efficacy of, radiotherapy or chemotherapy.

In one embodiment, the treatment is treatment of a solid tumour cancer, e.g., renal cell carcinoma, breast cancer (female and/or male), gastric cancer, prostate cancer, colon cancer, or basal cell ameloblastoma, e.g., a solid tumour cancer, e.g., renal cell carcinoma, breast cancer (female and/or male), gastric cancer, prostate cancer, colon cancer, or basal cell ameloblastoma associated with inactivation or impairment of caspase induction or with aberrant caspase signalling, e.g., alone, or in combination with, and to augment the efficacy of, radiotherapy or chemotherapy.

In one embodiment, the treatment is part of treatment by combination therapy, e.g., in combination with, and to augment the efficacy of, radiotherapy or chemotherapy.

In one embodiment, the treatment is treatment of a disease or disorder selected from: diseases having an inflammatory or autoimmune component, including asthma, atherosclerosis, allergic diseases, such as atopy, allergic rhinitis, atopic dermatitis, anaphylaxis, allergic bronchopulmonary aspergillosis, and hypersensitivity pneumonitis (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; autoimmune disorders, including, but not limited to, type I diabetes and associated complications, multiple sclerosis, arthritis, systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, experimental allergic encephalomyelitis, autoimmune polyneuritis, pemphigus and other bullous diseases, rheumatic carditis, Goodpasture's syndrome, postcardiotomy syndrome, Sjogren's syndrome, polymyositis, dermatomyositis, and scleroderma; disease states resulting from inappropriate inflammation, either local or systemic, for example, irritable or inflammatory bowel syndrome (Mazzucchelli et al., 1996, *J. Pathol.*, Vol. 178, p. 201), skin diseases such as lichen planus, delayed type hypersensitivity, chronic pulmonary inflammation, e.g., pulmonary alveolitis and pulmonary granuloma, gingival inflammation or other periodontal disease, and osseous inflammation associated with lesions of endodontic origin (Volejnikova et al., 1997, *Am. J. Pathol.*, Vol. 150, p. 1711), hypersensitivity lung diseases such as hypersensitivity pneumonitis (Sugiyama et al., 1995, *Eur. Respir. J.*, Vol. 8, p. 1084), and inflammation related to histamine release from basophils (Dvorak et al., 1996, *J. Allergy Clin. Immunol.*, Vol. 98, p. 355), such as hay fever, histamine release from mast cells (Galli et al., 1989, *Ciba Foundation Symposium*, Vol. 147, p. 53), or mast cell tumours, types of type 1 hypersensitivity reactions (anaphylaxis, skin allergy, hives, gout, allergic rhinitis, and allergic gastroenteritis); ulcerative colitis or Crohn's disease; TNFα induced polycystic kidney disease (Xiaogang Li et al., 2008, *Nature Medicine*, Vol. 14(8), p. 863); or Cryopyrin-Associated Periodic Syndromes, including Muckle-Wells Syndrome.

In one embodiment, the treatment is treatment of a disorder mediated by osteoclasts.

In one embodiment, the treatment is treatment of a disorder characterised by excessive bone resorption.

In one embodiment, the treatment is treatment of bone loss.

In one embodiment, the treatment is treatment of bone loss associated with inflammation.

In one embodiment, the treatment is treatment of bone loss not associated with inflammation.

In one embodiment, the treatment is treatment of bone loss associated with excessive osteoclast activation.

In one embodiment, the treatment is treatment of joint destruction.

In one embodiment, the treatment is treatment of joint destruction associated with inflammation.

In one embodiment, the treatment is treatment of joint destruction associated with excessive osteoclast activation.

In one embodiment, the treatment is treatment of bone loss associated with rheumatoid arthritis, osteoporosis, cancer-associated bone disease, or Paget's disease of bone.

In one embodiment, the treatment is treatment of rheumatoid arthritis, osteoporosis, cancer-associated bone disease, or Paget's disease of bone.

In one embodiment, the treatment is treatment of neoplasia of bones, whether as a primary tumour or as metastases, including but not limited to, osteosarcoma and osteoma (Zheng et al., 1998, *J. Cell Biochem.*, Vol. 70, p. 121) and cancer-associated bone disease (e.g., hypercalcaemia of malignancy, bone metastases, osteolytic bone metastases, multiple myeloma, breast carcinoma).

In one embodiment, the treatment is treatment of hypercalcaemia caused by conditions associated with increased bone resorption, including, but not limited to: vitamin D intoxication, primary or tertiary hyperparathyroidism, immobilisation, and sarcoidosis.

In one embodiment, the treatment is treatment of aseptic loosening of prosthetic implants (e.g., artificial joints, e.g., knees, hips, etc., can loosen due to osteoclast activity driven by local inflammation) (see, e.g., Childs, L. M., et al., 2001, *Journal of Bone and Mineral Research*, Vol. 16, No. 2, pp. 338-347).

In one embodiment, the treatment is treatment of osteopetrosis, osteoarthritis, or ectopic bone formation.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviatiation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, use with perimenopausal women who may not yet have osteoporosis, but who are at risk of osteoporosis, is encompassed by the term "treatment."

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously.

Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Other Uses

The APSAP compounds described herein may also be used as cell culture additives to inhibit immune cell function, for example, to inhibit the survival, formation, and/or activity of macrophages, T-cells, or other cells involved in the immune response.

The APSAP compounds, as described herein, may also be used as cell culture additives, for example, to inhibit osteoclasts, for example, to inhibit the survival, formation, and/or activity of osteoclasts.

The APSAP compounds described herein may also be used as part of an in vitro assay, for example, in order to determine whether a candidate host is likely to benefit from treatment with the compound in question.

The APSAP compounds described herein may also be used as a standard, for example, in an assay, in order to identify other active compounds, other osteoclast inhibitors, etc.

Kits

One aspect of the invention pertains to a kit comprising (a) an APSAP compound as described herein, or a composition comprising an APSAP compound as described herein, e.g., preferably provided in a suitable container and/or with suitable packaging; and (b) instructions for use, e.g., written instructions on how to administer the compound or composition.

The written instructions may also include a list of indications for which the APSAP compound is a suitable treatment.

Routes of Administration

The APSAP compound or pharmaceutical composition comprising the APSAP compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus.

In one preferred embodiment, the subject/patient is a human.

Formulations

While it is possible for the APSAP compound to be administered alone, it is preferable to present it as a pharmaceutical formulation (e.g., composition, preparation, medicament) comprising at least one APSAP compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one APSAP compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences*, 18th edition, Mack Publishing Company, Easton, Pa., 1990; and *Handbook of Pharmaceutical Excipients*, 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 100 μg/mL, for example from about 10 ng/mL to about 10 μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the APSAP compounds, and compositions comprising the APSAP compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular APSAP compound, the route of administration, the time of administration, the rate of excretion of the APSAP compound, the duration of the treatment, other drugs, compounds, and/or materials used in combination, the severity of the condition, and the species, sex, age, weight, condition, general health, and prior medical history of the patient. The amount of APSAP compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the APSAP compound is in the range of about 10 μg to about 250 mg (more typically about 100 μg to about 25 mg) per kilogram body weight of the subject per day. Where the compound is a salt, an ester, an amide, a prodrug, or the like, the amount administered is calculated on the basis of the parent compound and so the actual weight to be used is increased proportionately.

EXAMPLES

The following examples are provided solely to illustrate the present invention and are not intended to limit the scope of the invention, as described herein.

Chemical Synthesis

Synthesis 1

N-(3-Acetylphenyl)-4-bromobenzenesulfonamide

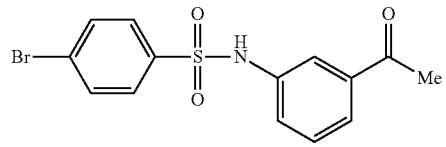

Method A: 4'-Bromobenzene sulfonyl chloride (1.5 g) and 3-aminoacetophenone (1.5 g) were dissolved in DCM (50 mL) and pyridine (3 mL) was added. The mixture was stirred overnight then poured into dilute HCl and extracted with DCM. The organic phase was washed with water, dried and evaporated to give a thick red oil, purified by column chromatography (ethyl acetate/petrol) and the title compound obtained as a white powder.

Synthesis 2

N-(3-Acetylphenyl)-2',4'-difluorobiphenyl-4-sulfonamide

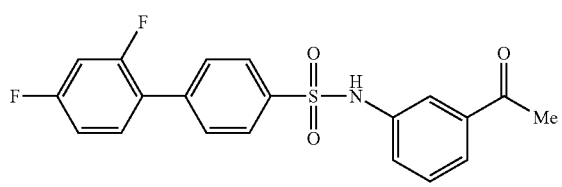

Method B: N-(3-Acetylphenyl)-4-bromobenzenesulfonamide (2 g) was dissolved in a mixture of toluene (20 mL) and ethanol (20 mL). 2,4-Difluorophenylboronic acid (2 g) was added followed by 2 M $Na_2CO_3$ (20 mL). The mixture was stirred vigorously under $N_2$ and $(PPh_3)_4Pd$ (0.2 g) added. The mixture was refluxed with stirring for 3 hours under an atmosphere of $N_2$. The solvent was removed under vacuum, the residue dissolved in ethyl acetate and washed with water and saturated NaCl solution. After drying ($Na_2SO_4$) the solvent was evaporated and the brown residue purified by column chromatography (ethyl acetate/petrol) and the title compound obtained as a crystalline white solid from ethyl acetate/petrol. $^{13}C$ NMR (250 MHz, DMSO-$d_6$): δ 26.7, 104.7 (m), 112.2 (m), 118.5, 118.7, 123.2, 124.2, 126.8, 127.4, 129.7, 132.1, 137.7, 138.2, 138.6, 138.7, 159.1 (dd, J=250.0, 11.7 Hz), 162.3 (dd, J=248.0, 11.7 Hz) and 197.3. $^1H$ NMR (250 MHz, DMSO-$d_6$): δ 2.48 (3H, s), 7.18 (1H, t, J=7.0 Hz), 7.31-7.41

(3H, m), 7.54-7.66 (3H, m), 7.70 (2H, d, J=9.2 Hz), 7.87 (2H, d, J=8.2 Hz) and 10.67 (1H, s).

Synthesis 3

N-(3-Acetylphenyl)-4'-bromobiphenyl-4-sulfonamide

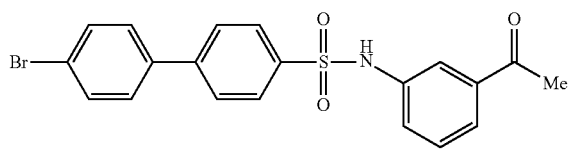

Using a method analogous to Method A, using 4'-bromobiphenyl sulfonyl chloride (1.5 g) and 3-aminoacetophenone (1.5 g), the title compound was obtained as a white powder.

Synthesis 4

N-(3-Acetylphenyl)-2',4'-dichlorobiphenyl-4-sulfonamide (ABD746)

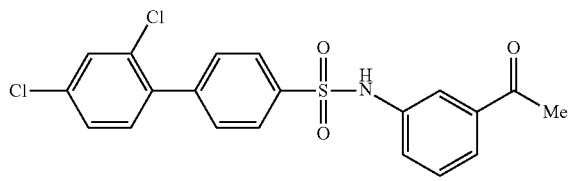

Method C: A solution of N-(3-acetylphenyl)-4-bromobenzenesulfonamide (350 mg, 1 mmol) and 2,4-dichlorophenylboronic acid (290 mg, 1.5 mmol) in dimethoxyethane (5 mL) was stirred under nitrogen and 2 M $Na_2CO_3$ (1.5 mL) was added. The flask was flushed with nitrogen before Pd(dppf)$Cl_2$ (36 mg, 0.05 mmol) was added and the flask was placed in an oil bath that had been pre-heated to 90° C. and stirred for 1 hour. The mixture was cooled, poured into water (50 mL) and extracted with ethyl acetate (3×25 mL). The extracts were washed with water (15 mL) and brine (15 mL) and dried over $MgSO_4$. Evaporation of the solvents afforded a brown solid which was purified by column chromatography on silica, eluting with hexane/acetone (2:1) and the title compound obtained as a pale brown powder (400 mg).

Synthesis 5

2',4'-Dichloro-N-(3-(2-hydroxypropan-2-yl)phenyl)biphenyl-4-sulfonamide (ABD707)

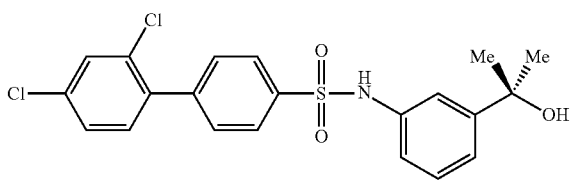

A solution of ABD746 (310 mg, 0.74 mmol) in anhydrous THF (10 mL) was cooled under nitrogen to 0° C. A solution of 3 M methylmagnesium bromide in diethyl ether (615 μL, 1.84 mmol) was added by syringe and the solution was stirred at 0° C. for 1 hour. Saturated $NH_4Cl$ (5 mL) was added at 0° C., the mixture diluted with water (5 mL) and ethyl acetate (20 mL), and the layers separated. The organic phase was washed with water (10 mL) and brine (10 mL) and dried over $MgSO_4$. Evaporation of the solvents gave a yellow solid which was purified by column chromatography on silica, eluting with hexane/acetone (2:1) to give the title compound as an off-white solid (275 mg). $^1$H NMR (300 MHz, DMSO-$d_6$): δ 1.28 (6H, s), 4.95 (1H, s), 6.94 (1H, d, J=8 Hz), 7.04-7.14 (2H, m), 7.16 (1H, s), 7.40 (1H, d, J=9 Hz), 7.50 (1H, d, J=9 Hz), 7.57 (2H, d, J=8 Hz), 7.74 (1H, br s), 7.80 (2H, d, J=8 Hz) and 10.26 (1H, br s). MS, m/z: Calcd, 435.046. Found, 435.24 (M).

Synthesis 6

2',4'-Dichloro-N-(3-(1-hydroxyethyl)phenyl)biphenyl-4-sulfonamide (ABD708)

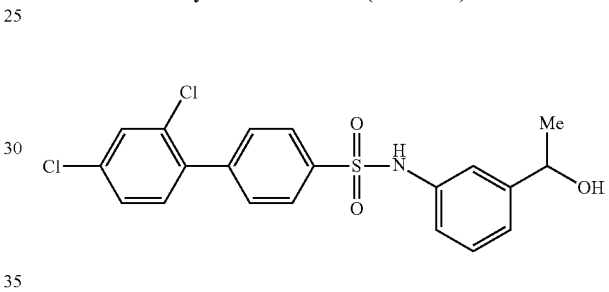

A solution of ABD746 (70 mg, 0.17 mmol) in methanol (5 mL) was cooled under nitrogen to 0° C. and $NaBH_4$ (13 mg, 0.33 mmol) was added in one portion. The mixture was stirred for 16 hours, allowing the temperature to rise to room temperature. Evaporation of the solvent gave a pale brown solid, which was purified by column chromatography on silica, eluting with hexane/acetone (2:1). The resulting waxy yellow solid was triturated with diethyl ether and hexane and the title compound obtained as a white solid (40 mg). $^1$H NMR (300 MHz, CDCl$_3$): δ 1.43 (3H, d, J=6 Hz), 4.82 (1H, q, J=6 Hz), 6.79 (1H, br s), 6.95-7.40 (6H, m), 7.47 (2H, d, J=8 Hz), 7.50 (1H, s) and 7.81 (2H, d, J=8 Hz). MS, m/z: Calcd, 421.031. Found, 421.14 (M).

Synthesis 7

2',4'-Dichloro-N-(3-(1-hydroxycyclopropyl)phenyl)biphenyl-4-sulfonamide (ABD709)

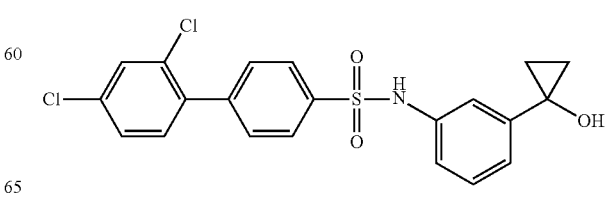

A solution of methyl 3-(2',4'-dichlorobiphenyl-4-ylsulfonamido)benzoate (500 mg, 1.03 mmol) and titanium isopropoxide (61 μL, 0.206 mmol) in anhydrous THF (10 mL) was cooled under nitrogen to −10° C. A solution of 3 Methylmagnesium iodide in THF (2.4 mL, 7.2 mmol) was added by syringe and the solution was stirred at 0° C. for 1 hour, then at room temperature overnight. The mixture was diluted with water (5 mL) and ethyl acetate (20 mL) and filtered through Celite. The layers were separated. The organic phase was washed with water (10 mL) and brine (10 mL) and dried over MgSO$_4$. Evaporation of the solvents gave an orange gum which was purified by column chromatography on silica, eluting with acetone/hexane (1:4) and the title compound obtained as a light yellow foam (100 mg). $^1$H NMR (300 MHz, CDCl$_3$): δ 0.95-1.05 (2H, m), 1.20-1.24 (2H, m), 6.90-7.10 (3H, m), 7.20-7.46 (3H, m), 7.47-7.48 (3H, m) and 7.83 (2H, d). MS, m/z: Calcd, 433.031. Found, 433.22 (M).

Synthesis 8

Ethyl 3-(4-bromophenyl-4-ylsulfonamido)benzoate

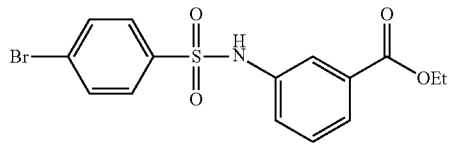

Using a method analogous to Method A, with 4-bromophenyl sulfonylchloride and ethyl 3-amino-benzoate, the title compound was obtained as a white powder.

Synthesis 9

Ethyl 3-(2',4'-dichlorobiphenyl-4-yl sulfonamido)benzoate

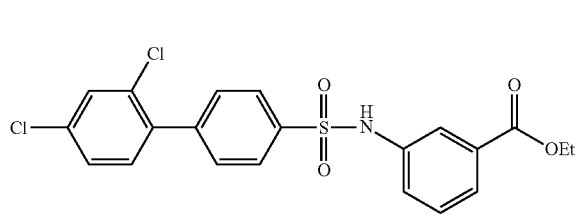

Using a method analogous to Method B, with ethyl-5-(4-bromophenyl-4-ylsulfonamido) benzoate and 2,4-dichlorophenylboronic acid, the title compound was obtained as white crystals. $^{13}$C NMR (250 MHz, DMSO-d$_6$): δ 14.1, 61.0, 120.3, 124.5, 125.2, 126.5, 126.9, 127.8, 129.9, 130.2, 130.8, 132.2, 133.1, 133.8, 137.1, 138.1, 138.9, 142.0 and 165.1. $^1$H NMR (250 MHz, DMSO-d$_6$): δ 1.27 (3H, t, J=7.3 Hz), 4.26 (2H, q, J=7.0 Hz), 7.39 (1H, d, J=7.9 Hz), 7.42 (1H, d, J=7.3 Hz), 7.43 (1H, s), 7.50 (1H, dd, J=8.2, 1.9 Hz), 7.60 (1H, m), 7.62 (2H, d, J=8.2 Hz), 7.74 (2H, s), 7.86 (2H, d, J=8.5 Hz) and 10.70 (1H, s). MS, m/z: Calcd, 449.03. Found, 449.23 (M).

Synthesis 10

3-(2',4'-Dichlorobiphenyl-4-ylsulfonamido)benzoic acid

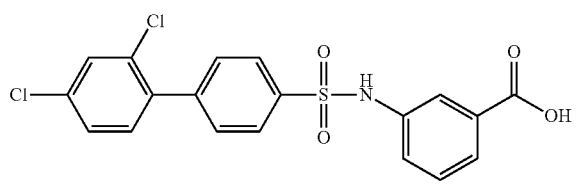

Ethyl 3-(2',4'-dichlorobiphenyl-4-ylsulfonamido)benzoate (0.4 g) was dissolved in a mixture of THF (5 mL) and methanol (5 mL). 1 M NaOH (10 mL) was added and the mixture stirred for 3 hours at room temperature followed by 1 hour at 50° C., by which stage a clear solution had formed. Concentrated HCl was added and the precipitate collected as a white solid. The solid was dissolved in ethyl acetate and dried with Na$_2$SO$_4$. Evaporation gave the title compound as a white solid, recrystallised from ethyl acetate/petrol. $^{13}$C NMR (250 MHz, DMSO-d$_6$): δ 122.4, 124.1, 125.0, 126.3, 126.5, 127.7, 129.6, 130.4, 131.9, 132.2, 132.5, 133.8, 137.1, 137.9, 138.9, 142.0 and 166.8. MS, m/z: Calcd, 420.99. Found, 421.22 (M).

Synthesis 11

3-(2',4'-Dichlorobiphenyl-4-ylsulfonamido)benzoyl chloride

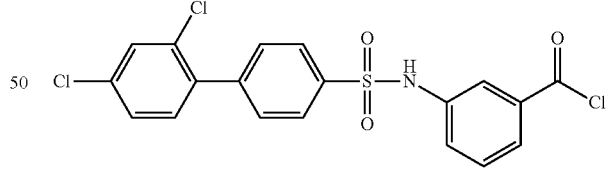

A suspension of 3-(2',4'-dichlorobiphenyl-4-ylsulfonamido)benzoic acid (1.50 g, 3.56 mmol) in DCM (35 mL) was stirred at 0° C. and oxalyl chloride (340 μL, 3.9 mmol) was added, followed by a catalytic amount of DMF (<50 μL). The mixture was allowed to warm to room temperature and stirred for two days, during which time the solid dissolved to form a light yellow clear solution. The mixture was evaporated under reduced pressure and the residue was azeotroped with toluene (3 mL), then hexane (10 mL) and the title compound obtained as a light brown, slightly gummy, solid (1.5 g) which was used without further purification.

Synthesis 12

3-(2',4'-Dichlorobiphenyl-4-ylsulfonamido)-N,N-dimethylbenzamide

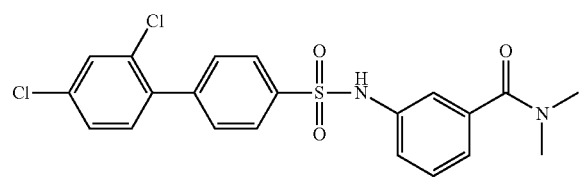

A solution of 2 M dimethylamine in THF (5 mL) was added to 3-(2',4'-dichlorobiphenyl-4-ylsulfonamido)benzoyl chloride (350 mg, 0.76 mmol) and the mixture was stirred at room temperature for 3 days. Saturated ammonium chloride (3 mL) was added and the solution acidified to pH 3 with 2 M HCl. The mixture was extracted with EtOAc (3×5 mL) and the organic layer was washed with brine (5 mL), dried over MgSO$_4$, filtered and evaporated to give a yellow glass. This was triturated with acetone and the title compound obtained as a white solid (130 mg).

Synthesis 13

2',4'-Dichloro-N-(3-((dimethylamino)methyl)phenyl)biphenyl-4-sulfonamide (ABD724)

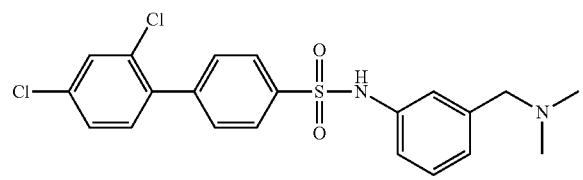

A solution of 3-(2',4'-dichlorobiphenyl-4-ylsulfonamido)-N,N-dimethylbenzamide (130 mg, 0.29 mmol) in THF (5 mL) was stirred at room temperature and 1 M borane in THF (1.45 mL, 1.45 mmol) was added. The solution was heated at 50° C. for 45 minutes. The mixture was then cooled and saturated ammonium chloride (5 mL) was added. The mixture was further diluted with water (10 mL) and extracted with EtOAc (3×15 mL). The combined organic layers were dried over MgSO$_4$, filtered and evaporated. The residue was purified by column chromatography (SiO$_2$, 20% acetone/hexane) and the title compound obtained as a light yellow glass (73 mg). $^1$H NMR (300 MHz, CDCl$_3$): δ 2.49 (6H, s), 3.87 (2H, s), 6.69 (1H, br s), 7.05-7.35 (6H, m), 7.49-7.50 (3H, m) and 7.81 (2H, d, J=9 Hz). MS, m/z: Calcd, 434.062. Found, 434.17 (M).

Synthesis 14

4-Bromo-N-(3-sulfamoylphenyl)benzenesulfonamide (ABD751a)

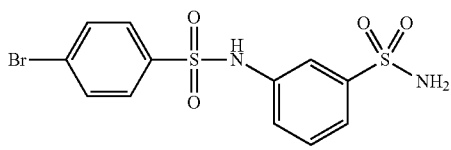

A solution of 4-bromobenzenesulfonyl chloride (1.34 g, 5.25 mmol), 3-aminobenzenesulfonamide (860 mg, 5.0 mmol) and DIPEA (1.29 g, 10 mmol) in THF (10 mL) was stirred overnight at room temperature. The solvent was then evaporated and the residue purified by chromatography on the SP4 (70 g Silica Isolute II, 0-100% EtOAc/hexane) to and the title compound obtained as a white solid (395 mg).

Synthesis 15

2',4'-Dichloro-N-(3-sulfamoylphenyl)biphenyl-4-sulfonamide (ABD751)

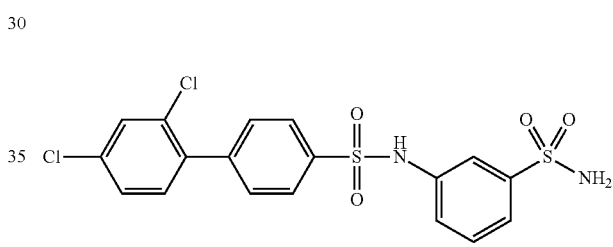

Using a method analogous to Method C, using ABD751a and 2,4-dichlorobenzeneboronic acid the title compound was obtained as an off-white solid (170 mg). $^1$H NMR (300 MHz, DMSO-d$_6$): δ 7.30 (1H, br d, J=7.5 Hz), 7.34-7.54 (6H, m), 7.56-7.63 (3H, m), 7.73 (1H, d, J=2.5 Hz), 7.86 (2H, d, J=8 Hz) and 10.78 (1H, br s). MS, m/z: Calcd, 455.977. Found, 456.17 (M).

Synthesis 16

2',4'-Dichloro-N-(3-formylphenyl)biphenyl-4-sulfonamide

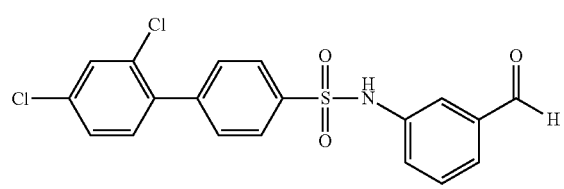

A solution of 2',4'-dichloro-N-(3-(hydroxymethyl)phenyl)biphenyl-4-sulfonamide (340 mg, 0.83 mmol) in DCM (10 mL) was stirred under argon at room temperature. Dess- Martin reagent (390 mg, 0.92 mmol) was added in one portion and the mixture was stirred for an hour. The suspension was filtered through Celite, rinsing well with DCM. The filtrate was washed with 1 M $Na_2S_2O_3$ (10 mL) and water (10 mL) and the DCM was dried over $MgSO_4$. The solvent was evaporated and the residue absorbed onto $SiO_2$ and purified by column chromatography (4×16 cm $SiO_2$, 25% acetone/hexane) and the title compound obtained as a yellow waxy solid (280 mg).

Synthesis 17

2',4'-Dichloro-N-(3-(2,2,2-trifluoro-1-hydroxyethyl) phenyl)biphenyl-4-sulfonamide (ABD766)

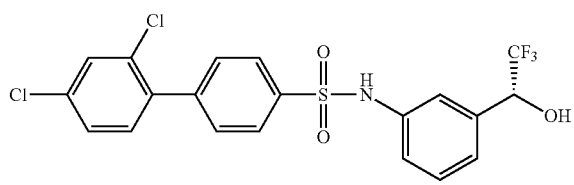

A solution of 2',4'-dichloro-N-(3-formylphenyl)biphenyl-4-sulfonamide (133 mg, 0.33 mmol) in dry THF (3 mL) was stirred under argon. Trifluoromethyl)trimethylsilane (58 μL) and 1 M TBAF in THF (33 μL) were added by syringe and the solution was stirred at room temperature. TLC indicated very little reaction, so further (trifluoromethyl)trimethylsilane (240 μL) and 1 M TBAF in THF (350 μL) were added. Stirring was continued for a further two hours, when TLC indicated the formation of a more polar compound. 1 M HCl (5 mL) was added and the mixture was stirred overnight. Diethyl ether (20 mL) was then added and the layers were separated. The aqueous phase was extracted with further diethyl ether (10 mL) and the combined extracts were dried ($MgSO_4$) and evaporated to afford a yellow gum (145 mg) consisting of a mixture of unreacted starting material and the desired product by LCMS. This mixture was redissolved in THF (2 mL) and further (trifluoromethyl)trimethylsilane (500 μL) and 1 M TBAF in THF (350 μL) were added. After 1 hour, the mixture was quenched and worked up as above. The crude product was purified by SP4 chromatography (20 g Isolute II Silica column, 0-30% acetone/hexane) gave a yellow gum (65 mg). This was triturated with ether and hexane and the title compound obtained as a white powdery solid (43 mg). $^1$H NMR (300 MHz, DMSO-$d_6$): δ 5.05 (1H, quintet, J=6 Hz), 6.78 (1H, d, J=6 Hz), 7.12 (2H, d, J=7 Hz), 7.20-7.28 (2H, m), 7.38 (1H, d, J=7 Hz), 7.49 (1H, dd, J=8 Hz, 2 Hz), 7.57 (2H, d, J=8 Hz), 7.76 (1H, d, J=2 Hz), 7.81 (2H, d, J=8 Hz) and 10.56 (1H, br s).

Synthesis 18

2',4'-Difluorobiphenylsulfonyl chloride

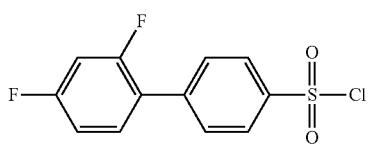

2,4-Difluorophenylboronic acid (15 g, 129 mmol) was added to a solution of bromobenzene (19.8 g, 126 mmol) in DME (500 mL). To this was added a solution of sodium carbonate (55.8 g, 520 mmol) in water (260 mL). The solution was degassed by bubbling argon through the mixture and then stirred under argon. Pd(dppf)$Cl_2$ (1.5 g, 2.1 mmol) was added and the flask was flushed with argon and heated at 90° C. overnight. The mixture was then cooled to room temperature and water (150 mL) and ethyl acetate (500 mL) were added. The layers were separated and the organic layer washed with 2 M NaOH (100 mL), water (100 mL) and brine (100 mL). The black ethyl acetate layer was dried over $MgSO_4$, charcoal was added, and the mixture was filtered through a short pad of silica. Evaporation of the solvents gave 2,4-difluorobiphenyl as a brown oil, which crystallised on standing (21.2 g).

2,4-Difluorobiphenyl (21.2 g, 111 mmol) was dissolved in chloroform (120 mL) and chlorosulfonic acid (12.5 mL, 188 mmol) was added dropwise. The reagents were stirred overnight at room temperature. The reaction was concentrated in vacuo and the residue was taken up into EtOAc (100 mL) and washed with water (3×25 mL). The organics were shaken with brine, whereupon a flocculent solid formed. This was filtered and washed with EtOAc and dried to give 2',4'-difluorobiphenyl sulfonic acid as an off-white solid (12.1 g).

2',4'-Difluorobiphenyl-4-sulfonic acid (12.1 g, 47 mmol) was suspended in thionyl chloride (100 mL). The mixture was heated at reflux for 30 minutes, when a catalytic amount of dry DMF was added and the reaction was heated at reflux for a further 4 hours. The reaction was then cooled and the thionyl chloride evaporated and the residue was then azeotroped with toluene (3×10 mL). The resulting yellow/orange gum was taken up into EtOAc 250 mL) and washed with water (50 mL) and brine (50 mL), and dried over $MgSO_4$. Filtration and evaporation gave the title compound as a brown oil which crystallized on standing (11 g).

Synthesis 19

2',4'-Difluoro-N-(3-vinylphenyl)biphenyl-4-sulfonamide

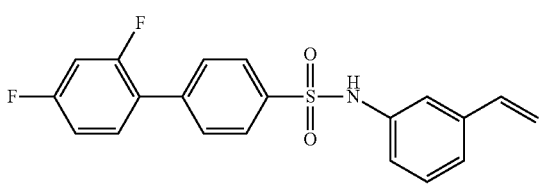

3-Amino styrene (1.36 g, 11.4 mmol) was added to a solution of 2',4'-difluorobiphenyl-4-sulphonyl chloride (3.0 g, 10.3 mmol) in DCM (25 mL) at 0° C. Pyridine (6.0 mL, 74 mmol) was then added and the mixture was allowed to stir and warm to room temperature overnight. The reaction was partitioned between further DCM (100 mL) and 2 M HCl (30 mL), stirred and separated. The DCM layer was washed with water (20 mL) and brine (20 mL) and dried over $MgSO_4$. The solvent was evaporated and the title compound obtained as an orange gum (3.46 g) which was used without further purification.

Synthesis 20

2',4'-Difluoro-N-(3-(oxiran-2-yl)phenyl)biphenyl-4-sulfonamide

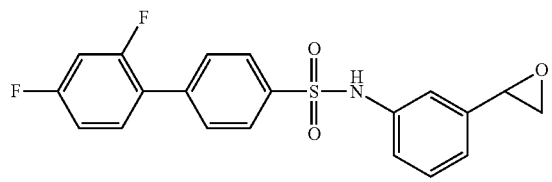

Dry meta-chloroperoxybenzoic acid (~85%, dried over KOH in a clean, dry, uncontaminated vacuum desiccator for at least 48 hours; 3.7 g, 21 mmol) was added to a solution of 2',4'-difluoro-N-(3-vinylphenyl)biphenyl-4-sulfonamide (1.16 g, 4.3 mmol) in dry DCM (30 mL) at 0° C. The mixture was allowed to warm to room temperature and stirred for 5 hours. Water (30 mL) was added and the layers were separated. The DCM layer was washed with 10% $Na_2SO_3$ (30 mL), saturated $NaHCO_3$ (30 mL), water (30 mL) and brine (30 mL) and dried over $MgSO_4$. The solvent was evaporated and the title compound obtained as an orange oil (1.16 g) which was used without further purification.

Synthesis 21

N-(3-(2-Amino-1-hydroxyethyl)phenyl)-2',4'-difluorobiphenyl-4-sulfonamide (ABD782)

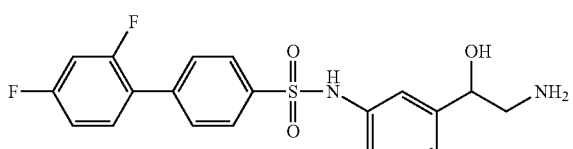

Method D: A solution of 2',4'-difluoro-N-(3-(oxiran-2-yl)phenyl)biphenyl-4-sulfonamide (1.1 g, 2.84 mmol) in dry THF (10 mL) was added dropwise to a solution of 20% ammonia in methanol (20 mL) and the reaction was stirred overnight. The solvents were evaporated and the residue was azeotroped with toluene. The crude product was dissolved in methanol, loaded onto a 5 g SCX II cartridge which was eluted with methanol until clear and then with 20% $NH_3$ in methanol and the title compound obtained as a mixture of regioisomers (1:1 with ABD790) which were not further separated. $^1$H NMR (300 MHz, $CDCl_3$): δ 2.76 (0.5H, br s), 3.02 (0.5H, br s), 3.45 (0.5H, br s), 3.60 (0.5H, br s), 3.95 (0.5H, br s), 4.30 (2H, br s), 4.60 (0.5H, br s), 6.70-7.60 (10H, m) and 7.80 (2H, br s).

Synthesis 22

2',4'-Difluoro-N-(3-(1-hydroxy-2-(methylamino)ethyl)phenyl)biphenyl-4-sulfonamide (ABD783)

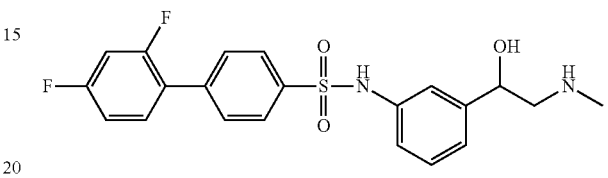

Using a method analogous to Method D, using 2',4'-difluoro-N-(3-(oxiran-2-yl)phenyl)biphenyl-4-sulfonamide and 33% methylamine in ethanol, a mixture of regioisomers was obtained. This solution was evaporated and the isomers were separated by flash chromatography ($SiO_2$, eluting with 5% to 20% methanol/DCM, containing 0.1% concentrated aqueous $NH_3$), giving ABD789 as a light orange powder (165 mg). With further elution (increasing the polarity slowly to 40% methanol/DCM) ABD783 was obtained as an orange gum, which was triturated with ether to give the title compound as a light orange powder (330 mg). $^1$H NMR (400 MHz, DMSO-$d_6$): δ 2.47 (3H, s), 2.70-2.76 (1H, t), 2.80-2.89 (1H, dd), 4.85 (1H, d, J=8 Hz), 6.95-7.15 (2H, m), 7.10-7.25 (3H, m), 7.40 (1H, t), 7.55-7.65 (1H, m), 7.66 (2H, d, J=8 Hz) and 7.84 (2H, d, J=8 Hz). MS, m/z: Calcd, 418.11. Found, 418.28 (M).

Synthesis 23

N-(3-(2-(Dimethylamino)-1-hydroxyethyl)phenyl)-2',4'-difluorobiphenyl-4-sulfonamide (ABD784)

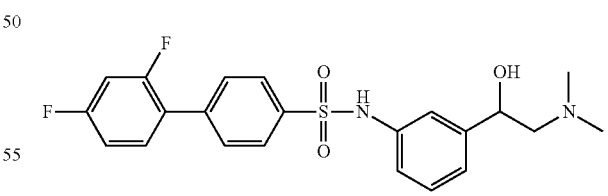

Using a method analogous to Method D, using 2',4'-difluoro-N-(3-(oxiran-2-yl)phenyl)biphenyl-4-sulfonamide and 33% dimethylamine in ethanol, a mixture of regioisomers was obtained. Reverse-phase HPLC was used to purify the mixture and the title compound was obtained as a pale orange powder. $^1$H NMR (300 MHz, $CDCl_3$): δ 2.70 (6H, s), 3.05-3.10 (2H, m), 5.05 (1H, bd), 6.80-6.95 (2H, m), 7.00-7.22 (3H, m), 7.25-7.35 (2H, m), 7.49 (2H, d, J=8 Hz) and 7.87 (2H, d, J=8 Hz).

Synthesis 24

2',4'-Difluoro-N-(3-(1-hydroxy-2-morpholinoethyl)phenyl)biphenyl-4-sulfonamide (ABD785)

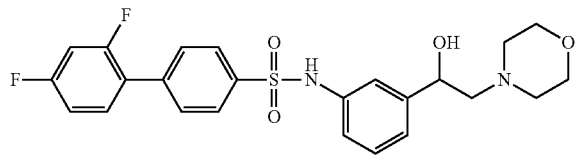

Using a method analogous to Method D, using 2',4'-difluoro-N-(3-(oxiran-2-yl)phenyl)biphenyl-4-sulfonamide and 1 M morpholine in methanol, a mixture of regioisomers was obtained. Reverse-phase HPLC was used to purify the mixture and the title compound was obtained as a pale orange powder. $^1$H NMR (300 MHz, CDCl$_3$): δ 2.20-2.40 (3H, m), 2.50-2.70 (2H, m), 3.60-3.80 (4H, m), 4.66 (1H, m), 6.85-7.00 (2H, m), 7.03-7.19 (3H, m), 7.20-7.30 (1H, m), 7.30-7.40 (1H, m), 7.57 (2H, d, J=8 Hz) and 7.91 (2H, d, J=8 Hz). MS, m/z: Calcd, 474.142. Found, 474.56 (M).

Synthesis 25

N-(3-Cyanophenyl)-2',4'-difluorobiphenyl-4-sulfonamide

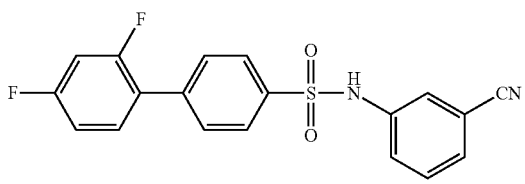

2',4'-Difluorobiphenylsulfonyl chloride (260 mg, 0.90 mmol) and 3-aminobenzonitrile (160 mg, 1.35 mmol) were stirred in DCM (10 mL) at room temperature. Pyridine (145 µL, 1.80 mmol) was added by syringe and the mixture was stirred overnight. The solution was poured into EtOAc (50 mL) and washed with 1 M HCl (2×10 mL), water (10 mL) and brine (10 mL). The solvent was dried over MgSO$_4$ and evaporated to give an orange oil (450 mg). This was absorbed onto SiO$_2$ and purified by SP4 chromatography (20 g Isolute II SiO$_2$ column, 0-30% acetone/hexane) and the title compound obtained as a yellow oil (330 mg).

Synthesis 26

N-(3-(Aminomethyl)phenyl)-2',4'-difluorobiphenyl-4-sulfonamide (ABD788)

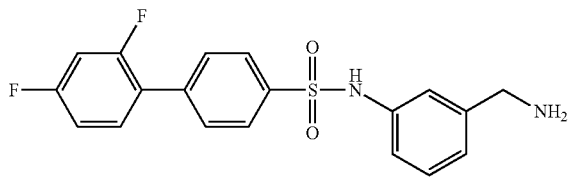

A solution of N-(3-cyanophenyl)-2',4'-difluorobiphenyl-4-sulfonamide in THF was cooled under argon to 0° C. A solution of LiAlH$_4$ in THF (2.67 mL) was added by syringe and the mixture was stirred for an hour, after which TLC indicated very little reaction. Further LiAlH$_4$ in THF (2.5 mL) was added and the mixture was allowed to warm to room temperature and stirred for 3 days. The solution was cooled to 0° C. and Na$_2$SO$_4$.10H$_2$O (500 mg) was added and the mixture stirred vigorously for 30 minutes. MgSO$_4$ was added and the mixture was filtered and evaporated to give an off-white solid (135 mg). This was purified by on a 2 g SCX column, eluting with DCM/MeOH (1:1, 2×5 mL) and then NH$_3$/MeOH/DCM (20% 2 M NH$_3$/MeOH in DCM; 4×5 mL) to give a glassy solid. This was triturated with diethyl ether and the title compound obtained as an off-white powder (40 mg). $^1$H NMR (400 MHz, DMSO-d$_6$): δ 3.65 (2H, s), 3.85 (2H, br s), 6.87 (1H, d, J=7.5 Hz), 6.92 (1H, d, J=7.5 Hz), 7.07 (1H, t, J=7.5 Hz), 7.17 (1H, td, J=9 Hz, 3 Hz), 7.35 (1H, td, J=10 Hz, 3 Hz), 7.57 (1H, q, J=6.5 Hz), 7.62 (2H, d, J=8 Hz) and 7.82 (2H, d, J=8 Hz). MS, m/z: Calcd, 374.09. Found, 374.30 (M).

Synthesis 27

2',4'-Difluoro-N-(3-(2-hydroxy-1-(methylamino)ethyl)phenyl)biphenyl-4-sulfonamide (ABD789)

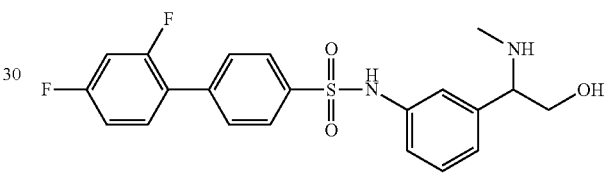

Using a method analogous to Method D, using 2',4'-difluoro-N-(3-(oxiran-2-yl)phenyl)biphenyl-4-sulfonamide and 33% methylamine in ethanol, the title compound was obtained as a light orange powder (165 mg) by flash chromatography of mixture of regioisomers which gave ABD783. $^1$H NMR (400 MHz, CDCl$_3$): δ 2.10 (3H, s), 3.51 (1H, m), 3.60-3.62 (2H, m), 5.10 (3H, br s), 6.70-6.95 (3H, m), 7.10-7.15 (4H, m), 7.20-7.25 (1H, m), 7.34 (2H, d, J=8 Hz) and 7.73 (2H, d, J=8 Hz). MS, m/z: Calcd, 418.11. Found, 418.09 (M).

Synthesis 28

N-(3-(1-Amino-2-hydroxyethyl)phenyl)-2',4'-difluorobiphenyl-4-sulfonamide (ABD790)

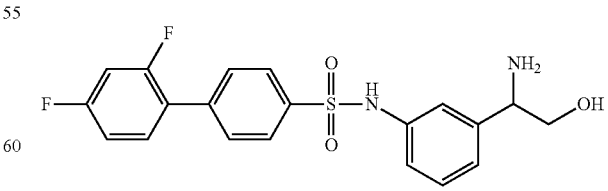

Using a method analogous to Method D, the title compound was obtained as a mixture of regioisomers (1:1 with ABD782) which were not further separated. $^1$H NMR (300 MHz, CDCl$_3$): δ 2.76 (0.5H, br s), 3.02 (0.5H, br s), 3.45

(0.5H, br s), 3.60 (0.5H, br s), 3.95 (0.5H, br s), 4.30 (2H, br s), 4.60 (0.5H, br s), 6.70-7.60 (10H, m) and 7.80 (2H, br s).

Synthesis 29

N-(3-(1-(Dimethylamino)-2-hydroxyethyl)phenyl)-2',4'-difluorobiphenyl-4-sulfonamide (ABD791)

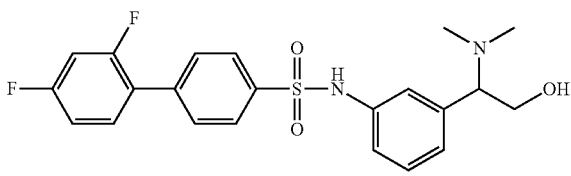

Using a method analogous to Method D, using 2',4'-difluoro-N-(3-(oxiran-2-yl)phenyl)biphenyl-4-sulfonamide and 33% dimethylamine in ethanol, a mixture of regioisomers was obtained. Reverse-phase HPLC was used to purify the mixture and the title compound was obtained as a pale orange powder from the mixture of isomers as gave ABD784. $^1$H NMR (300 MHz, CDCl$_3$): δ 2.08 (6H, s), 3.40 (3H, m), 3.48 (1H, m), 3.62-3.64 (1H, m), 6.87-6.96 (3H, m), 7.04-7.12 (2H, m), 7.20-7.25 (1H, m), 7.33-7.40 (1H, m), 7.53 (2H, d, J=8 Hz) and 7.78 (2H, d, J=8 Hz). MS, m/z: Calcd, 432.132. Found, 432.56 (M).

Synthesis 30

2',4'-Difluoro-N-(3-(2-hydroxy-1-morpholinoethyl)phenyl)biphenyl-4-sulfonamide (ABD792)

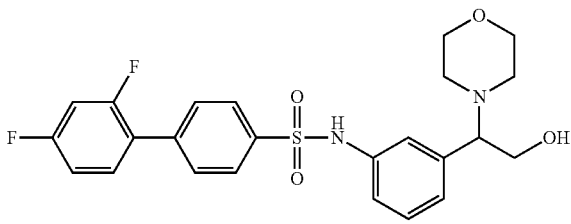

Using a method analogous to Method D, using 2',4'-difluoro-N-(3-(oxiran-2-yl)phenyl)biphenyl-4-sulfonamide and 1 M morpholine in methanol, a mixture of regioisomers was obtained. Reverse-phase HPLC was used to purify the mixture and the title compound was obtained as a pale orange powder from the mixture of isomers as gave ABD785. $^1$H NMR (300 MHz, CDCl$_3$): δ 2.75-2.81 (3H, m), 3.30 (1H, m), 3.60-3.95 (8H, m), 4.10-4.20 (1H, m), 6.80-7.10 (3H, m), 7.20-7.30 (2H, m), 7.35-7.45 (2H, m), 7.57 (2H, d, J=8 Hz) and 7.91 (2H, d, J=8 Hz). MS, m/z: Calcd, 474.142. Found, 474.58 (M).

Synthesis 31

(R)-2-(Methylamino)-2-phenylethanol (ABD810e)

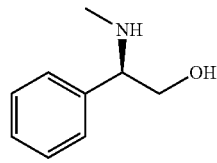

A solution of LiAlH$_4$ (1.0 M in THF, 184 mL, 0.184 mol) was added to a solution of (R)-(−)-phenyloxazolidin-2-one (15.0 g, 0.092 mol) in THF and then heated at reflux for 1.5 hours. The mixture was then cooled in an ice bath and quenched by portion-wise addition of sodium sulphate decahydrate, until bubbling ceased. The mixture was filtered through Celite and partitioned between EtOAc (200 mL) and water (100 mL). The layers were separated and the aqueous phase was extracted with EtOAc (3×100 mL). After drying over MgSO$_4$ the solvents were evaporated, giving the title compound as a yellow oil, which crystallised on standing to give an off white solid (10.3 g, 75%).

Synthesis 32

(R)-2-(Methylamino)-2-(3-nitrophenyl)ethyl nitrate (ABD810d)

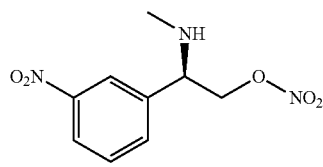

Concentrated HNO$_3$ (20 mL) was added dropwise to concentrated H$_2$SO$_4$ (20 mL) while cooling in an ice/methanol bath. The mixture was then cooled to below −20° C. and ABD810e (5.00 g, 25.5 mmol) was added portionwise with vigorous stirring, maintaining the temperature below −10° C. The mixture was stirred at −10° C. for 2 hours, then allowed to warm to 10° C. and stirred for a further 30 minutes. The mixture was then poured onto ice (150 g) and stirred until the ice melted, creating a suspension of a light yellow solid which was collected by filtration, washed with water and dried in a vacuum desiccator, giving the title compound as a dry, light yellow solid (5.0 g, 82%).

Synthesis 33

(R)-3-Methyl-4-(3-nitrophenyl)oxazolidin-2-one (ABD810c)

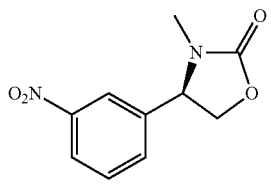

Carbonyl diimidazole (5.70 g, 0.032 mol) was added to a stirred solution of ABD810d (5.0 g, 0.035 mol) and triethylamine (14 mL, 0.103 mol) in DCM (80 mL) and heated at 40° C. overnight. Water (50 mL) was added and the layers were separated. The DCM layer was washed with 1 M HCl (20 mL), water (20 mL) and brine (20 mL) and dried over MgSO$_4$. The solution was filtered and evaporated to yield a light brown gum. The crude material was purified by dry flash chromatography, eluting with 30-40% acetone/hexane to give the title compound as a pale yellow-orange gum which solidified on standing (944 mg, 21%).

Synthesis 34

(R)-4-(3-Aminophenyl)-3-methyloxazolidin-2-one (ABD810b)

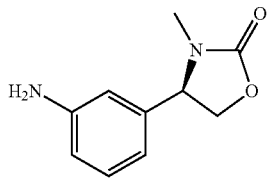

A solution of ABD810c (940 mg, 4.23 mmol) in IMS (20 mL) was stirred at room temperature and a suspension of 5% Pd/C (100 mg) in EtOAc (1 mL) was added. A balloon of hydrogen was fitted and the mixture was stirred for two hours at room temperature and then filtered through celite and evaporated to give the target compound as an orange gum (814 mg, 99%).

Synthesis 35

(R)-2',4'-Difluoro-N-(3-(3-methyl-2-oxooxazolidin-4-yl)phenyl)biphenyl-4-sulfonamide (ABD810a)

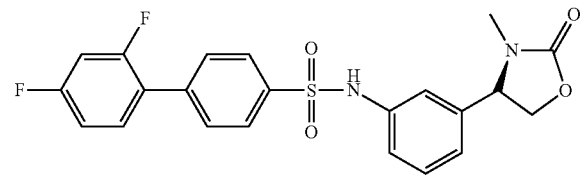

2,4-Difluorobiphenyl sulfonyl chloride (1.21 g, 4.23 mmol) was added to a solution of ABD810b (810 mg, 4.23 mmol) and pyridine (1.7 mL, 21 mmol) in DCM (20 mL) while cooling in an ice bath. The reaction mixture was stirred at room temperature overnight, then diluted with DCM (50 mL) and 1 M HCl (25 mL). The layers were separated and the DCM layer was washed with 1 M HCl (25 mL), water (25 mL) and brine (25 mL), and dried over MgSO$_4$, filtered and evaporated. The crude material was purified by flash chromatography, eluting with 30% acetone/hexane to give the title compound as a light yellow gum (1.08 g, 58%).

Synthesis 36

(R)-2',4'-Difluoro-N-(3-(2-hydroxy-1-(methylamino)ethyl)phenyl)biphenyl-4-sulfonamide (ABD810)

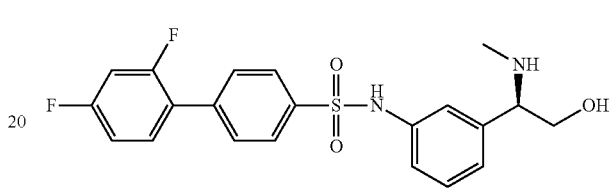

A solution of LiOH.H$_2$O (960 mg, 23 mmol) in water (15 mL) was added to a solution of ABD810a (1.06 g, 2.38 mmol) in THF (2.5 mL) and MeOH (2.5 mL) at room temperature. The mixture was heated at 65° C. overnight, after which the organic solvents were removed under reduced pressure and the residue was diluted with water (50 mL), then carefully neutralised with 2 M HCl to pH 7. The resulting suspension was extracted with EtOAc (3×50 mL) and the combined organic phases were washed with brine (40 mL) and dried over MgSO$_4$. Evaporation of the solvents afforded the product as a gum, which was re-dissolved in Et$_2$O and then Et$_2$O/hexane and re-evaporated to give the title compound as yellow foam (807 mg, 81%). $^1$H NMR (300 MHz, DMSO-d$_6$): δ 1.98 (3H, s), 3.12-3.20 (1H, m), 3.28-3.38 (2H, m), 4.83 (1H, s), 6.79 (2H, br t, J=9.5 Hz), 7.04 (1H, s), 7.13 (1H, t, J=7.5 Hz), 7.19 (1H, td, J=8 Hz, 2 Hz), 7.37 (1H, ddd, J=11.5 Hz, 9 Hz, 2.5 Hz), 7.56 (1H, td, J=9 Hz, 6.5 Hz), 7.64 (2H, d, J=8.5 Hz) and 7.77 (2H, d, J=8.5 Hz). LCMS: (MH)$^+$=419.

Synthesis 37

(S)-2',4'-Difluoro-N-(3-(2-hydroxy-1-(methylamino)ethyl)phenyl)biphenyl-4-sulfonamide (ABD811)

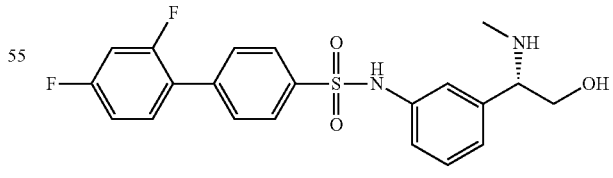

The title compound was prepared using a method analogous to that used for ABD810, starting with (S)-4-phenyloxazolidin-2-one. $^1$H NMR (300 MHz, DMSO-d$_6$): δ 1.98 (3H, s), 3.12-3.20 (1H, m), 3.28-3.38 (2H, m), 4.83 (1H, s), 6.79 (2H, br t, J=9.5 Hz), 7.04 (1H, s), 7.13 (1H, t, J=7.5 Hz), 7.19 (1H, td, J=8 Hz, 2 Hz), 7.37 (1H, ddd, J=11.5 Hz, 9 Hz, 2.5

Hz), 7.56 (1H, td, J=9 Hz, 6.5 Hz), 7.64 (2H, d, J=8.5 Hz) and 7.77 (2H, d, J=8.5 Hz). LCMS: (MH)+=419.

Synthesis 38

3-(4-Bromophenylsulfonamido)benzoyl chloride (ABD833d)

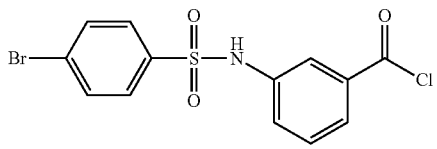

A suspension of 3-(4-bromophenylsulfonamido)benzoic acid (2.30 g, 6.46 mmol) in DCM (50 mL) was stirred and cooled under argon to 0° C. Oxalyl chloride (676 μL, 7.11 mmol) was then added dropwise via a syringe, followed by DMF (50 μL). The resulting solution was then stirred overnight, allowing the reaction mixture to warm room temperature. The solution was used without further purification.

Synthesis 39

3-(4-Bromophenylsulfonamido)-N,N-dimethylbenzamide (ABD833c)

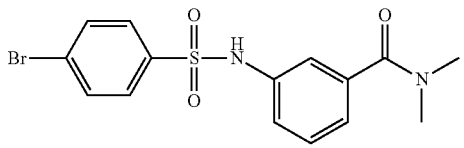

A solution of ABD833d (2.42 g, 6.46 mmol) in DCM (50 mL) was cooled to 0° C. under argon. Dimethylamine (2 M in THF, 16.15 mL, 32.30 mmol) was added dropwise via a syringe. Once addition was complete, the reaction was allowed to warm to room temperature and stirred for an additional 2 hours. After this time, the reaction was diluted with DCM (50 mL) and sat. NH₄Cl (25 mL). The aqueous phase was made acidic (pH 2) with 2 M HCl solution and the layers separated. The aqueous phase was then extracted with DCM (2×30 mL) and the combined organics were washed with water (25 mL), brine (25 mL), dried (Na₂SO₄) and filtered. Evaporation and recrystallisation (MeOH) gave the title compound as colourless prisms (2.35 g, 95%).

Synthesis 40

4-Bromo-N-(3-((dimethylamino)methyl)phenyl) benzenesulfonamide (ABD833b)

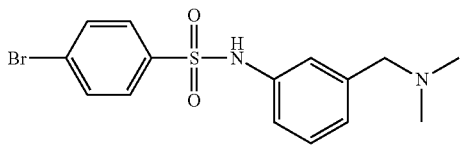

ABD833c (500 mg, 1.31 mmol) was dissolved in THF (10 mL) under argon (required gentle warming). When the temperature had fallen to 30° C., LiAlH₄ (1 M in THF, 2.62 mL, 2.62 mmol) was added via syringe over 15 minutes and effervescence was observed. After 1 hour the reaction was diluted with THF (10 mL) and cooled to 0° C. Na₂SO₄.10H₂0 (s) was added in portions until effervescence ceased. The mixture was filtered through celite and the solids washed with EtOAc (4×50 mL) and MeOH (4×50 mL). The combined organics were evaporated to give the title compound as a colourless oil (273 mg, 57%).

Synthesis 41

4-(N-(3-((Dimethylamino)methyl)phenyl)sulfamoyl) phenylboronic acid (ABD833a)

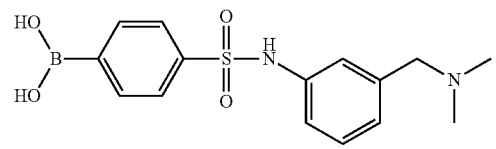

ABD833b (500 mg, 1.36 mmol), bis(pinacolato)diboron (518 mg, 2.04 mmol), Pd(dppf)Cl₂ (51 mg, 5 mol %) and KOAc (453 mg, 4.62 mmol) were suspended in DMSO (5 mL). The reaction was purged with argon in an ultrasonic bath for 5 minutes, and then placed in a pre-heated oil bath (90° C.) for 1.5 hours. The reaction was then cooled to room temperature, poured into water (50 mL), made acidic (pH 1) with 2 M HCl and then neutralised with Na₂CO₃ (sat. aq.). The mixture was extracted with EtOAc (4×50 mL) and the combined organics were then dried (Na₂SO₄), filtered and the solvent evaporated. The residue was absorbed onto silica and purified by flash chromatography, eluting with 5% 2 M NH₃/MeOH in DCM, to give the title compound as a dark brown solid (708 mg, quantitative).

Synthesis 42

4-(3,5-Dichloropyridin-2-yl)-N-(3-((dimethylamino) methyl)phenyl)benzene-sulfonamide (ABD833)

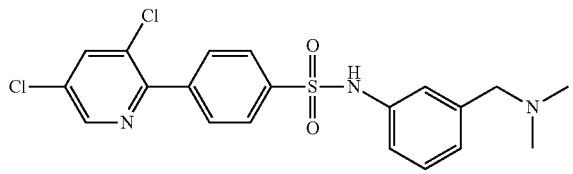

2-Bromo-2,5-dichloropyridine (236 mg, 1.05 mmol) and Pd(dppf)Cl₂ (37 mg, 5 mol %) were dissolved in a freshly prepared solution of ABD833a (approx. 1.27 mmol) in DMSO (20 mL), and 2 M Na₂CO₃ solution (1.58 mL, 3.15 mmol) was added. The vessel was sealed and purged with argon for 5 minutes while it was placed in an ultrasonic bath. The flask was then placed in a pre-heated oil bath (90° C.) for 1 h. After this time the reaction was cooled to room temperature, filtered and acidified with 2 M HCl. The crude mixture was roughly purified by SCX-2 chromatography (Isolute, 2 g) and the resulting material was purified further by chromatography on SiO$_2$ (70 g Isolute II cartridge, SP4), eluting with 4.5-5.5% 2 M NH$_3$/MeOH in DCM, then by reverse-phase HPLC. Finally, trituration with 1:1 v/v Et$_2$O:hexane gave the title compound as a colourless powder (23 mg, 5%). $^1$H NMR (300 MHz, DMSO-d$_6$): δ 2.15 (6H, s), 3.33 (2H, s), 6.98 (1H, t, J=2 Hz), 7.03-7.09 (2H, m), 7.21 (1H, t, J=8 Hz), 7.78 (2H, dt, J=8.5 Hz, 2 Hz), 7.83 (2H, dt, J=8.5 Hz, 2 Hz), 7.84 (1H, d, J=2 Hz) and 8.54 (1H, d, J=2 Hz). LCMS: (MH)$^+$=436; (M−H)$^-$=434.

Synthesis 43

4-(5-Chloropyrimidin-2-yl)-N-(3-((dimethylamino) methyl)phenyl)benzenesulfonamide (ABD834)

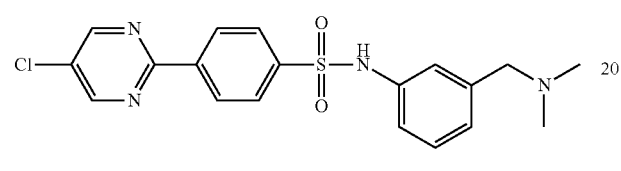

ABD833a (250 mg, 0.75 mmol), 2,5-dichloropyrimidine (133 mg, 0.90 mmol) and Pd(dppf)Cl$_2$ (29 mg, 5 mol %) were suspended in DME (4 mL) and 2 M Na$_2$CO$_3$ (1.12 mL, 2.24 mmol) was then added. The reaction was then purged with argon while standing in an ultrasonic bath for 5 minutes, and placed in a pre-heated oil bath (90° C.) for 1 hour. The reaction was cooled to room temperature, poured into water (50 mL) and extracted with EtOAc (3×25 mL). The combined organics were washed with water (25 mL) and brine (25 mL), dried (Na$_2$SO$_4$), filtered and the solvent evaporated. The crude product was purified by chromatography on SiO$_2$, eluting with 5% 2 M MeOH/NH$_3$ in DCM and then by preparative HPLC to give the title compound as a colourless solid (31 mg, 10%). $^1$H NMR (300 MHz, DMSO-d$_6$): δ 2.54 (6H, s), 4.12 (2H, br s), 6.90-7.40 (4H, m), 7.90 (2H, d, J=9 Hz), 8.43 (2H, d, J=9 Hz), 9.04 (2H, s) and 10.61 (1H, br s). LCMS: (MH)$^+$=403.

Synthesis 44

(R)-Methyl 2-(tert-butoxycarbonylamino)-2-(3-(2',4'-difluorobiphenyl-4-ylsulfonamido)phenyl)acetate (ABD854b)

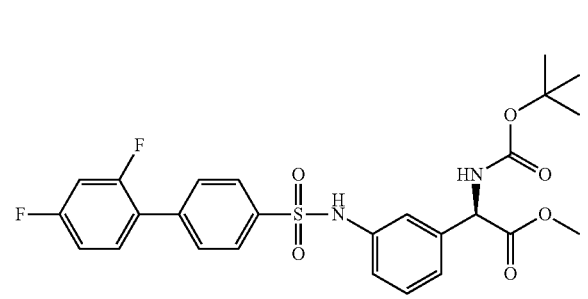

(R)-Methyl 2-(3-aminophenyl)-2-(tert-butoxycarbonylamino)acetate (385 mg, 1.37 mmol) (prepared in an analogous fashion to the (S)-isomer ABD855c) and 2',4'-difluorobiphenylsulfonyl chloride (396 mg, 1.37 mmol) were stirred in EtOAc (10 mL) and water (10 mL) and K$_2$CO$_3$ (760 mg, 5.5 mmol) was added. The mixture was stirred at room temperature for 3 days and then diluted with EtOAc (20 mL) and water (20 mL) and the layers were separated. The aqueous phase was extracted with EtOAc (10 mL) and the combined organics were washed with water (10 mL) and brine (10 mL) and dried over MgSO$_4$. After evaporation of the solvents, the crude material was purified by column chromatography on SiO$_2$, eluting with 10-50% acetone/hexane, to give the title compound as a yellow gum (580 mg, 80%).

Synthesis 45

(R)-tert-Butyl 1-(3-(2',4'-difluorobiphenyl-4-ylsulfonamido) phenyl)-2-hydroxyethylcarbamate (ABD854a)

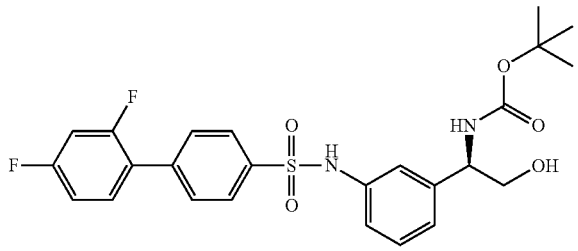

A solution of ABD854b (1.0 g, 1.9 mmol) in dry THF (60 mL) was cooled under argon to 0° C. and LiAlH$_4$ (1 M in THF, 9.4 mL, 9.4 mmol) was added by syringe. The mixture was stirred at 0° C. for 30 minutes and then allowed to warm to room temperature and stirred overnight. It was then cooled back to 0° C. and Na$_2$SO$_4$.10H$_2$O (s) was added until bubbling ceased. The mixture was diluted with further THF (60 mL) and stirred for 1 hour at room temperature and then filtered. After evaporation of the solvents, the residue was purified by chromatography on SiO$_2$ (20 g Isolute II cartridge, SP4), eluting with 30% acetone/hexane to give the title compound as an off-white solid (195 mg, 20%).

Synthesis 46

(R)—N-(3-(1-Amino-2-hydroxyethyl)phenyl)-2',4'-difluorobiphenyl-4-sulfonamide (ABD854)

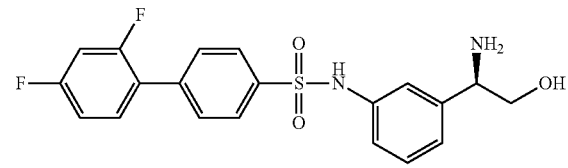

A solution of ABD854a (195 mg, 0.37 mmol) in DCM (10 mL) was stirred at room temperature and TFA (5 mL) was added. After 1 hour the solvents were evaporated and the residue was re-dissolved in DCM (5 mL) and loaded onto an SCX cartridge (2.0 g, (solute II) and eluted with DCM/MeOH (1:1, 2×5 mL) and then 5%-20% 2 M NH$_3$/MeOH in DCM. The product-containing fractions were combined and evaporated to afford a yellow gum which was triturated with Et$_2$O/hexane (1:1) to give the title compound as an off-white solid (118 mg, 79%). $^1$H NMR (400 MHz, DMSO-d$_6$): δ 3.18 (1H, t, J=9.5 Hz), 3.32-3.37 (1H, m obscured by water peak), 3.79 (1H, dd, J=8 Hz, 4.5 Hz), 4.83 (1H, br s), 6.96 (2H, br t, J=7

Hz), 7.10 (1H, s), 7.11 (1H, t, J=8 Hz), 7.18 (1H, td, J=8 Hz, 2 Hz), 7.37 (1H, ddd, J=11.5 Hz, 9 Hz, 2.5 Hz), 7.59 (1H, td, J=8.5 Hz, 6.5 Hz), 7.65 (2H, dd, J=8.5 Hz, 1.5 Hz) and 7.81 (2H, d, J=8.5 Hz). LCMS: (MH)⁺=405.

Synthesis 47

(S)-Methyl 2-amino-2-(3-nitrophenyl)acetate (ABD855e)

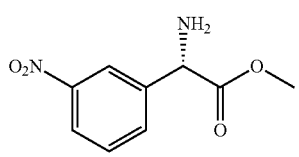

A mixture of HNO₃ (30 mL) and H₂SO₄ (30 mL) was cooled to below −10° C. and a solution of methyl (S)-phenylglycine hydrochloride (32.0 g, 0.149 mmol) in H₂SO₄ (30 mL) was added dropwise while stirring. The mixture was then stirred at 0° C. for 1 hour before being allowed to warm to room temperature and stirred for a further 30 minutes. The mixture was poured onto ice and then adjusted to pH 9 with conc. NH₄OH, while cooling to maintain the internal temperature <30° C. The mixture was extracted with EtOAc (4×100 mL) and the combined extracts were washed with brine (50 mL) and dried over MgSO₄. Evaporation of the solvent gave the title compound as a dark orange oil (30.3 g, 97%), which was used without further purification.

Synthesis 48

(S)-Methyl 2-(tert-butoxycarbonylamino)-2-(3-nitrophenyl)acetate (ABD855d)

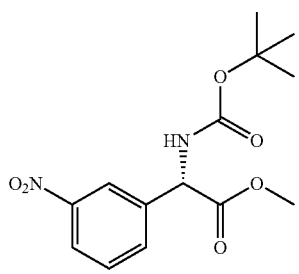

A suspension of ABD855e (30.3 g, 0.144 mol) and triethylamine (25 mL, 0.18 mol) in DCM (300 mL) was stirred at 0° C. and (BOC)₂O (40 g, 0.18 mmol) was added. The mixture was stirred overnight, allowing it to warm to room temperature. TLC indicated that some starting material remained, so further (BOC)₂O (5 g, 22 mmol) was added and stirring continued a further 3 hours. The mixture was then poured into water (200 mL) and the layers were separated. The organic phase was washed with 0.5 M HCl (50 mL), water (50 mL) and brine (50 mL) and dried over MgSO₄. After evaporation of the solvents, the crude material was purified by column chromatography on SiO₂ (0%-20% EtOAc/hexane) and then by trituration with warm hexane (3×) to give the title compound as an off-white solid (11 g, 25%).

Synthesis 49

(S)-Methyl 2-(3-aminophenyl)-2-(tert-butoxycarbonylamino)acetate (ABD855c)

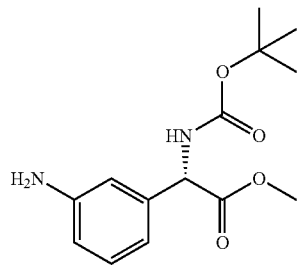

A 1 L autoclave was charged with a solution of ABD855d (11.0 g, 37 mmol) in MeOH 150 mL). Pd/C (10%, 1.0 g) was added as a slurry in EtOAc (5 mL) and the autoclave was sealed and charged to 50 bar (~5 MPa) with H₂ (g). The mixture was stirred at room temperature for 3 hours and then filtered through celite. Evaporation of the solvents gave the title compound as a dark green oil (10.3 g, quantitative), which was used without further purification.

Synthesis 50

(S)-Methyl 2-(tert-butoxycarbonylamino)-2-(3-(2',4'-difluorobiphenyl-4-ylsulfonamido)phenyl)acetate (ABD855b)

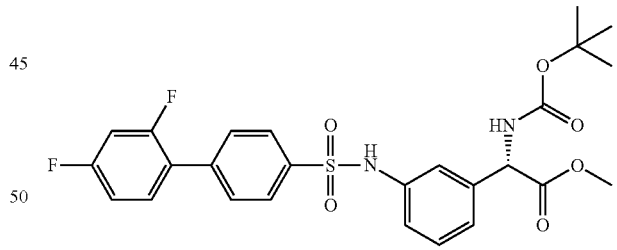

A solution of 2',4'-difluorobiphenylsulfonyl chloride (2.0 g, 6.9 mmol) in DCM (20 mL) was cooled under argon to 0° C. and ABD855c (2.4 g, 8.8 mmol) was added, followed by DMAP (1 crystal) and pyridine (2.94 mL, 36.5 mmol). The solution was stirred overnight, allowing it to warm to room temperature, and then diluted with further DCM (50 mL) and 1 M HCl (20 mL) and stirred for 30 minutes. The layers were separated and the DCM was washed with 1 M HCl (20 mL), water (20 mL) and brine (20 mL) and dried over Na₂SO₄. Evaporation of the solvents gave the title compound as an orange gum (3.75 g, quantitative) which was used without further purification.

Synthesis 51

(S)-tert-Butyl 1-(3-(2',4'-difluorobiphenyl-4-ylsulfonamido)phenyl)-2-hydroxyethylcarbamate (ABD855a)

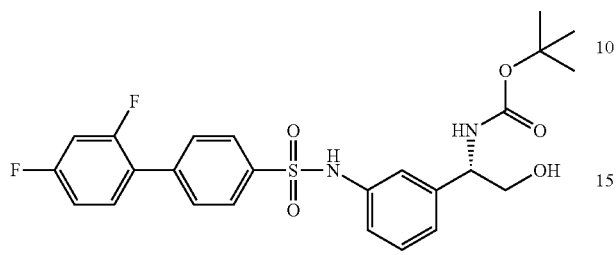

A solution of ABD855b (1.0 g, 1.87 mmol) in dry THF (20 mL) was cooled under argon to −10° C. and LiAlH$_4$ (1 M in THF, 3.75 mL, 3.75 mmol) was added by syringe. The solution was stirred for 2 hours, allowing it to warm to room temperature and then poured onto 10% NH$_4$Cl (aq., 25 mL). The mixture was extracted with EtOAc (3×20 mL) and the combined organics were dried over MgSO$_4$, filtered and evaporated to afford an orange gum. This was purified by column chromatography on SiO$_2$ (20%-30% acetone/hexane) to give the title compound as a yellow gum (659 mg, 70%).

Synthesis 52

(S)—N-(3-(1-Amino-2-hydroxyethyl)phenyl)-2',4'-difluorobiphenyl-4-sulfonamide (ABD855)

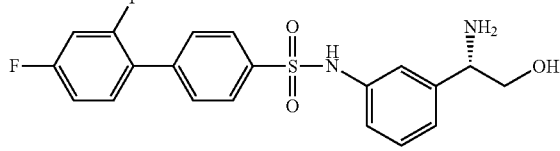

ABD855a (100 mg, 0.20 mmol) was stirred in dioxane (10 mL) at room temperature and HCl/dioxane (3 M, 5 mL) was added. The mixture was stirred at room temperature for 2 days and then concentrated under reduced pressure. The residue was stirred with Et$_2$O (5 mL) giving a pale brown solid which was collected by suction filtration. Trituration with further Et$_2$O and then hexane gave the title compound as the hydrochloride salt (77 mg, 87%). $^1$H NMR (400 MHz, DMSO-d$_6$): δ 3.50-3.70 (2H, m), 4.20 (1H, m), 5.49 (1H, m), 7.00 (1H, d, J=8 Hz), 7.10 (1H, d, J=8 Hz), 7.14-7.30 (3H, m), 7.45-7.55 (1H, m), 7.60 (1H, m), 7.65 (2H, d, J=8 Hz), 7.85 (2H, d, J=8 Hz), 8.35 (2H, br s) and 10.50 (1H, s). LCMS: (MH)$^+$=405.

Synthesis 53

2-Bromo-1-(3-nitrophenyl)ethanone

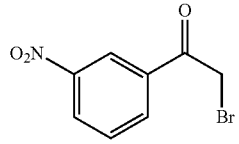

m-Nitroacetophenone (20 g) was dissolved in acetic acid (150 mL) under argon. Pyridinium tribromide (38.7 g) was added at once; the reaction was allowed to stir at room temperature for 1 hour and then quenched with water (250 mL). The product was filtered and air dried to give the title compound (25 g, 84%).

Synthesis 54

2-(3-Nitrophenyl)-2-oxoethyl acetate

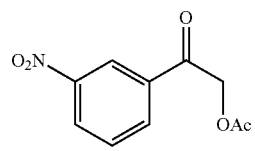

2-Bromo-1-(3-nitrophenyl)ethanone (25 g) was dissolved in methylethyl ketone (150 mL). NaOAc (12.5 g) was added and the mixture stirred for 48 hours. Water (100 mL) was added and the reaction mixture extracted with DCM. The DCM layer was dried over Na$_2$SO$_4$ and concentrated to give the title compound (20 g, 87%).

Synthesis 55

2-Hydroxy-2-(3-nitrophenyl)ethyl acetate

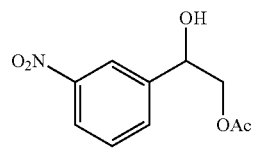

2-(3-Nitrophenyl)-2-oxoethyl acetate (20 g) was dissolved in MeOH (200 mL) and cooled to 0° C. Sodium borohydride (6.78 g) was added pinch-wise to the reaction mixture and this was stirred for 2 hours at room temperature. The reaction was quenched by addition of acetone (10 mL) and the mixture concentrated to give a solid. The solid was treated with water (100 mL) and extracted with ethyl acetate (3×100 mL). The crude title compound obtained was used for next step without further purification (18 g, 89%).

Synthesis 56

1-(3-Nitrophenyl)ethane-1,2-diol

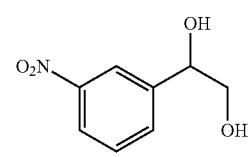

2-Hydroxy-2-(3-nitrophenyl)ethyl acetate (18 g) was dissolved in MeOH (180 mL) and cooled to 0° C. K$_2$CO$_3$ (22 g) was added and the reaction stirred at room temperature for 2 hours. The mixture was concentrated under vacuum, quenched by addition of water (100 mL) and extracted with ethyl acetate (2×100 mL). The EtOAc layer was dried over Na₂SO₄ and concentrated to give the crude title compound (13 g, 88%).

Synthesis 57

1-(3-Aminophenyl)ethane-1,2-diol

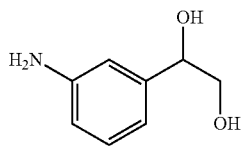

1-(3-Nitrophenyl)ethane-1,2-diol (10 g) was dissolved in MeOH (100 ml). 10% Pd/C (1.3 g) was added the mixture hydrogenated at 40 psi H₂ for 1 hour. The reaction mass was filtered through hyflo and concentrated to give the crude title compound (10 g, 92%).

Synthesis 58

Benzyl 3-(1,2-dihydroxyethyl)phenylcarbamate

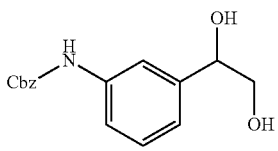

1-(3-Aminophenyl)ethane-1,2-diol (10 g) was dissolved in DCM (80 mL). H₂O (80 mL) and Na₂CO₃ (10.98 g) were added and the mixture cooled to 0° C. Benzylchloroformate (22 g) was added drop-wise over 20 minutes and the reaction mixture stirred at room temperature overnight. The organic phase was separated, dried over Na₂SO₄ and concentrated to give a crude product which was purified by column chromatography to give the title compound (8 g, 45%).

Synthesis 59

Benzyl 3-(2-(tert-butyldimethylsilyloxy)-1-hydroxy-ethyl)phenylcarbamate

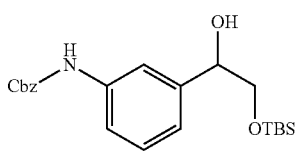

Benzyl 3-(1,2-dihydroxyethyl)phenylcarbamate (8 g) was dissolved in dry DMF (50 mL) and cooled to 0° C. Imidazole (2.8 g) and TBSCl (5 g) were added and the mixture was stirred at room temperature for 24 hours. The reaction was quenched by addition of water (100 mL) and extracted with EtOAc (2×100 mL). The organic phase was separated, dried over Na₂SO₄ and concentrated to give a crude product which was purified by column chromatography to give the title compound (6 g, 60%).

Synthesis 60

1-(3-(Benzyloxycarbonylamino)phenyl)-2-(tert-butyldimethylsilyloxy)ethyl methanesulfonate

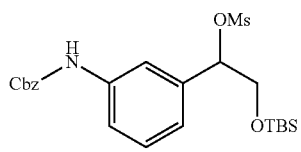

Benzyl 3-(2-(tert-butyldimethylsilyloxy)-1-hydroxyethyl)phenylcarbamate (4 g) was dissolved in dry DCM (80 mL) and cooled to 0° C. under an argon atmosphere. Triethylamine (5 g) was added, followed by mesyl chloride (3.42 g) added drop-wise over a period of 2 hours. The reaction temp was maintained at 0° C. for further 2 hours. The reaction was quenched by addition of water, extracted into DCM and concentrated under vacuum at a temperature below 25° C. The crude product (3.5 g) was unstable and was used for next step as soon as possible.

Synthesis 61

{3-[2-(tert-Butyl-dimethyl-silanyloxy)-1-(2-methoxy-ethylamino)-ethyl]-phenyl}-carbamic acid benzyl ester

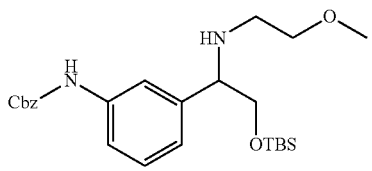

1-(3-(Benzyloxycarbonylamino)phenyl)-2-(tert-butyldimethylsilyloxy)ethyl methanesulfonate (3.5 g) was dissolved in dry THF (10 mL) and methoxyethylamine (5.4 g) was added in a sealed tube and heated to 70° C. for 16 hours. Water was added and the reaction mixture extracted with DCM (2×20 mL). The organic phase was separated, dried over Na₂SO₄ and concentrated to give the crude product, which was purified by column chromatography to give the title compound (1 g, 30%).

Synthesis 62

{3-[1-[tert-Butoxycarbonyl-(2-methoxy-ethyl)-amino]-2-(tert-butyl-dimethyl-silanyloxy)ethyl]-phenyl}-carbamic acid benzyl ester

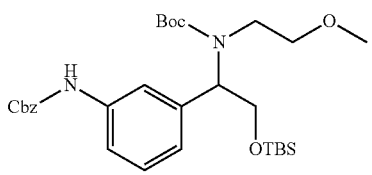

{3-[2-(tert-Butyl-dimethyl-silanyloxy)-1-(2-methoxy-ethylamino)-ethyl]-phenyl}-carbamic acid benzyl ester (1 g) was dissolved in dry DCM (10 mL) and stirred under argon at 0° C. Triethylamine (0.4 g) and (BOC)₂O (0.52 g) were added and the reaction mixture was stirred at room temperature for 2 days. The reaction was quenched by addition of water and the mixture extracted with DCM. The organic phase was separated, dried over Na₂SO₄ and concentrated to give a crude product which was purified by column chromatography to give the title compound (400 mg).

Synthesis 63 tert-Butyl 1-(3-aminophenyl)-2-(tert-butyldimethyl-silyloxy)ethyl(2-methoxyethyl)carbamate

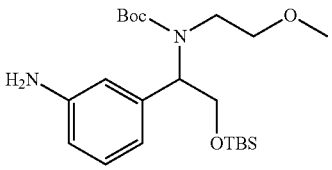

{3-[1-[tert-Butoxycarbonyl-(2-methoxy-ethyl)-amino]-2-(tert-butyl-dimethyl-silanyloxy)ethyl]-phenyl}-carbamic acid benzyl ester was added to ethanolic HCl (20 mL) at 0° C., allowed to warm to room temperature and stirred overnight. The reaction mixture was concentrated to give the title compound as a light yellow oil (300 mg).

Synthesis 64 tert-Butyl 1-(3-(4-bromophenylsulfonamido)phenyl)-2-(tert-butyldimethylsilyloxy)ethyl(2-methoxyethyl) carbamate (ABD858b)

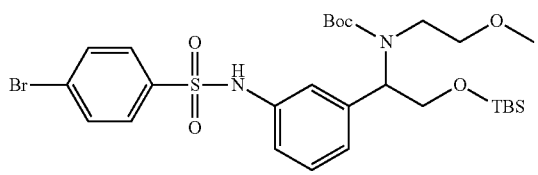

A suspension of tert-butyl 1-(3-aminophenyl)-2-(tert-butyldimethylsilyloxy)ethyl(2-methoxyethyl)carbamate (0.5 g, 1.95 mmol) and 4-bromobenzenesulfonyl chloride (0.99 g) in chloroform (20 mL) was stirred under nitrogen at room temperature. N,N-Diisopropylethylamine (1 mL) was added and the mixture was stirred for 16 hours at 60° C. The solution was diluted with EtOAc (50 mL), washed with water (2×20 mL), 1 M HCl (20 mL) and brine (20 mL) and dried over Na₂SO₄. Evaporation of the solvents gave a brown oil which was purified by column chromatography (30% EtOAc in hexane) to give the title compound as a light yellow oil (0.3 g).

Synthesis 65 tert-Butyl 2-(tert-butyldimethylsilyloxy)-1-(3-(2',4'-difluorobiphenyl-4-ylsulfonamido)phenyl)ethyl(2-methoxyethyl)carbamate (ABD858a)

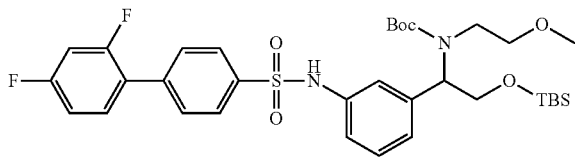

ABD858b (300 mg) and 2,4-difluorophenylboronic acid (110 mg) were stirred in DME (8 mL) and 2 M Na₂CO₃ (1.2 mL) was added. The flask was stoppered and flushed with N₂ (g) for 5 minutes. Pd(dppf)Cl₂ (10 mg) was then added, the flask placed in an oil bath at 90° C. and stirred for 8 hours. The reaction mixture was cooled, filtered over a celite bed and diluted with EtOAc (50 mL). The solution was washed with water (2×20 mL) and brine (20 mL) and dried over Na₂SO₄. Evaporation of the solvent under reduced pressure gace a brown oil which was purified by column chromatography (10% EtOAc in hexane) followed by trituration with n-pentane and ether and the title compound obtained as a light yellow oil (200 mg).

Synthesis 66

2',4'-Difluoro-N-(3-(2-hydroxy-1-(2-methoxyethylamino)ethyl)phenyl)biphenyl-4-sulfonamide (ABD858)

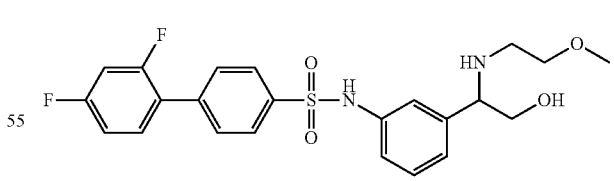

ABD858a (200 mg) was added to ethanolic HCl (20 mL) at 0° C., allowed to warm to room temperature and stirred overnight at room temperature. The reaction mixture was concentrated to a yellow oil, which was purified by column chromatography (20% EtOAc in n-hexane) to give the title compound as a sticky solid (50 mg, 38% yield). ¹H NMR (300 MHz, DMSO-d₆): δ 3.11 (3H, s), 3.26 (1H, m), 3.35 (1H, m), 3.54 (2H, m), 3.76 (1H, m), 3.94 (3H, m), 5.17 (1H, m), 6.44

(1H, s), 6.54 (2H, m), 6.91-7.02 (3H, m), 7.38 (1H, m), 7.59 (2H, d, J=8.4 Hz) and 7.94 (2H, d, J=8.4 Hz); LCMS: (M)⁺=462.

Synthesis 67

N-(3-((Dimethylamino)methyl)phenyl)-4-(pyrimidin-2-yl)benzenesulfonamide (ABD860)

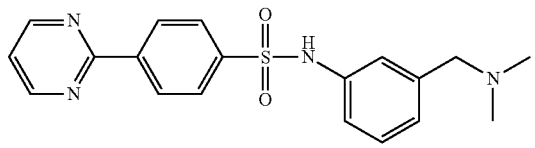

4-Bromo-N-(3-((dimethylamino)methyl)phenyl)benzenesulfonamide (273 mg, 0.74 mmol), pyrimidine-5-boronic acid (101 mg, 0.81 mmol) and Pd(dppf)Cl₂ (29 mg, 5 mol %) were dissolved in DME (4 mL) and 2M Na₂CO₃ solution (1.11 mL, 2.22 mmol) was added. The vessel was sealed and purged with argon for 5 minutes while it was placed in an ultrasonic bath. The flask was then placed in a pre-heated oil bath (90° C.) for 1 hour. After this time the reaction was cooled to room temperature and absorbed onto silica. The material was semi-purified by flash chromatography (Isolute II, 70 g silica cartridge, SP4) eluting with 4.5-5.5% MeOH/NH₃:DCM, followed by reverse-phase HPLC and finally by trituration from 1:1 v/v Et₂O:hexane to give the title compound as a colourless solid (26 mg, 10%). ¹H NMR (300 MHz, DMSO-d₆): δ 2.13 (6H, s), 3.32 (2H, s), 6.99 (1H, br s), 7.06 (2H, d, J=9 Hz), 7.21 (1H, t, J=8 Hz), 7.62 (2H, d, J=8.5 Hz), 7.89 (2H, d, J=8.5 Hz), 8.92 (2H, s) and 9.25 (1H, s). LCMS: (MH)⁺=369; (M−H)⁻=367.

Synthesis 68

Methyl 2-(tert-butoxycarbonylamino)-2-(3-nitrophenyl)propanoate (ABD862d)

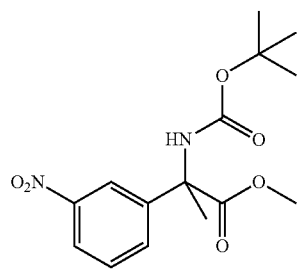

A solution of ABD855d (1.0 g, 3.2 mmol) and MeI (2.0 mL, 32.2 mmol) in dry THF (15 mL) was stirred under argon at 0° C. and KOᵗBu (470 mg, 4.2 mmol) was added in one portion. The mixture was stirred for 2 days, allowing it to warm to room temperature. HPLC analysis indicated that significant starting material was still present so a further portion of KOᵗBu (35 mg, 0.32 mmol) was added and stirring continued for an hour, after which a second portion of KOᵗBu (70 mg, 0.64 mmol) and MeI (0.36 mL, 6.4 mmol) were added and stirring was continued overnight. Saturated NH₄Cl (aq., 5 mL) was then added and the mixture was extracted with EtOAc (3×10 mL). The combined extracts were washed with water (10 mL) and brine (10 mL) and dried over MgSO₄. After evaporation of the solvents, the residue was purified by dry flash chromatography on SiO₂ (5%-20% EtOAc/hexane) to afford the title compound as a yellow oil (503 mg, 48%).

Synthesis 69

Methyl 2-(3-aminophenyl)-2-(tert-butoxycarbonylamino)propanoate (ABD862c)

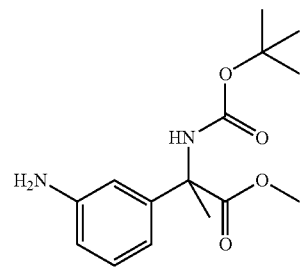

A solution of ABD862d (500 mg, 1.54 mmol) in MeOH (10 mL) was stirred at room temperature and Pd/C (10%, 50 mg) was added as a slurry in MeOH (1 mL). The flask was fitted with a balloon of H₂ (g) and stirred vigorously overnight. The mixture was filtered through celite and the solvents evaporated to give the title compound as a pale yellow-green oil (440 mg, 97%), which was used without further purification.

Synthesis 70

Methyl 2-(tert-butoxycarbonylamino)-2-(3-(2',4'-difluorobiphenyl-4-ylsulfonamido)phenyl)propanoate (ABD862b)

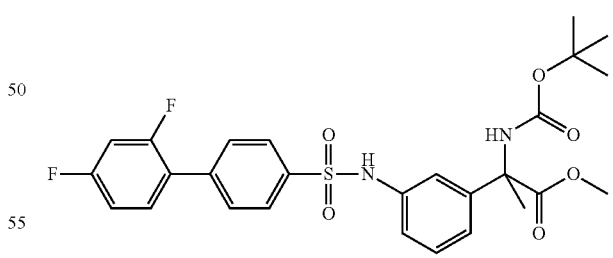

A solution of ABD862c (440 mg, 1.5 mmol) in DCM (10 mL) was cooled to 0° C. and then 2',4'-biphenylsulfonyl chloride (408 mg, 1.5 mmol) was added, followed by pyridine (600 μL, 585 mg, 7.5 mmol). The mixture was stirred for 3 hours, allowing it to warm to room temperature, and then water (10 mL) and 2 M HCl (10 mL) were added. The layers were separated and the aqueous phase was extracted with DCM (3×10 mL). The combined organics were washed with 1 M HCl (10 mL), water (10 mL) and brine (10 mL) and dried over MgSO₄. Evaporation of the solvents gave the title compound as an orange gum (800 mg, 97%) which was not purified further.

Synthesis 71 tert-Butyl 2-(3-(2',4'-difluorobiphenyl-4-ylsulfonamido)phenyl)-1-hydroxypropan-2-ylcarbamate (ABD862a)

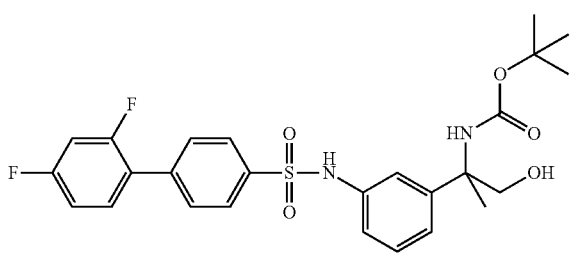

A solution of ABD862b (800 mg, 1.46 mmol) in dry THF (10 mL) was cooled to −5° C. (ice/MeOH) and LiAlH₄ (1 M in THF, 7.3 mL, 7.3 mmol) was added dropwise. The mixture was stirred overnight, allowing it to warm to room temperature. It was then cooled back to −5° C. and sat. NH₄Cl (aq., 5 mL) was added cautiously, followed by water (20 mL) and EtOAc (20 mL) and the mixture was stirred vigorously. After filtering through celite, the layers were separated and the aqueous phase was extracted with EtOAc (3×10 mL). The combined organics were washed with water (10 mL) and brine (10 mL) and dried over MgSO₄. After evaporation of the solvents, the residue was purified by column chromatography on SiO₂ (20%-40% acetone/hexane) to give the title compound as a pale yellow gum (330 mg, 44%).

Synthesis 72

N-(3-(2-Amino-1-hydroxypropan-2-yl)phenyl)-2',4'-difluorobiphenyl-4-sulfonamide (ABD862)

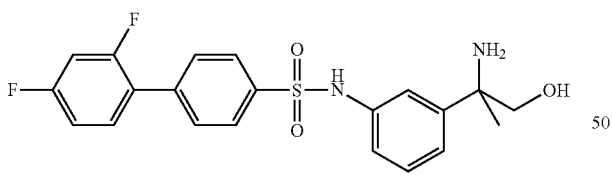

A solution of ABD862a (330 mg, 0.64 mmol) in dioxane (10 mL) was stirred at room temperature and HCl/dioxane (4 M, 3 mL) was added. The mixture was stirred at room temperature overnight and the solvent was then evaporated under reduced pressure. The resulting yellow gum was taken up in MeOH (5 mL) and loaded onto an SCX-2 column (2 g). The column was eluted with MeOH (3×5 mL) and then 15% NH₃/MeOH, resulting in some purification. The procedure was repeated and the resulting orange gum was triturated with Et₂O to afford an off-white foam. Final purification by reverse-phase preparative HPLC gave the title compound as an off-white solid (48 mg, 18%). $^1$H NMR (300 MHz, DMSO-$d_6$): δ 1.17 (3H, s), 3.27 (2H, s), 4.78 (1H, br s), 6.88-6.92 (1H, m), 7.04-7.10 (2H, m), 7.14-7.22 (2H, m), 7.37 (1H, ddd, J=11.5 Hz, 9 Hz, 2 Hz), 7.58 (1H, td, J=9 Hz, 6.5 Hz), 7.61 (2H, dd, J=8.5 Hz, 1.5 Hz) and 7.80 (2H, d, J=8.5 Hz). LCMS: (MH)⁺=419; (M−H)⁻=417.

Synthesis 73

4-Bromo-3-methyl-N-(3-sulfamoylphenyl)benzenesulfonamide (ABD866a)

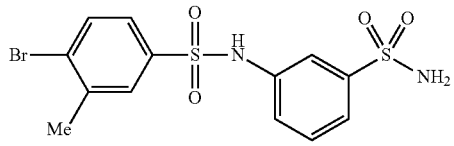

Method E: 4-Bromo-3-methylbenzenesulfonyl chloride (1.5 g) was dissolved in DCM (30 mL). 3-Aminobenzenesulfonamide (3 g) was added, followed by pyridine (5 mL) and the mixture was stirred overnight at room temperature. The mixture was poured into water and acidified (HCl). The solid was collected by filtration, dissolved in EtOAc and washed with water. The organic phase was collected, dried, most of the solvent removed and the product crystallised by addition of petrol.

Synthesis 74

2'-4'-Difluoro-2-methyl-N-(3-sulfamoylphenyl)biphenyl-4-sulfonamide (ABD866)

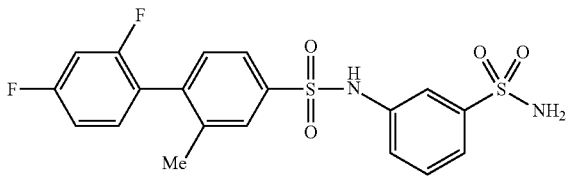

Using a method analogous to Method B, using ABD866a and 2,4-difluorobenzeneboronic acid, the title compound was obtained as a brown oil, contaminated with a small amount of ABD866a.

Synthesis 75

2',3'-Dimethoxy-N-(3-sulfamoylphenyl)biphenyl-4-sulfonamide (ABD867)

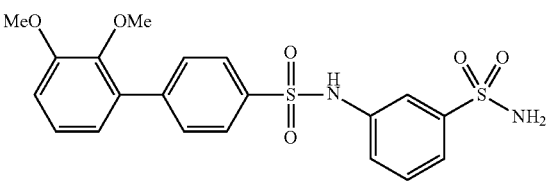

Using a method analogous to Method B, using ABD751a and 2,3-dimethoxybenzeneboronic acid, a brown oil was obtained. The oil was dissolved in DCM and crystallised by addition of petrol to give the title compound as pale brown crystals. $^1$H NMR (250 MHz, DMSO-d$_6$): δ 3.52 (3H, s), 3.84 (3H, s), 6.92 (1H, m), 7.13 (2H, m), 7.34 (1H, m), 7.45 (4H, m), 7.66 (3H, m), 7.86 (2H, d, J=7.9 Hz) and 10.77 (1H, s).

Synthesis 76

3'-Methoxy-N-(3-sulfamoylphenyl)biphenyl-4-sulfonamide (ABD869)

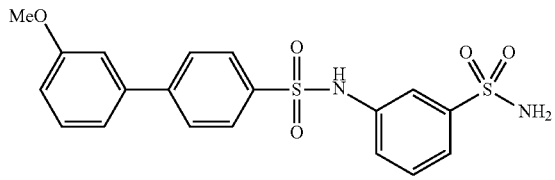

Using a method analogous to Method B, using ABD751a and 3-methoxybenzeneboronic acid, a brown oil was obtained. The oil was dissolved in DCM and crystallised by addition of petrol to give the title compound as pale brown crystals. $^{13}$C NMR (DMSO-d$_6$): δ 55.2, 112.3, 114.5, 116.4, 119.6, 121.2, 122.9, 127.5, 127.9, 130.0, 130.3, 138.1, 138.3, 139.7, 144.5, 145.1 and 159.8. $^1$H NMR (DMSO-d$_6$): δ 3.80 (3H, s), 6.98 (1H, d), 7.22-7.47 (7H, m), 7.66 (1H, s) and 7.87 (4H, m).

Synthesis 77

4-Bromo-2-chloro-N-(3-sulfamoylphenyl)benzenesulfonamide (ABD870a)

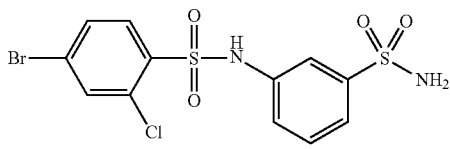

Using a method analogous to Method E, using 4-bromo-2-chlorobenzenesulfonyl chloride and 3-aminobenzenesulfonamide, the title compound was obtained as a white solid.

Synthesis 78

3-Chloro-N-(3-sulfamoylphenyl)-4'-(trifluoromethoxy)biphenyl-4-sulfonamide (ABD870)

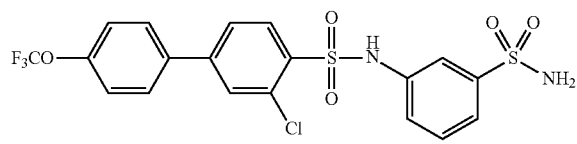

Using a method analogous to Method B, using ABD870a and 4-trifluoromethoxybenzeneboronic acid, a brown oil was obtained. The oil was purified by column chromatography and then pumped under vacuum to give the title compound as an amorphous white solid. $^1$H NMR (DMSO-d$_6$): δ 7.30 (1H, m), 7.40-7.49 (4H, m), 7.63 (1H, s), 7.83 (1H, m), 7.89 (2H, d, J=8.5 Hz), 7.98 (1H, s), 8.16 (1H, d, J=8.5 Hz) and 11.17 (1H, br s).

Synthesis 79

4'-Methyl-N-(3-sulfamoylphenyl)biphenyl-4-sulfonamide (ABD871)

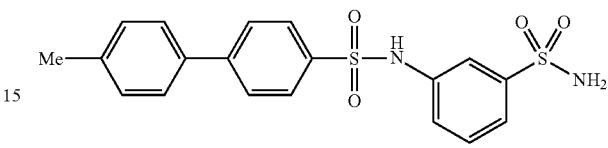

Using a method analogous to Method B, using ABD751a and 4-methylbenzeneboronic acid an off-white solid was obtained. The solid was washed with DCM to give the title compound as a white solid. $^1$H NMR (DMSO-d$_6$): δ 2.33 (3H, s), 7.29 (3H, m), 7.44 (4H, m), 7.60 (1H, d, J=8.2 Hz), 7.66 (1H, s) and 7.84 (4H, m). $^{13}$C NMR (DMSO-d$_6$): δ 20.7, 116.1, 121.7, 122.3, 126.8, 127.2, 127.4, 129.7, 129.9, 135.3, 137.6, 138.3, 138.3, 144.5 and 145.1.

Synthesis 80

3-Chloro-N-(3-sulfamoylphenyl)-3',5'-bis(trifluoromethyl)biphenyl-4-sulfonamide (ABD872)

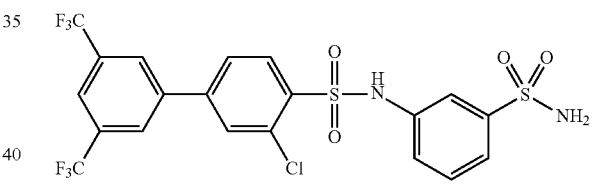

Using a method analogous to Method B, using ABD870a and 3,5-bis(trifluoromethyl)benzeneboronic acid, the title compound was obtained as a white solid. $^1$H NMR (DMSO-d$_6$): 7.32 (1H, m), 7.43 (4H, m), 7.65 (1H, s), 8.03 (1H, d, J=8.2 Hz), 8.20 (3H, m), 8.46 (2H, s), and 11.19 (br s).

Synthesis 81

3',4'-Difluoro-N-(3-sulfamoylphenyl)biphenyl-4-sulfonamide (ABD873)

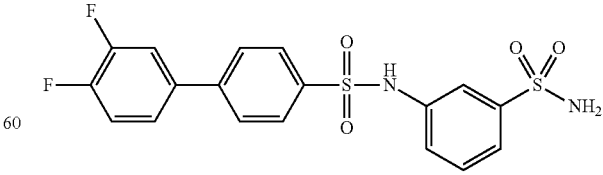

Using a method analogous to Method B, using ABD751a and 3,4-difluorobenzeneboronic acid an off-white solid was obtained. The solid was washed with DCM to give the title compound as a white solid. $^{13}$C NMR (DMSO-d$_6$): δ 116.1, 116.4, 118.2, 121.6, 122.2, 124.0, 127.3, 127.5, 130.0, 135.7 (d, J=3.9 Hz), 138.2, 138.5, 142.3, 145.1, 147.8 (d, J=14.7 Hz) and 151.7 (d, J=12.7 Hz). $^1$H NMR (DMSO-d$_6$): δ 7.35-7.57 (6H, m), 7.66 (1H, s) and 7.88 (4H, m).

Synthesis 82

2'-Chloro-N-(3-sulfamoylphenyl)biphenyl-4-sulfonamide (ABD874)

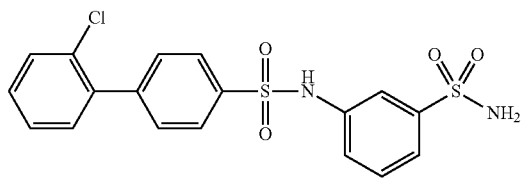

Using a method analogous to Method B, using ABD751a and 2-chlorobenzeneboronic acid an off-white solid was obtained. The solid was washed with DCM to give the title compound as a white solid. $^{13}$C NMR (DMSO-d$_6$): δ 116.5, 121.0, 122.3, 126.5, 126.7, 127.5, 130.0, 130.2, 130.8, 131.1, 131.3, 138.1, 138.3, 138.6, 143.2 and 145.1. $^1$H NMR (DMSO-d$_6$): δ 6.60 (1H, s), 7.42-7.65 (9H, m), 7.63 (2H, d, J=8.2 Hz) and 7.90 (2H, d, J=6.4 Hz).

Synthesis 83

2,4-Difluoro-3'-methylbiphenyl (ABD875c)

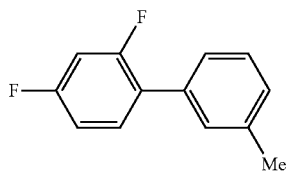

Using a method analogous to Method B, using 3-bromotoluene and 2,4-difluorobenzene boronic acid, the title compound was obtained as a clear oil.

Synthesis 84

2',4'-Difluoro-3-methylbiphenyl-4-sulfonic acid (ABD875b)

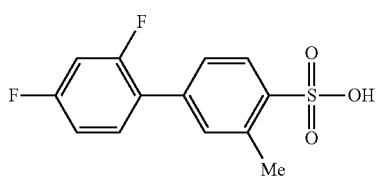

ABD875c (2 g) was dissolved in chloroform (30 mL). Chlorosulfonic acid (2 mL) was added and the mixture stirred at room temperature for 5 hours. The chloroform was allowed to evaporate in a fume cupboard until separation of a dark oil was seen. The chloroform was decanted and the oil washed with further chloroform. The chloroform fractions were combined and left to stand, with the solvent intermittently decanted from any oil that separated. On further standing the title compound precipitated from the chloroform as large white crystals.

Synthesis 85

2',4'-Difluoro-3-methylbiphenyl-4-sulfonyl chloride (ABD875a)

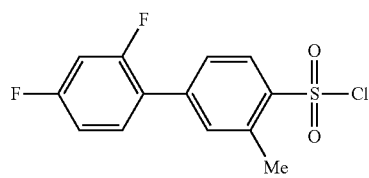

ABD875b (1.8 g) was refluxed in thionyl chloride (20 mL) containing a catalytic quantity of DMF, for 5 hours. The solvents were evaporated with addition of toluene, and the title compound obtained as a pale yellow oil.

Synthesis 86

2'-4'-Difluoro-3-methyl-N-(3-sulfamoylphenyl)biphenyl-4-sulfonamide (ABD875)

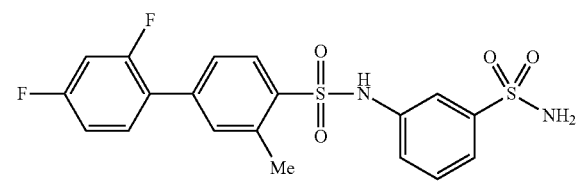

Using a method analogous to Method A, using ABD875a and 3-aminobenzenesulfonamide, the title compound was obtained as a clear thick oil. $^1$H NMR (DMSO-d$_6$): δ 2.66 (3H, s), 7.20 (1H, m), 7.28 (1H, m), 7.40 (2H, m), 7.42 (4H, d, J=8.2 Hz), 7.52-7.62 (4H, m), 8.02 (1H, d, J=8.2 Hz) and 10.92 (1H, br s).

Synthesis 87

N-(3-Sulfamoylphenyl)biphenyl-4-sulfonamide (ABD879)

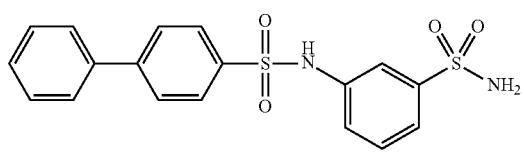

Using a method analogous to Method A, using biphenyl sulfonyl chloride and 3-aminobenzenesulfonamide, the title compound was obtained as a white solid. $^1$H NMR (DMSO-d$_6$): δ 7.34 (1H, d, J=7.6 Hz), 7.43-7.48 (7H, m), 7.69 (2H, m), 7.70 (1H, d, J=7.3 Hz), 7.88 (4H, m) and 10.79 (1H, br s).

Synthesis 88

3-(4-Bromophenylsulfonamido)-2-methylbenzoic acid (ABD882d)

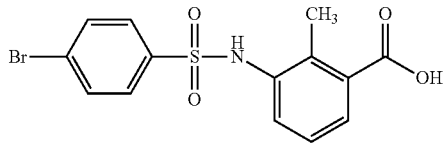

The title compound was prepared using a method analogous to Method A, using 4-bromobenzene sulfonyl chloride, 3-amino-2-methylbenzoic acid, and a large excess of pyridine. The title compound was precipitated on partition of the reaction mixture between dilute HCl and DCM. The precipitate was collected by filtration, dissolved in ethyl acetate and dried. Evaporation of the solvent gave the title compound as a pale brown solid.

Synthesis 89

3-(4-Bromophenylsulfonamido)-2-methylbenzoyl chloride (ABD882c)

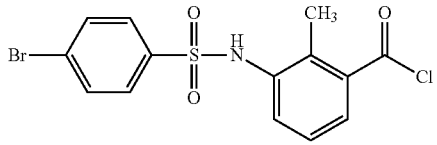

ABD880d (4 g) was suspended in toluene (30 mL) and refluxed in the presence of thionyl chloride (10 mL) overnight. The solvents were evaporated to give the title compound as a pale yellow oil which solidified on standing.

Synthesis 90

3-(4-Bromophenylsulfonamido)-N,N-diethyl-2-methylbenzamide (ABD882b)

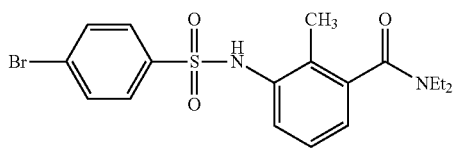

ABD880c (1 g) was dissolved in THF (20 mL) and chilled to 0° C. Diethylamine (4 ml) was added and a precipitate formed. The mixture was stirred for a further 4 hours, poured into dilute HCl and extracted with ethyl acetate. The organic was washed with water, dried and evaporated to give an oil. Trituration with ether gave the title compound as a white powder.

Synthesis 91

3-(2',4'-Difluorobiphenyl-4-ylsulfonamido)-N,N-diethyl-2-methylbenzamide (ABD882a)

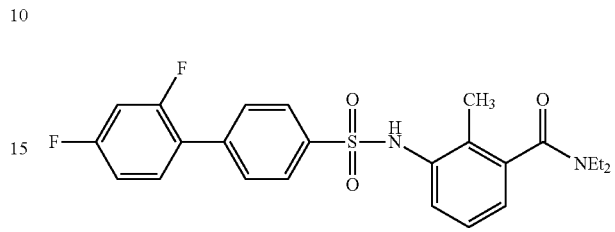

Using a method analogous to Method B, using ABD882b and 2,4-difluorobenzene boronic acid, the title compound was obtained as a pale brown solid. $^1$H NMR (DMSO-d$_6$): δ 0.84 (3H, t, J=7.0 Hz), 1.07 (3H, t, J=7.0 Hz), 1.82 (3H, s), 2.81 (1H, m), 2.95 (1H, m), 3.22 (1H, m), 3.58 (1H, m), 7.00 (1H, d, J=7.3 Hz), 7.11 (1H, d, J=7.6 Hz), 7.18 (1H, d, J=7.6 Hz), 7.24 (1H, d, J=7.6 Hz), 7.41 (1H, t, J=9.1 Hz), 7.62 (1H, q, J=8.5 Hz), 7.72 (4H, m) and 9.83 (1H, s).

Synthesis 92

N-(3-((Diethylamino)methyl)-2-methylphenyl)-2',4'-difluorobiphenyl-4-sulfonamide (ABD882)

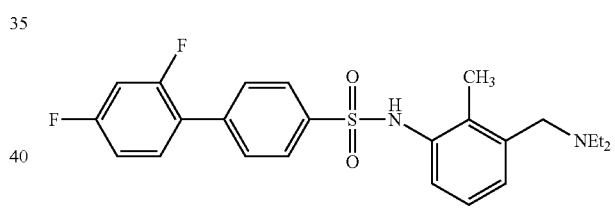

ABD882a (0.5 g) was dissolved in dry THF and stirred at room temperature under N$_2$. LiAlH$_4$ 1 M in THF (5 mL) was added and the mixture stirred overnight, by which time all of the starting material had been consumed. Saturated NH$_4$Cl (20 mL) was added slowly and the mixture extracted with ethyl acetate and dried. Purification by column chromatography gave the title compound as a pale brown oil. $^{13}$C NMR (DMSO-d$_6$): δ 11.4, 13.1, 46.1, 55.9, 104.8, 112.3, 116.0, 123.4 (dd, J=12.7, 3.9 Hz), 125.6, 127.0, 128.3, 129.5, 132.2, 134.3, 134.8, 138.3, 139.1, 139.9, 159.2 (dd, J=250.0, 12.7 Hz) and 162.3 (dd, J=248.0, 11.7 Hz). $^1$H NMR (DMSO-d$_6$): δ 0.88 (6H, t, J=7.0 Hz), 2.00 (3H, s), 2.95 (4H, q, J=7.0 Hz), 3.38 (2H, hidden), 6.90 (1H, d, J=7.9 Hz), 7.03 (1H, t, J=7.9 Hz), 7.13 (1H, d, J=7.0 Hz), 7.21 (1H, t, J=7.9 Hz), 7.39 (1H, t, J=9.1 Hz), 7.70 (5H, m) and 9.65 (1H, s).

Biological Methods

Initial screening of candidate compounds was performed using in vitro assays to determine potency, metabolic stability and solubility in biologically relevant fluids. Potency was assessed using a viability assay based on the survival of the J774 macrophage cell line. Macrophages are closely related to osteoclasts and have been used previously as a model system for osteoclast survival (see, e.g., Luckman et al., 1998). Like osteoclasts, J774 macrophages are dependent on continued NFκB activation for survival, thereby providing a valuable screen for compounds with anti-inflammatory activity. Metabolic stability was measured by determining the rate of disappearance of compound in the presence of human liver microsomal preparations, as quantified by LC-MS/MS. Solubility was measured by equilibration of the compound in fasted state simulated intestinal fluid (FaSSIF) and quantified by HPLC.

Alamar Blue Macrophage J774 Viability Assay

In vitro potency as anti-inflammatory agents was determined for a number of APSAP compounds by incubation with J774 macrophages and subsequent determination of cell viability.

J774 cells were plated at $10^4$ cells per well in 100 μL αMEM (α Modified Eagle Medium) in 96-well plates and grown overnight. The next day, test compounds were added to the cultures, and cultures were continued for another 72 hours. At the end of the culture period, cell survival was determined using an Alamar Blue assay as previously described (see, e.g., Nociari et al., 1998).

Alamar Blue is an oxidation-reduction sensitive indicator. The dye itself is in the oxidised state, which is blue and non-fluorescent. The dye can accept electrons from reducing species, such as NADPH and FADH, to form a reduced dye species, which is red and fluorescent. Thus the transformation from oxidised form to reduced form can be measured by fluorimetric or colourimetric means. For fluorescence measurements, 530-560 nm excitation and 590 nm emission wavelengths are typically used. For colourimetric measurements, absorbance at 570 nm (reduced form) and 600 nm (oxidised form) is typically measured. A simple calculation is performed to determine the relative quantities of the two species.

A high ratio of the reducing species, NADPH and FADH, to the corresponding oxidised species, NADP and FAD, is an indicator that cells are proliferating and viable. A low ratio indicates cells that are quiescent or non-viable.

Briefly, Alamar Blue (Biosource International) was added undiluted to each well (1:10 v/v, 10 μL). The plate was incubated at 37° C. for 3-4 hours and the fluorescence was measured at 590 nm, with a 25 nm bandwidth. A high reading indicated cells with normal viability, and a low reading indicated cells that have been damaged and are no longer proliferating normally. The controls gave a high fluorescence reading, indicating a high number of live, healthy cells. A potent test compound gave a low fluorescence reading.

The average results for each test compound (n=5) were expressed as a percent (%) of the average control value.

Addition of Compounds. All of the compounds studied were made up as 100 mM solutions in DMSO. These stock solutions were then diluted 1000-10000× in culture medium (αMEM). From these 100 μM or 10 μM solutions, convenient quantities (3-33 μL) were added directly to the wells so as to give the desired final compound concentration.

This assay offers numerous advantages over other assays, including MTT assays: it permits a higher throughput; it is more sensitive; it is non-damaging to the cells; it is faster; and it generally gives an identical result to MTT assays.

Aqueous Solubility Measurements

Thermodynamic aqueous solubility was measured by equilibration of a number of APSAP compounds, in the solid state, with fasted state simulated intestinal fluid (FaSSIF) and quantified by HPLC. Measurement of solubility in FaSSIF provides a valuable model for the prediction of drug dissolution following oral administration.

FaSSIF was prepared as described below:

Preparation of blank FaSSIF: NaOH pellets (174 mg), $NaH_2PO_4 \cdot 2H_2O$ (2.235 g), and NaCl (3.093 g) were dissolved in 500 mL of water. The pH was adjusted to 6.5 using 1 M NaOH solution.

Preparation of FaSSIF: Sodium taurocholate (165 mg) was dissolved in 25 mL blank FaSSIF. 0.6 mL of a solution containing 100 mg/mL lecithin in methylene chloride was added. The methylene chloride was eliminated under vacuum at about 40° C. The vacuum was drawn for 15 minutes at 250 mbar, followed by 15 minutes at 100 mbar. This resulted in a clear, micellar solution, having no perceptible odour of methylene chloride. After cooling to room temperature, the solution was then adjusted to 100 mL with blank FaSSIF.

Aqueous solubility was determined by suspending separately sufficient compound in the FaSSIF to give a maximum final concentration of ≧10 mg/mL of the parent free-form of the compound. The suspension was equilibrated at 25° C. for 24 hours, and then the pH was measured. The suspension was then filtered through a glass fibre C filter into a 96-well plate. The filtrate was then diluted by a factor of 100. Quantification was made by HPLC with reference to a standard solution of compound at approximately 0.1 mg/mL in DMSO. Different volumes of the standard, diluted and undiluted sample solutions were injected. The solubility was calculated using the peak areas determined by integration of the peak found at the same retention time as the principal peak in the standard injection. Detection conditions are shown in the table below. Analysis was performed on an Agilent HP1100 series system equipped with a diode array detector and using ChemStation software vB.02.01-SR1.

TABLE 1

HPLC Method Parameters for Solubility Measurements

| Type of method: | Reverse phase with gradient elution |
| --- | --- |
| Column: | Phenomenex Luna, C18 (2) 5 μm 50 × 4.6 mm |
| Column Temperature (° C.): | 25 |
| Standard Injections (μL): | 1, 2, 3, 5, 7, 10 |
| Test Injections (μL): | 1, 2, 3, 10, 20, 50 |
| Detection: Wavelength, Bandwidth (nm): | 260, 80 |
| Flow Rate (mL/min): | 2 |
| Phase A: | 0.1% TFA in water |
| Phase B: | 0.085% TFA in acetonitrile |

| Timetable: | Time (min) | % Phase A | % Phase B |
| --- | --- | --- | --- |
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Human Liver Microsomal Stability Assay

Metabolic stability of APSAP derivatives was measured by determination of the rate of compound disappearance when incubated in the presence of human liver microsomes. Liver microsomes are prepared from the endoplasmic reticulum of hepatocytes and are the primary source of the most important enzymes (cytochrome P450) involved in drug metabolism. Study of drug stability in the presence of liver microsomes is accepted as a valuable model permitting rapid prediction of in vivo drug stability.

Protocol Summary:

Human liver microsomes were obtained from a commercial source. Test compounds (3 μM) were incubated with pooled liver microsomes (male and female). Samples were incubated for a 45 minute period and removed at 5 time points and test compounds were analysed by LC-MS/MS.

Microsomes (final protein concentration 0.5 mg/mL), 0.1 M phosphate buffer pH 7.4, and test compound (final concentration 3 μM; diluted from 10 mM stock solution to give a final DMSO concentration of 0.25%) were incubated at 37° C. prior to the addition of NADPH (final concentration 1 mM) to initiate the reaction. The final incubation volume was 25 μL. A control incubation was included for each compound tested, where 0.1 M phosphate buffer pH 7.4 was added instead of NADPH. The control compounds testosterone and 7-hydroxycoumarin were included in each experiment and all incubations were performed singularly for each compound.

Each compound was incubated for 0, 5, 15, 30, and 45 minutes. The control (minus NADPH) was incubated for 45 minutes only. The reactions were stopped by the addition of 50 μL methanol containing internal standard at the appropriate time points. The incubation plates were centrifuged at 2500 rpm for 20 minutes at 4° C. to precipitate the protein.

Quantitative Analysis:

Following protein precipitation, the sample supernatants were combined in cassettes of up to 4 compounds and analysed using standard LC-MS/MS conditions.

Data Analysis:

From a plot of the natural logarithm of the peak area ratio (i.e., the ratio of compound peak area:internal standard peak area) against time, the gradient of the line was determined. Subsequently, half-life and intrinsic clearance were calculated using the equations below:

Eliminated rate constant$(k)$=(−gradient).

Half life$(t_{1/2})$(min)=0.063/$k$.

Intrinsic Clearance$(CL_{int})$(μL/min/million cells)=($V$×0.693)/$t_{1/2}$.

wherein $V$=Incubation volume(μL/mg microsomal protein).

Pharmacokinetics Studies

Absorption and metabolic stability were studied using an in vivo pharmacokinetics assay. Drug levels were assessed using ultra-performance LC/TOF-MS.

Three male Sprague-Dawley rats, 200-300 g, were dosed per route. Test compound was administered either orally or intravenously (dose level of 1 mg/kg body weight). Test compound was formulated in 50:50 tetraethylene glycol:PBS for both routes. Animals were given free access to food throughout the study. On the day prior to dosing, the carotid artery was cannulated for sample collection and for the intravenous study, the jugular vein was cannulated to enable dosing.

Blood samples were taken from the carotid artery at the following time points and placed in heparinised tubes:

Oral dosing—predose, 0.25, 0.5, 1, 2, 4, 8 and 24 hours post dose.

IV dosing—predose, 0.08, 0.25, 0.5, 1, 2, 4 and 8 hours post dose.

After the final time point, the animals were sacrificed by an overdose of anaesthetic.

Blood samples were centrifuged to obtain plasma, which was transferred to a separate container and frozen at −20° C.

Sample Preparation:

Samples were thawed at room temperature and prepared by protein precipitation with acetonitrile in the ratio 1:2 with plasma, followed by centrifugation for 10 minutes at 16,100×g (Eppendorf 5415D, Eppendorf AG, Hamburg, Germany). The supernatants were collected for analysis. The standard samples were prepared similarly, after spiking blank rat plasma samples to study compound concentrations at 1, 2, 5, 10, 20, 50, 100, 200, 500 and 1000 ng/mL. In addition, extra samples were prepared from 0-1 hour i.v. samples by diluting 1/20 with 50% aqueous acetonitrile to avoid exceeding the linear range of the analytical method.

Analytical Methods:

A Waters Acquity liquid ultra-performance chromatographic system (Waters Corp., Milford, Mass., USA) with autosampler, vacuum degasser and column oven was used. The analytical column used for all compounds was a Waters BEH C18, (2.1×50 mm, 1.7 μm, Waters Corp, Milford, Mass., USA) together with a 0.2 μm on-line filter before the column. The eluents were 0.1% acetic acid (A, pH 3.2) and methanol (B). Gradient elution from 5% to 60% B in two minutes was employed, followed by one minute gradient to 90% B and column equilibration. The flow rate was 0.5 mL/min and the column oven temperature was 35° C. The flow was directed to the MS via Water Acquity photo-diode-array (PDA) detector. LC/TOF-MS data were recorded with a Micromass LCT Premier XE time-of-flight (TOF) mass spectrometer (Micromass Ltd., Manchester, England) equipped with a LockSpray electrospray ionization source. A positive ionization mode of electrospray was used for all compounds. The mass range of m/z 100-900 was acquired. The W-option of the reflector was used, and the DRE (dynamic range enhancement) option was set to on. The mass spectrometer and HPLC system were operated under Micromass MassLynx 4.1 software. Leucine enkephalin ([M+H]$^+$ m/z 556.2771) was used as a lock mass compound for accurate mass measurements and was delivered into the LockSpray probe with a syringe pump. MassLynx 4.1 software was used for controlling the instrumentation and for data processing.

Calculations:

The pharmacokinetic parameters for the test compounds were calculated by WinNonlin Pro (Pharsight Corp, CA) using standard noncompartmental methods. The elimination phase half-life ($t_{1/2}$) was calculated by least-squares regression analysis of the terminal linear part of the log concentration–time curve. The area under the plasma concentration–time curve (AUC) was determined by use of the linear trapezoidal rule up to the last measurable concentration and thereafter by extrapolation of the terminal elimination phase to infinity. The tentative oral bioavailability (F) was calculated by dividing the AUC (0-24 hours) after p.o. administration by the AUC (0-8 hours) after i.v. administration, i.e., F=AUC(p.o.)/AUC(i.v), and reported as percentages (%).

Biological Data

Biological Study 1

The biological activity of a number of APSAP compounds was determined and compared with the biological activity of a range of structurally related compounds using the assays described previously.

$IC_{50}$ values were determined for several APSAP compounds, as well as several reference compounds, using the Alamar Blue macrophage J774 viability assay described above. The results are summarised in the following tables.

TABLE 2A

Alamar Blue Macrophage J774 Viability Assay Data (Reference Compounds)

| Compound | $R^{X2}$ | $R^{X4}$ | Q | R | IC$_{50}$ (μM) |
|---|---|---|---|---|---|
| ABD527 | F | F | 5-CH$_2$OH | 6-Me | 0.08 |
| ABD565 | F | F | 5-CH$_2$OH | 4-CH$_2$OH | 0.15 |
| ABD585 | F | F | 5-CH$_2$OH | 2-OH | 0.20 |
| ABD456 | F | F | 5-CH$_2$OH | — | 0.25 |
| ABD575 | F | Cl | 5-CH$_2$OH | — | 0.40 |
| ABD455 | Cl | Cl | 5-CH$_2$OH | — | 0.50 |
| ABD446 | Br | H | 5-CH$_2$OH | — | 2.5 |
| ABD466 | F | F | 4-CH$_2$OH | — | 3.0 |
| ABD612 | Cl | Cl | 5-COOH | — | >50 |

TABLE 2B

Alamar Blue Macrophage J774 Viability Assay Data

| Compound | $R^{X2}$ | $R^{X4}$ | Q | R | IC$_{50}$ (μM) |
|---|---|---|---|---|---|
| ABD707 | Cl | Cl | 5-C(Me)$_2$OH | — | 0.09 |
| ABD708 | Cl | Cl | 5-CH(Me)OH | — | 0.18 |
| ABD709 | Cl | Cl | 5-C(cycloprop-1,1-di-yl)OH | — | 0.38 |
| ABD766 | Cl | Cl | 5-CH(CF$_3$)OH | — | 0.71 |

TABLE 2C

Alamar Blue Macrophage J774 Viability Assay Data

| Compound | $R^{X2}$ | $R^{X4}$ | Q | R | IC$_{50}$ (μM) |
|---|---|---|---|---|---|
| ABD788 | F | F | 5-CH$_2$NH$_2$ | — | 1.00 |
| ABD724 | Cl | Cl | 5-CH$_2$NMe$_2$ | — | 0.30 |
| ABD783 | F | F | 5-CH(OH)CH$_2$NHMe | — | 1.18 |
| ABD784 | F | F | 5-CH(OH)CH$_2$NMe$_2$ | — | 1.43 |
| ABD785 | F | F | 5-CH(OH)CH$_2$-morpholino | — | 4.71 |
| ABD789 | F | F | 5-CH(NHMe)CH$_2$OH | — | 0.14 |
| ABD791 | F | F | 5-CH(NMe$_2$)CH$_2$OH | — | 0.57 |
| ABD792 | F | F | 5-CH(morpholino)CH$_2$OH | — | >30 |
| ABD810 | F | F | 5-CH(R—NHMe)CH$_2$OH | — | 1.02 |
| ABD811 | F | F | 5-CH(S—NHMe)CH$_2$OH | — | 0.35 |
| ABD854 | F | F | 5-CH(R—NH$_2$)CH$_2$OH | — | 1.35 |
| ABD855 | F | F | 5-CH(S—NH$_2$)CH$_2$OH | — | 0.86 |
| ABD862 | F | F | 5-CH(NH$_2$)(CH$_3$)CH$_2$OH | — | 2.43 |
| ABD751 | Cl | Cl | 5-SO$_2$NH$_2$ | — | 0.87 |

These data demonstrate that it is possible to modify the benzyl alcohol (i.e., where Q is —CH$_2$OH), by way of further substitution on the methylene group, optionally with extension of the methylene group to an ethylene group; by replacement of the alcohol with an amine; or by a combination of these; without a loss of potency. The data also demonstrate that this replacement is neither trivial nor predictable and can lead either to an increase or a decrease in potency.

Biological Study 2

The metabolic stability of a number of APSAP compounds was determined and compared with the metabolic stability of a range of structurally related compounds using the assays described previously.

Biological half-life values ($t_{1/2}$) were determined for several APSAP compounds, as well as several reference compounds, using the human liver microsomal stability assay described above. The results are summarised in the following tables.

TABLE 3A

Human Liver Microsomal Stability Data (Reference Compounds)

| Compound | $R^{X2}$ | $R^{X4}$ | Q | R | T$_{1/2}$ (min) |
|---|---|---|---|---|---|
| ABD446 | H | Br | 5-CH$_2$OH | — | 42 |
| ABD455 | Cl | Cl | 5-CH$_2$OH | — | 28 |
| ABD456 | F | F | 5-CH$_2$OH | — | 30 |
| ABD466 | F | F | 4-CH$_2$OH | — | 2 |
| ABD527 | F | F | 5-CH$_2$OH | 6-Me | 20 |
| ABD565 | F | F | 5-CH$_2$OH | 4-CH$_2$OH | 14 |
| ABD575 | F | Cl | 5-CH$_2$OH | — | 42 |
| ABD585 | F | F | 5-CH$_2$OH | 2-OH | 38 |
| ABD625 | Cl | Cl | 5-CH$_2$CH$_2$OH | — | 13 |
| ABD628 | F | F | 5-CH$_2$CH$_2$OH | — | 18 |
| ABD630 | H | Br | 5-CH$_2$CH$_2$OH | — | 43 |
| ABD612 | Cl | Cl | 5-COOH | — | Stable |
| ABD746 | Cl | Cl | 5-COCH$_3$ | — | 11 |

TABLE 3B

Human Liver Microsomal Stability Data

| Compound | $R^{X2}$ | $R^{X4}$ | Q | R | T$_{1/2}$ (min) |
|---|---|---|---|---|---|
| ABD707 | Cl | Cl | 5-C(Me)$_2$OH | — | 12 |
| ABD708 | Cl | Cl | 5-CH(Me)OH | — | 6 |
| ABD709 | Cl | Cl | 5-C(cycloprop-1,1-di-yl)OH | — | 18 |
| ABD766 | Cl | Cl | 5-CH(CF$_3$)OH | — | 16 |

TABLE 3C

Human Liver Microsomal Stability Data

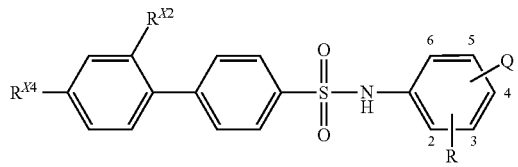

| Compound | $R^{X2}$ | $R^{X4}$ | Q | R | T½ (min) |
|---|---|---|---|---|---|
| ABD788 | F | F | 5-CH$_2$NH$_2$ | — | 60 |
| ABD724 | Cl | Cl | 5-CH$_2$NMe$_2$ | — | 21 |
| ABD728 | Cl | Cl | 5-CONH$_2$ | — | 34 |
| ABD730 | Cl | Cl | 5-CONMe$_2$ | — | 15 |
| ABD783 | F | F | 5-CH(OH)CH$_2$NHMe | — | Stable |
| ABD784 | F | F | 5-CH(OH)CH$_2$NMe$_2$ | — | — |
| ABD785 | F | F | 5-CH(OH)CH$_2$-morpholino | — | 6 |
| ABD789 | F | F | 5-CH(NHMe)CH$_2$OH | — | Stable |
| ABD791 | F | F | 5-CH(NMe$_2$)CH$_2$OH | — | 27 |
| ABD792 | F | F | 5-CH(morpholino)CH$_2$OH | — | 2 |
| ABD855 | F | F | 5-CH(S—NH$_2$)CH$_2$OH | — | 289 |
| ABD751 | Cl | Cl | 5-SO$_2$NH$_2$ | — | 46 |

These data demonstrate that it is possible to modify the benzyl alcohol (i.e., where Q is —CH$_2$OH), by way of further substitution on the methylene group, optionally with extension of the methylene group to an ethylene group; by replacement of the alcohol with an amine; or by a combination of these; without a loss of metabolic stability. The data also demonstrate that this replacement is neither trivial nor predictable and can lead either to an increase or a decrease in metabolic stability. Furthermore, the data show the exceptional stability imparted by the groups —CH(OH)CH$_2$NHMe (e.g., as found in ABD783) and —CH(NHR)CH$_2$OH (e.g., as found in ABD789 and ABD855).

Biological Study 3

The solubility of a number of APSAP compounds was determined and compared with the solubility of a range of structurally related compounds using the assays described previously.

Solubility in the biological model fasted state simulated intestinal fluid (FaSSIF) was determined for several APSAP compounds, as well as several reference compounds, using the aqueous solubility assay described above. The results are summarised in the following tables.

TABLE 4A

Aqueous Solubility Data (Reference Compounds)

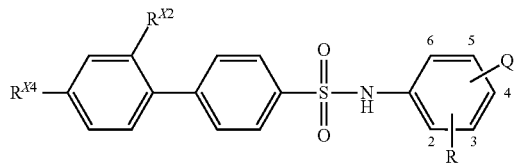

| Compound | $R^{X2}$ | $R^{X4}$ | Q | R | Solubility (mg/mL) |
|---|---|---|---|---|---|
| ABD446 | H | Br | 5-CH$_2$OH | — | 0.02 |
| ABD455 | Cl | Cl | 5-CH$_2$OH | — | 0.04 |
| ABD456 | F | F | 5-CH$_2$OH | — | 0.05 |
| ABD466 | F | F | 4-CH$_2$OH | — | 0.04 |
| ABD527 | F | F | 5-CH$_2$OH | 6-Me | 0.04 |

TABLE 4A-continued

Aqueous Solubility Data (Reference Compounds)

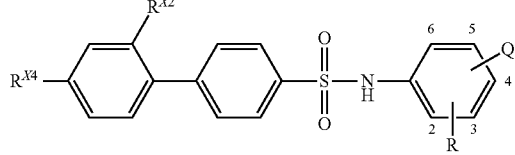

| Compound | $R^{X2}$ | $R^{X4}$ | Q | R | Solubility (mg/mL) |
|---|---|---|---|---|---|
| ABD565 | F | F | 5-CH$_2$OH | 4-CH$_2$OH | 0.03 |
| ABD575 | F | Cl | 5-CH$_2$OH | — | 0.07 |
| ABD585 | F | F | 5-CH$_2$OH | 2-OH | 0.07 |
| ABD630 | H | Br | 5-CH$_2$CH$_2$OH | — | 0.06 |
| ABD615 | Cl | Cl | 5-COOH | — | 0.13 |
| ABD746 | Cl | Cl | 5-COCH$_3$ | — | 0.008 |

TABLE 4B

Aqueous Solubility Data

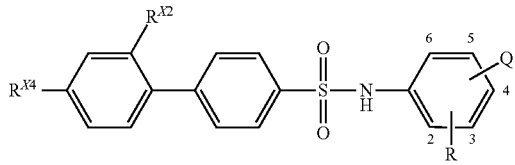

| Compound | $R^{X2}$ | $R^{X4}$ | Q | R | Solubility (mg/mL) |
|---|---|---|---|---|---|
| ABD707 | Cl | Cl | 5-C(Me)$_2$OH | — | 0.14 |
| ABD708 | Cl | Cl | 5-CH(Me)OH | — | 0.10 |
| ABD766 | Cl | Cl | 5-CH(CF$_3$)OH | — | 0.02 |
| ABD709 | Cl | Cl | 5-C(cycloprop-1,1-di-yl)OH | — | 0.07 |

TABLE 4C

Aqueous Solubility Data

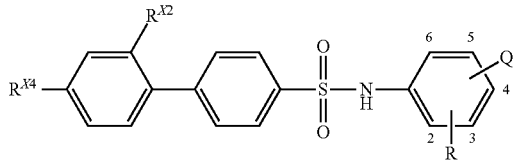

| Compound | $R^{X2}$ | $R^{X4}$ | Q | R | Solubility (mg/mL) |
|---|---|---|---|---|---|
| ABD788 | F | F | 5-CH$_2$NH$_2$ | — | 0.05 |
| ABD724 | Cl | Cl | 5-CH$_2$NMe$_2$ | — | 0.09 |
| ABD728 | Cl | Cl | 5-CONH$_2$ | — | 0.02 |
| ABD730 | Cl | Cl | 5-CONMe$_2$ | — | 0.02 |
| ABD783 | F | F | 5-CH(OH)CH$_2$NHMe | — | 0.37 |
| ABD784 | F | F | 5-CH(OH)CH$_2$NMe$_2$ | — | — |
| ABD785 | F | F | 5-CH(OH)CH$_2$-morpholino | — | 0.21 |
| ABD789 | F | F | 5-CH(NHMe)CH$_2$OH | — | 0.52 |
| ABD791 | F | F | 5-CH(NMe$_2$)CH$_2$OH | — | 3.0 |
| ABD792 | F | F | 5-CH(morpholino)CH$_2$OH | — | 4.4 |
| ABD855 | F | F | 5-CH(S—NH$_2$)CH$_2$OH | — | 4.1 |
| ABD751 | Cl | Cl | 5-SO$_2$NH$_2$ | — | 0.04 |

These data demonstrate that it is possible to modify the benzyl alcohol (i.e., where Q is —CH$_2$OH), by way of further substitution on the methylene group, optionally with extension of the methylene group to an ethylene group; by replacement of the alcohol with an amine; or by a combination of these; without a loss of aqueous solubility. The data also demonstrate that this replacement is neither trivial nor predictable and can lead either to an increase or a decrease in aqueous solubility. Furthermore, the data show the exceptional aqueous solubility imparted by the groups —CH(OH)CH$_2$NHMe (e.g., as found in ABD783), —CH(NHMe)CH$_2$OH (e.g., as found in ABD789), —CH(NMe$_2$)CH$_2$OH (e.g. as found in ABD791) and —CH(NH$_2$)CH$_2$OH (e.g., as found in ABD855).

Biological Study 4

The oral absorption of the APSAP compound, ABD789, was determined in a rat model as described previously.

ABD789

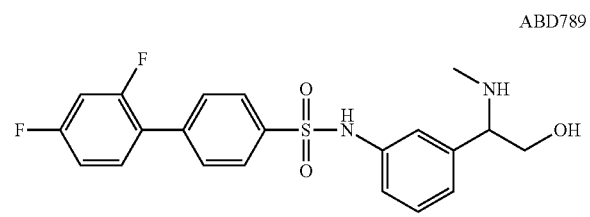

Figure 2:
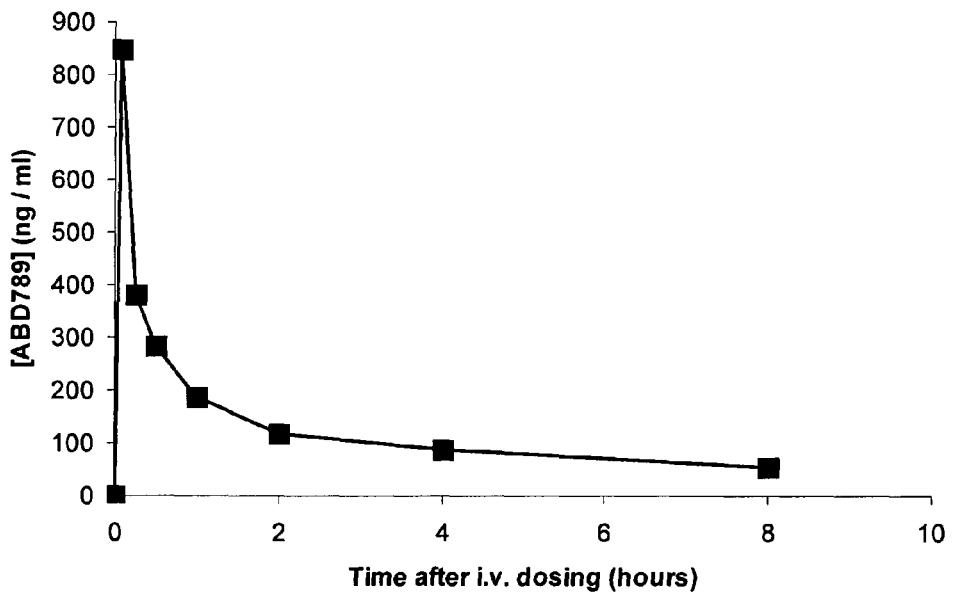
FIG. 2 is a graph showing mean plasma concentration (ng/mL) of the APSAP compound ABD789 (■) after intravenous administration (1 mg/kg) to a rat model.

Serum levels of ABD789, following oral or intravenous dosage (1 mg/kg) (see FIGS. 1 and 2 respectively), were investigated in vivo in rats using an ultra-performance LC/TOF-MS detection system, as described previously. The pharmacokinetic data are summarised in the following table.

TABLE 5

Pharmacokinetic data

|  | ABD789 (1 mg/kg) | | Reference Compound ABD455 (2.5 mg/kg) | |
| --- | --- | --- | --- | --- |
|  | p.o. | i.v. | p.o. | i.v. |
| Bioavailability F % | 38 | | 3 | |
| AUC (ng/mL/min) | 1500 | 11900 | 1.2 | 9 |
| T½ (h) | 3.17 | 0.81 | 0.8 | 0.53 |

Figure 3:
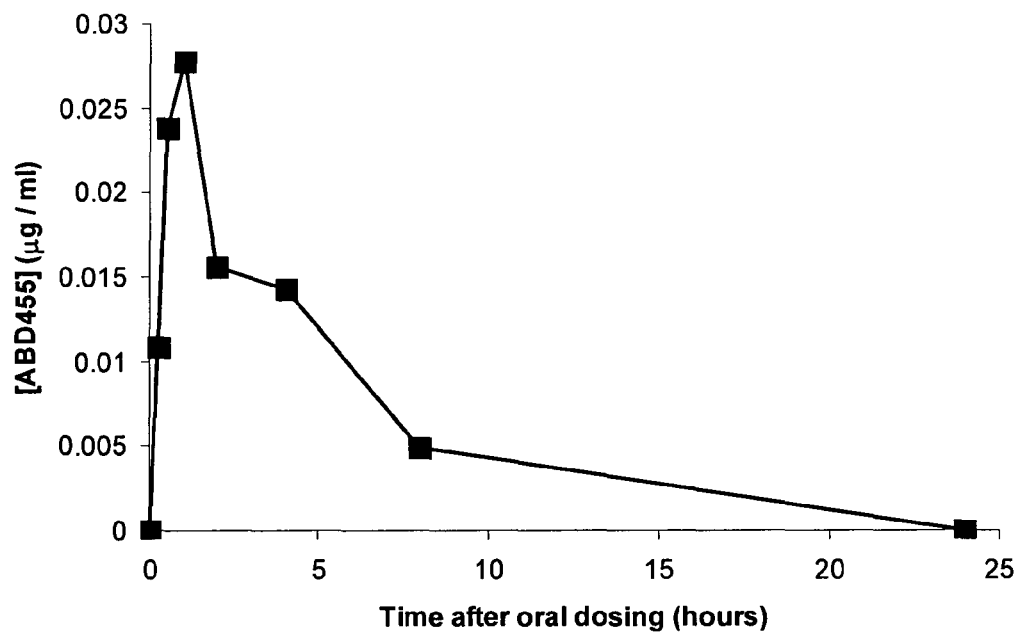
FIG. 3 is a graph showing mean plasma concentration (μg/mL) of the reference compound ABD455 (■) after oral administration 2.5 mg/kg to a rat model.
Figure 4:
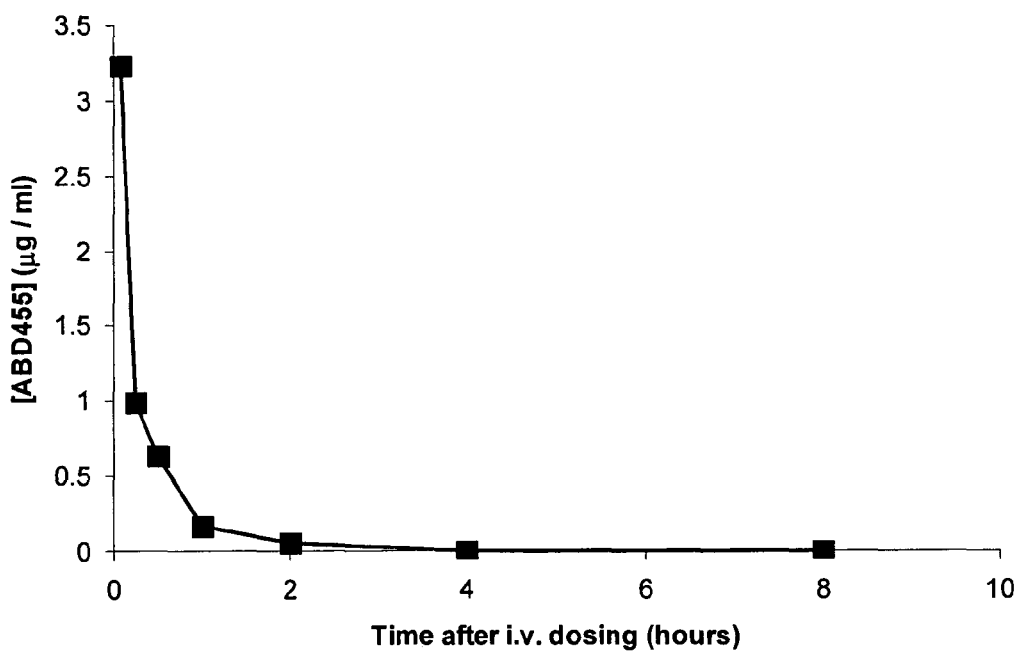
FIG. 4 is a graph showing mean plasma concentration (μg/mL) of the reference compound ABD455 (■) after intravenous administration 2.5 mg/kg to a rat model

The data show that ABD789 is well absorbed following oral administration with a bioavailability (F) of 38% and an extended half life of 7.67 hour, and is superior to the reference compound ABD455 (see FIGS. 3 and 4 and Table 5). Thus, the APSAP compound, ABD789, demonstrates the properties required for an orally active drug.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Baud et al., 1999, "Signaling by proinflammatory cytokines: oligomerization of TRAF2 and TRAF6 is sufficient for JNK and IKK activation and target gene induction via an amino-terminal effector domain", *Genes Dev.*, Vol. 13, pp. 1297-1308.

Baud et al., 2009, "Is NFκB a good target for cancer therapy? Hopes and pitfalls", *Nat. Rev. Drug Disc.*, Vol. 8, pp. 33-40.

Brennan et al., 1989, "Inhibitory effect of TNF alpha antibodies on synovial cell interleukin-1 production in rheumatoid arthritis", *Lancet*, Vol. 2, pp. 244-247.

Brennan et al., 1996, "Cytokines in autoimmunity", *Curr. Opin. Immunol.*, Vol. 8, pp. 872-877.

Brennan et al., 1992, "Enhanced expression of tumor necrosis factor receptor mRNA and protein in mononuclear cells isolated from rheumatoid arthritis synovial joints", *Eur. J. Immunol.*, Vol. 22, pp. 1907-1912.

Elliott et al., 1994, "Randomised double-blind comparison of chimeric monoclonal antibody to tumour necrosis factor alpha (cA2) versus placebo in rheumatoid arthritis", *Lancet*, Vol. 344, pp. 1105-1110.

Feldmann et al., 1994, "TNF alpha as a therapeutic target in rheumatoid arthritis," *Circ. Shock*, Vol. 43, pp. 179-184.

Feldmann et al., 2001, "The role of TNF alpha and IL-1 in rheumatoid arthritis," *Curr. Dir. Autoimmun.*, Vol. 3, pp. 188-199.

Feldmann et al., 1996, "Rheumatoid arthritis", *Cell*, Vol. 85, pp. 307-310.

Firestein, 1996, "Invasive fibroblast-like synoviocytes in rheumatoid arthritis. Passive responders or transformed aggressors?", *Arthritis Rheum.*, Vol. 39, pp. 1781-1790.

Firestein, 2005 "Immunologic mechanisms in the pathogenesis of rheumatoid arthritis", *J. Clin. Rheumatol.*, Vol. 11. pp. S39-S44.

Firestein et al., 1999, "Signal transduction and transcription factors in rheumatic disease", *Arthritis Rheum.*, Vol. 42, pp. 609-621.

Gottlieb, 2005, "Psoriasis: Emerging Therapeutic Strategies", *Nat. Rev. Drug Disc.*, Vol. 4, pp. 19-34.

Greig et al., 2006, "Development and characterization of biphenylsulfonamides as novel inhibitors of bone resorption". *J. Med. Chem.*, Vol 49, pp 7487-7492.

Greig et al., 2004, "Alkyl aryl sulfonamides as therapeutic agents for the treatment of bone conditions". Published international application publication number WO 2005/118528.

Greig et al., 2008, "Biphenyl-4-yl-sulfonic acid arylamides and Their Use as Therapeutic Agents", International patent publication number WO 2008/114022 (application number PCT/GB2008/000989) published 25 Sep. 2008.

Jin et al., 2004, "CCR8Antagonists", International patent publication number WO 2004/073619 A2 published 2 Sep. 2004.

Jimi et al., 2004, "Selective inhibition of NF-kappa B blocks osteoclastogenesis and prevents inflammatory bone destruction in vivo", *Nat. Med.*, Vol. 10, pp. 617-624.

Joosten et al., 1996, "Anticytokine treatment of established type II collagen-induced arthritis in DBA/1 mice. A comparative study using anti-TNF alpha, anti-IL-1 alpha/beta, and IL-1Ra," *Arthritis Rheum.*, Vol. 39, pp. 797-809.

Klareskog et al., 2006, "A long-term, open-label trial of the safety and efficacy of etanercept (Enbrel) in patients with

The invention claimed is:

1. A compound selected from compounds of the following formula, and pharmaceutically acceptable salts thereof:

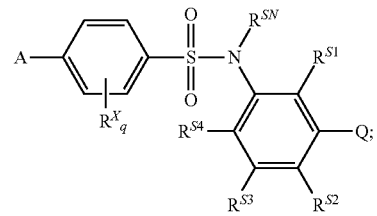

wherein:
-A is:

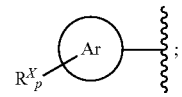

-Ar is independently phenyl, pyridinyl, or pyrimidinyl;
p is independently an integer from 0 to 3;
q is independently an integer from 0 to 3;
—$R^{SN}$ is independently —H or saturated aliphatic $C_{1-4}$alkyl;
—$R^{S1}$ is independently —H or saturated aliphatic $C_{1-4}$alkyl;
—$R^{S2}$ is independently —H or saturated aliphatic $C_{1-4}$alkyl;
—$R^{S3}$ is independently —H or saturated aliphatic $C_{1-4}$alkyl;
—$R^{S4}$ is independently —H or saturated aliphatic $C_{1-4}$alkyl;
-Q is independently:

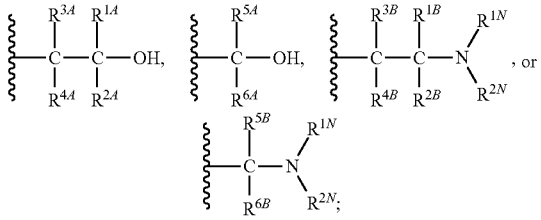

either:
each —$R^{1N}$ is independently —H or —$R^{CN}$;
each —$R^{2N}$ is independently —H or —$R^{CN}$; and
each —$R^{CN}$ is saturated aliphatic $C_{1-4}$alkyl;
or:
—$NR^{1N}R^{2N}$ is independently azetidino, pyrrolidino, imidazolidino, pyrazolidino, piperidino, piperazino, morpholino, thiomorpholino, azepino, or diazepino, each optionally substituted with one or more groups selected from saturated aliphatic $C_{1-4}$alkyl;
—$R^{1A}$ is independently —H, —$R^{C}$, or —$R^{F}$; and
—$R^{2A}$ is independently —H, —$R^{C}$, or —$R^{F}$;
or —$R^{1A}$ and —$R^{2A}$ together form a saturated aliphatic $C_2$alkylene group;
—$R^{3A}$ is independently —$R^{C}$, —$R^{F}$, or —$R^{J}$; and
—$R^{4A}$ is independently —H, —$R^{C}$, or —$R^{F}$;
or —$R^{3A}$ and —$R^{4A}$ together form a saturated aliphatic $C_2$alkylene group;

—$R^{5A}$ is independently —$R^C$ or —$R^F$; and

—$R^{6A}$ is independently —H, —$R^C$, or —$R^F$;

or —$R^{5A}$ and —$R^{6A}$ together form a saturated aliphatic $C_2$alkylene group; —$R^{1B}$ is independently —H, —$R^C$, or —$R^F$; and —$R^{2B}$ is independently —H, —$R^C$, or —$R^F$;

or —$R^{1B}$ and —$R^{2B}$ together form a saturated aliphatic $C_2$alkylene group;

—$R^{3B}$ is independently —H, —$R^C$, —$R^F$, —OH, or —$OR^O$; and

—$R^{4B}$ is independently —H, —$R^C$, or —$R^F$;

or —$R^{3B}$ and —$R^{4B}$ together form a saturated aliphatic $C_2$alkylene group; —$R^{5B}$ is independently —H, —$R^C$, or —$R^F$; and —$R^{6B}$ is independently —H, —$R^C$, or —$R^F$;

or —$R^{5B}$ and —$R^{6B}$ together form a saturated aliphatic $C_2$alkylene group;

each —$R^C$ is saturated aliphatic $C_{1-4}$alkyl;

each —$R^F$ is saturated aliphatic $C_{1-4}$-fluoroalkyl;

—$R^O$ is saturated aliphatic $C_{1-4}$alkyl;

—$R^J$ is independently —$NH_2$, —$NHR^{JN1}$, —$NR^{HN1}_2$, or —$NR^{JN2}R^{JN3}$;

each —$R^{JN1}$ is independently —$R^{J1}$, —$R^{J2}$—OH, —$R^{J2}$—O—$R^{J1}$;

each —$R^{J1}$ is saturated aliphatic $C_{1-4}$alkyl;

each —$R^{J2}$— is saturated aliphatic $C_{2-4}$alkylene;

—$NR^{JN2}R^{JN3}$ is independently azetidino, pyrrolidino, imidazolidino, pyrazolidino, piperidino, piperazino, morpholino, thiomorpholino, azepino, or diazepino, each optionally substituted with one or more groups selected from saturated aliphatic $C_{1-4}$alkyl;

each —$R^X$ is independently —F, —Cl, —Br, —I, —$R^{XX}$, —OH, —$OR^{XX}$, —SH, —$SR^{XX}$, —$CF_3$, —$OCF_3$, —$SCF_3$, —$NH_2$, —$NHR^{XX}$, —$NR^{XX}_2$, —$NR^{YY}R^{ZZ}$, —$C(=O)R^{XX}$, —$OC(=O)R^{XX}$, —$C(=O)OH$, —$C(=O)OR^{XX}$, —$C(=O)NH_2$, —$C(=O)NHR^{XX}$, —$C(=O)NR^{XX}_2$, —$C(=O)NR^{YY}R^{ZZ}$, —$OC(=O)NH_2$, —$OC(=O)NHR^{XX}$, —$OC(=O)NR^{XX}_2$, —$OC(=O)NR^{YY}R^{ZZ}$, —$NHC(=O)R^{XX}$, —$NR^{XX}C(=O)R^{XX}$, —$NHC(=O)OR^{XX}$, —$NR^{XX}C(=O)OR^{XX}$, —$NHC(=O)NH_2$, —$NHC(=O)NHR^{XX}$, —$NHC(=O)NR^{XX}_2$, —$NHC(=O)NR^{YY}R^{ZZ}$, —$NR^{XX}C(=O)NH_2$, —$NR^{XX}C(=O)NHR^{XX}$, —$NHC(=O)NR^{XX}_2$, —$NR^{XX}C(=O)NR^{YY}R^{ZZ}$, —CN, —$NO_2$, —$S(=O)_2NH_2$, —$S(=O)_2NHR^{XX}$, —$S(=O)_2NR^{XX}_2$, —$S(=O)_2NR^{YY}R^{ZZ}$, —$S(=O)R^{XX}$, —$S(=O)_2R^{XX}$, —$OS(=O)_2R^{XX}$, —$S(=O)_2OH$, or —$S(=O)_2OR^{XX}$;

each —$R^{XX}$ is independently saturated aliphatic $C_{1-6}$alkyl, phenyl, or benzyl, wherein said phenyl and benzyl are optionally substituted with one or more groups selected from: —F, —Cl, —Br, —I, —$CF_3$, —$OCF_3$, —$R^{XXX}$, —OH, —$OR^{XXX}$, or —$SR^{XXX}$; wherein each —$R^{XXX}$ is independently saturated aliphatic $C_{1-4}$alkyl; and each —$NR^{YY}R^{ZZ}$ is independently azetidino, pyrrolidino, imidazolidino, pyrazolidino, piperidino, piperazino, morpholino, thiomorpholino, azepino, or diazepino, each optionally substituted with one or more groups independently selected from saturated aliphatic $C_{1-4}$alkyl.

2. A compound according to claim 1, wherein —Ar is phenyl.

3. A compound according to claim 1, wherein -A is:

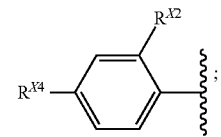

wherein:
—$R^{X2}$ is independently —H or —$R^{X2S}$;
—$R^{X4}$ is independently —H or —$R^{X4S}$;
—$R^{X2S}$ is —$R^X$; and
—$R^{X4S}$ is —$R^X$.

4. A compound according to claim 1, wherein -A is:

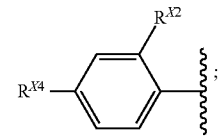

wherein:
—$R^{X2}$ is $R^{X2S}$;
—$R^{X4}$ is —$R^{X4S}$;
—$R^{X2S}$ is —$R^X$; and
—$R^{X4S}$ is —$R^X$.

5. A compound according to claim 4, wherein:

each —$R^X$ is independently —F, —Cl, —Br, —I, —$R^{XX}$, —OH, —$OR^{XX}$, —SH, —$SR^{XX}$, —$CF_3$, —$OCF_3$, —$SCF_3$, —$NH_2$, —$NHR^{XX}$, —$NR^X_2$, —$NR^{YY}R^{ZZ}$, —$C(=O)R^{XX}$, —$OC(=O)R^{XX}$, —$C(=O)OH$, —$C(=O)OR^{XX}$, —$C(=O)NH_2$, —$C(=O)NHR^{XX}$, —$C(=O)NR^{XX}_2$, —$C(=O)NR^{YY}R^{ZZ}$, —CN, —$NO_2$, —$S(=O)_2NH_2$, —$S(=O)_2NH_2$, —$S(=O)_2NR^{XX}_2$, or —$S(=O)_2NR^{YY}R^{ZZ}$; and each —$NR^{YY}R^{ZZ}$ is independently pyrrolidino, piperidino, piperazino, or morpholino, each optionally substituted with one or more groups selected from saturated aliphatic $C_{1-4}$alkyl.

6. A compound according to claim 4, wherein:

—$R^{X2S}$ is independently —F, —Cl, —Br, —I, —$R^{X4}$, —$OR^{X4}$, —$SR^{X4}$, —$CF_3$, or —$OCF_3$, wherein each —$R^{X4}$ is saturated aliphatic $C_{1-4}$alkyl; and —$R^{X4S}$ is independently —F, —Cl, —Br, —I, —$R^{X4}$, —$OR^{X4}$, —$SR^{X4}$, —$CF_3$, or —$OCF_3$, wherein each —$R^{X4}$ is saturated aliphatic $C_{1-4}$alkyl.

7. A compound according to claim 4, wherein:

—$R^{X2S}$ is independently —F or —Cl; and

—$R^{X4S}$ is independently —F or —Cl.

8. A compound according to claim 7, wherein the leading phenylene group:

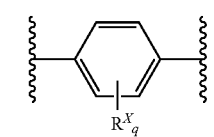

is:

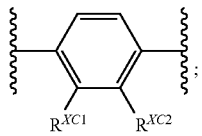

wherein:
—$R^{XC1}$ is independently —H or —$R^{XCC}$; and
—$R^{XC2}$ is —H;
or:
—$R^{XC1}$ is —H; and
—$R^{XC2}$ is independently —H or —$R^{XCC}$;
or:
—$R^{XC1}$ is —H; and
—$R^{XC2}$ is —H;
wherein each —$R^{XCC}$ is independently —F, —Cl, or —$R^{XCCC}$;
wherein each —$R^{XCCC}$ is independently -Me or -Et.

9. A compound according to claim 8, wherein:
either:
each —$R^{1N}$ is independently —H or —$R^{CN}$;
each —$R^{2N}$ is independently —H or —$R^{CN}$; and
each —$R^{CN}$ is saturated aliphatic $C_{1-4}$alkyl;
or:
—$NR^{1N}R^{2N}$ is independently piperidino, piperazino, or morpholino, each optionally substituted with one or more groups selected from saturated aliphatic $C_{1-4}$alkyl;
—$R^{1A}$ is independently —H or —$R^C$;
—$R^{2A}$ is independently —H or —$R^C$;
—$R^{3A}$ is independently —$R^C$ or —$R^J$;
—$R^{4A}$ is independently —H or —$R^C$;
—$R^{5A}$ is —$R^C$;
—$R^{6A}$ is independently —H or —$R^C$;
—$R^{1B}$ is independently —H or —$R^C$;
—$R^{2B}$ is independently —H or —$R^C$;
—$R^{3B}$ is independently —H, —$R^C$, —OH, or —$OR^O$;
—$R^{4B}$ is independently —H or —$R^C$;
—$R^{5B}$ is independently —H or —$R^C$;
—$R^{6B}$ is independently —H or —$R^C$;
each —$R^C$ is saturated aliphatic $C_{1-4}$alkyl;
—$R^O$ is saturated aliphatic $C_{1-4}$alkyl;
—$R^J$ is independently —$NH_2$, —$NHR^{JN1}$, —$NR^{JN1}{}_2$, or —$NR^{JN2}R^{JN3}$;
each —$R^{JN1}$ is —$R^{J1}$;
each —$R^{J1}$ is saturated aliphatic $C_{1-4}$alkyl;
—$NR^{JN2}R^{JN3}$ is independently piperidino, piperazino, or morpholino, each optionally substituted with one or more groups selected from saturated aliphatic $C_{1-4}$alkyl.

10. A compound according to claim 8, wherein:
either:
each —$R^{1N}$ is independently —H or —$R^{CN}$;
each —$R^{2N}$ is independently —H or —$R^{CN}$;
each —$R^{CN}$ is saturated aliphatic $C_{1-4}$alkyl;
or:
—$NR^{1N}R^{2N}$ is independently piperidino, piperazino, or morpholino, each optionally substituted with one or more groups selected from saturated aliphatic $C_{1-4}$alkyl;
—$R^{1A}$ is —H;
—$R^{2A}$ is —H;
—$R^{3A}$ is —$R^J$;
—$R^{4A}$ is —H;
—$R^{5A}$ is —$R^C$;
—$R^{6A}$ is independently —H or —$R^C$;
—$R^{1B}$ is —H;
—$R^{2B}$ is —H;
—$R^{3B}$ is independently —OH or —$OR^O$;
—$R^{4B}$ is —H;
—$R^{5B}$ is —H;
—$R^{6B}$ is —H;
each —$R^C$ is saturated aliphatic $C_{1-4}$alkyl;
—$R^O$ is saturated aliphatic $C_{1-4}$alkyl;
—$R^J$ is independently —$NH_2$, —$NHR^{JN1}$, —$NR^{JN1}{}_2$, or —$NR^{JN2}R^{JN3}$;
each —$R^{JN1}$ is —$R^{J1}$;
each —$R^{J1}$ is saturated aliphatic $C_{1-4}$alkyl;
—$NR^{JN2}R^{JN3}$ is independently piperidino, piperazino, or morpholino, each optionally substituted with one or more groups selected from saturated aliphatic $C_{1-4}$alkyl.

11. A compound according to claim 10, wherein -Q is independently:

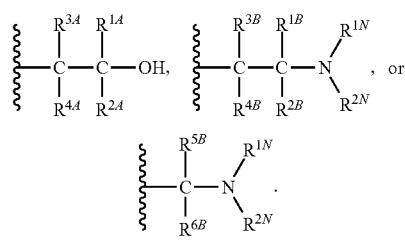

12. A compound according to claim 10, wherein -Q is independently:

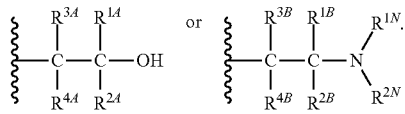

13. A compound according to claim 12, wherein —$R^{SN}$ is —H.

14. A compound according to claim 13, wherein:
—$R^{S1}$ is —H;
—$R^{S2}$ is —H;
—$R^{S3}$ is —H; and
—$R^{S4}$ is —H.

15. A compound according to claim 1, wherein:
-A is:

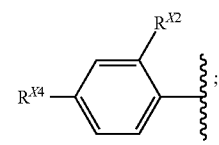

—$R^{X2}$ is independently —F or —Cl;
—$R^{X4}$ is independently —F or —Cl;

the leading phenylene group:

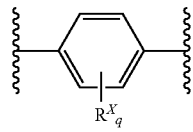

is:

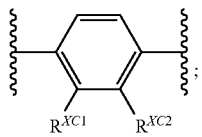

wherein:
—$R^{XC1}$ is independently —H or —$R^{XCC}$; and
—$R^{XC2}$ is —H;
or:
—$R^{XC1}$ is —H; and
—$R^{XC2}$ is independently —H or —$R^{XCC}$;
or:
—$R^{XC1}$ is —H; and
—$R^{XC2}$ is —H;
each —$R^{XCC}$ is —$R^{XCCC}$;
each —$R^{XCCC}$ is -Me; —$R^{SN}$ is —H or -Me; —$R^{S1}$ is —H;
—$R^{S2}$ is —H; —$R^{S3}$ is —H; —$R^{S4}$ is —H;
-Q is:

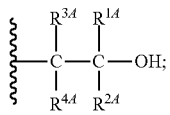

—$R^{1A}$ is —H;
—$R^{2A}$ is —H;
—$R^{3A}$ is —$R^{J}$; and
—$R^{4A}$ is —H.

16. A compound according to claim 15, wherein:
—$R^{X2}$ is —F;
—$R^{XC1}$ is —F;
—$R^{XC1}$ is —H;
—$R^{XC2}$ is H; H and
—$R^{J}$ is independently —NH$_2$, —NHMe, or —NMe$_2$.

17. A compound according to claim 1, wherein:
-A is:

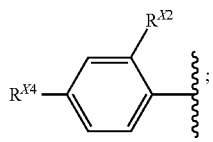

—$R^{X2}$ is independently —F or —Cl;
—$R^{X4}$ is independently —F or —Cl;

the leading phenylene group:

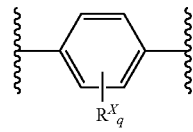

is:

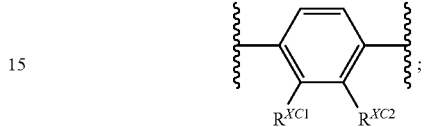

wherein:
—$R^{XC1}$ is independently —H or —$R^{XCC}$; and
—$R^{XC2}$ is —H;
or:
—$R^{XC1}$ is —H; and
—$R^{XC2}$ is independently —H or —$R^{XCC}$;
or:
—$R^{XC1}$ is —H; and
$R^{XC2}$ is —H;
each —$R^{XCC}$ is —$R^{XCCC}$;
each —$R^{XCCC}$ is -Me; —$R^{SN}$ is —H or -Me;
—$R^{S1}$ is —H;
—$R^{S2}$ is —H;
—$R^{S3}$ is —H;
—$R^{S4}$ is —H;
-Q is:

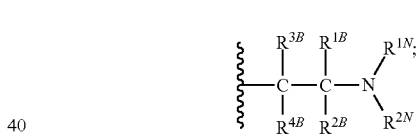

—$R^{1B}$ is —H;
—$R^{2B}$ is —H;
—$R^{3B}$ is independently —OH or —OR$^O$;
—$R^{4B}$ is —H;
each —$R^{1N}$ is independently —H or —$R^{CN}$; and
each —$R^{2N}$ is independently —H or —$R^{CN}$.

18. A compound according to claim 17, wherein:
—$R^{X2}$ is —F;
—$R^{X4}$ is —F;
—$R^{XC1}$ is —H;
—$R^{XC2}$ is —H;
—$R^{3B}$ is —OH; and
each —$R^{CN}$ is -Me.

19. A compound according to claim 1, wherein:
-A is:

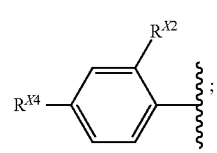

—$R^{X2}$ is independently —F or —Cl;
—$R^{X4}$ is independently —F or —Cl;

the leading phenylene group:

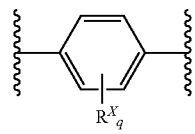

is:

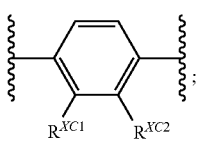

wherein:
—$R^{XC1}$ is independently —H or —$R^{XCC}$; and
—$R^{XC2}$ is —H;
or:
—$R^{XC1}$ is —H; and
—$R^{XC2}$ is independently —H or —$R^{XCC}$;
or:
—$R^{XC1}$ is —H; and
—$R^{XC2}$ is —H;
each —$R^{XCC}$ is —$R^{XCCC}$;
each —$R^{XCCC}$ is -Me;
—$R^{SN}$ is —H or -Me;
—$R^{S1}$ is —H;
—$R^{S2}$ is —H;
—$R^{S3}$ is —H;
—$R^{S4}$ is —H;
-Q is:

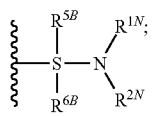

—$R^{5B}$ is —H;
—$R^{6B}$ is —H;
—$R^{1N}$ is independently —H or —$R^{CN}$; and
—$R^{2N}$ is independently —H or —$R^{CN}$.

20. A compound according to claim 19, wherein:
—$R^{CX1}$ is —H;
—$R^{XC2}$ is —H; and
each —$R^{CN}$ is -Me.

21. A compound according to claim 1, selected from the following compounds, and pharmaceutically acceptable salts thereof:

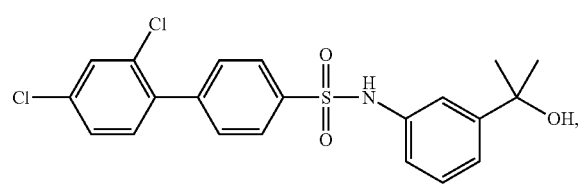
(ABD707)

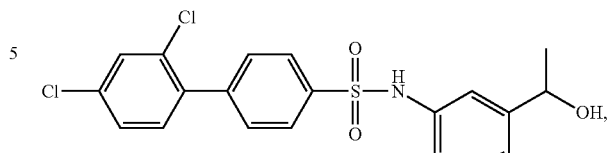
(ABD708)

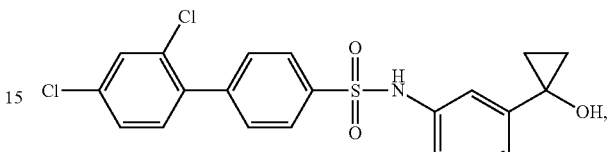
(ABD709)

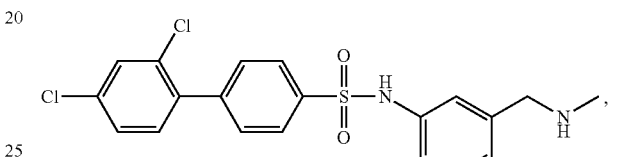
(ABD723)

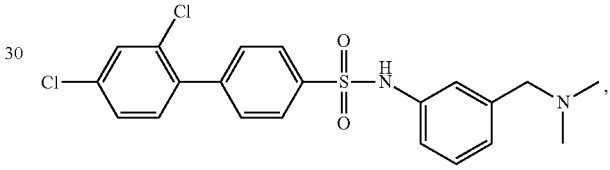
(ABD724)

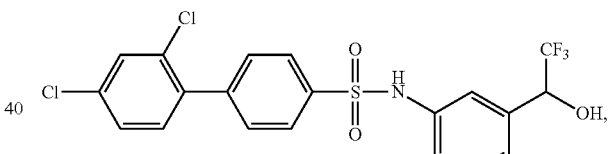
(ABD766)

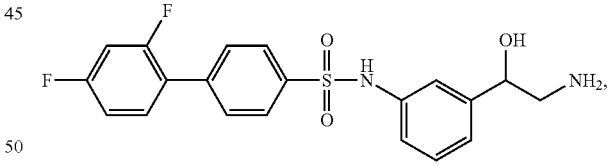
(ABD782)

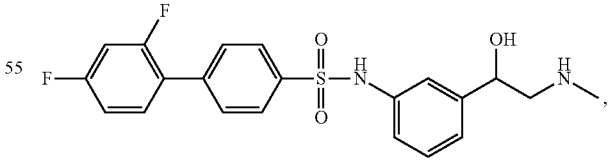
(ABD783)

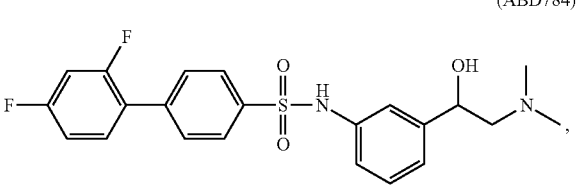
(ABD784)

-continued
(ABD785)
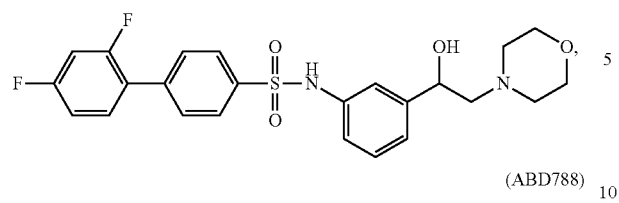
(ABD788)
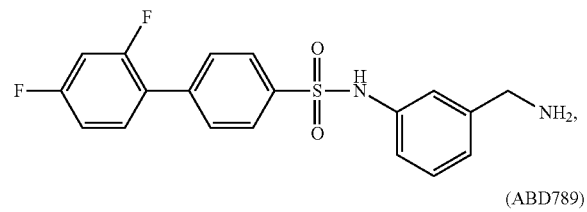
(ABD789)
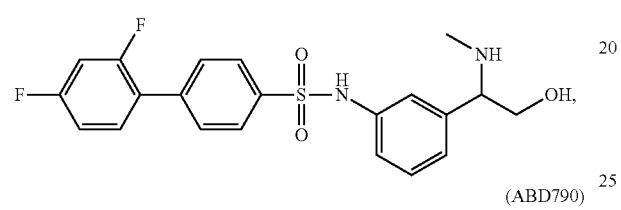
(ABD790)
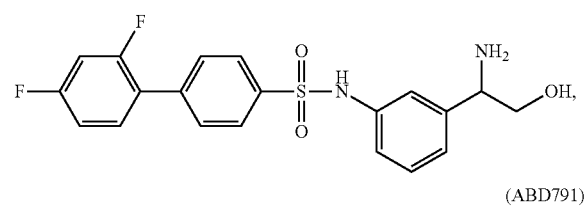
(ABD791)
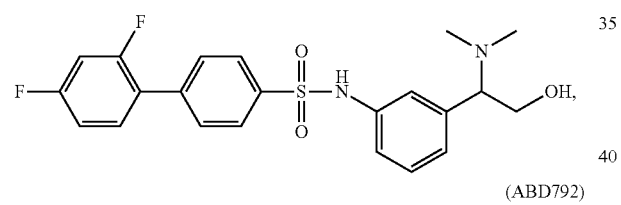
(ABD792)
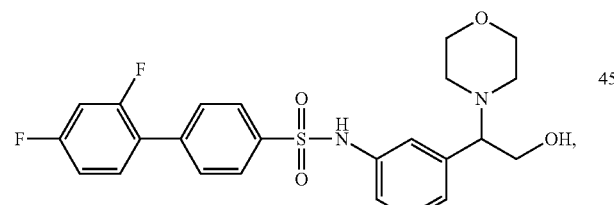
(ABD810)
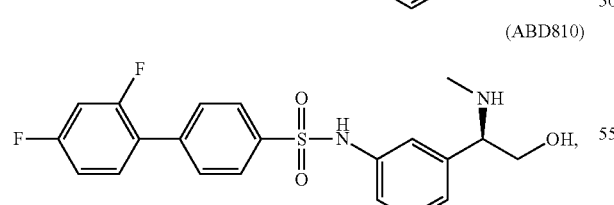
(ABD811)
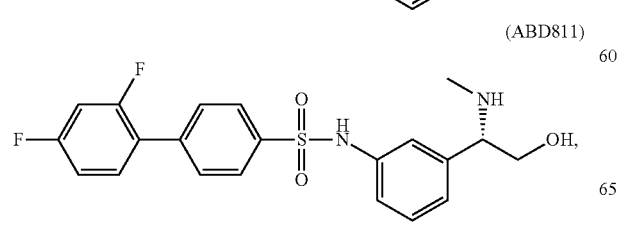
-continued
(ABD829)
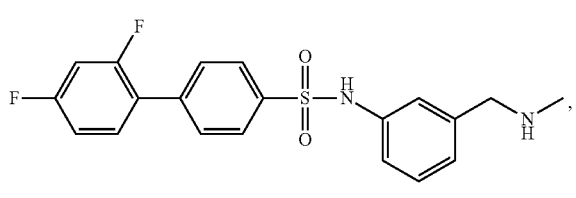
(ABD830)
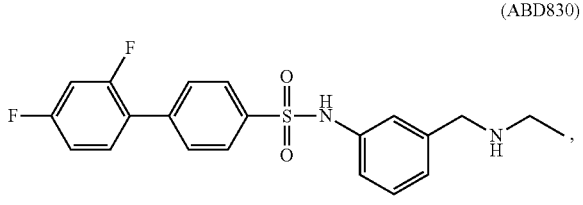
(ABD831)
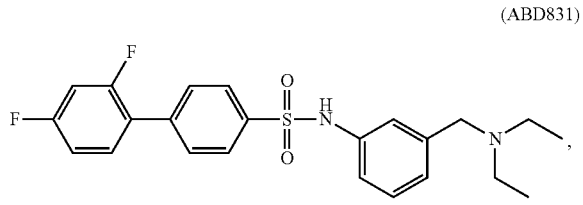
(ABD832)
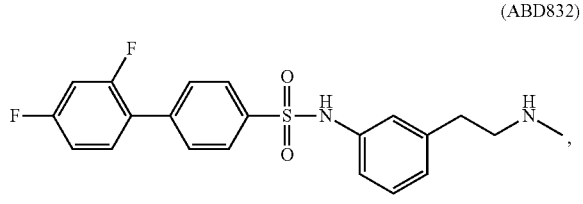
(ABD833)
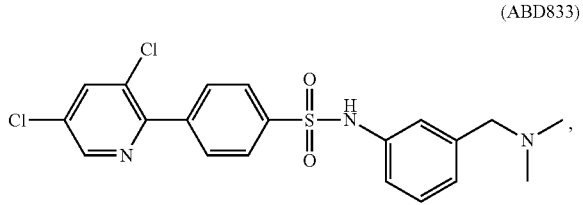
(ABD834)
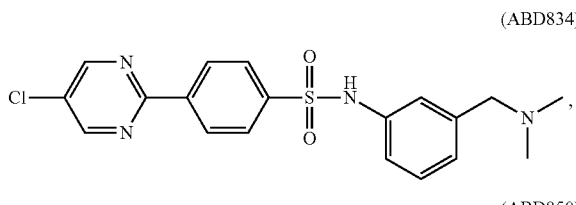
(ABD850)
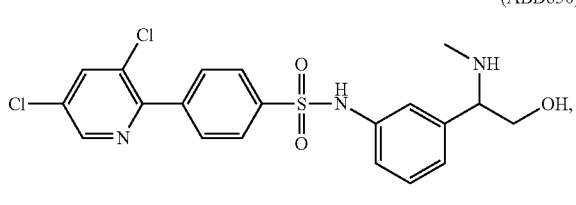
(ABD851)
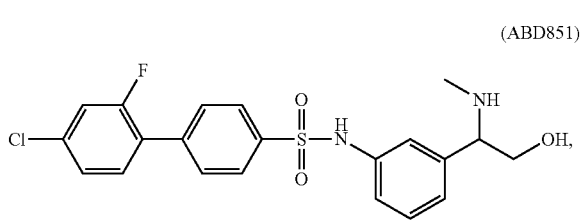

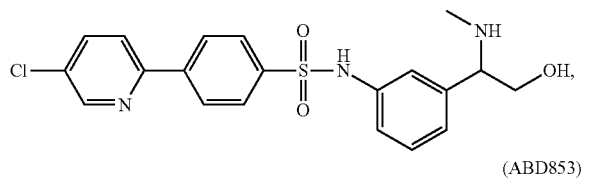
(ABD852)
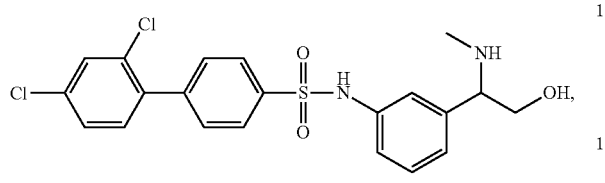
(ABD853)
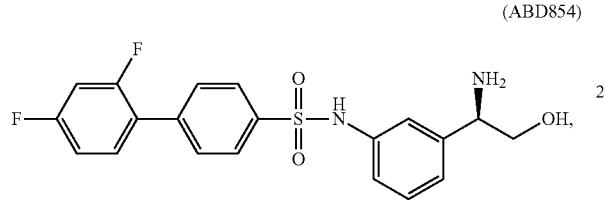
(ABD854)
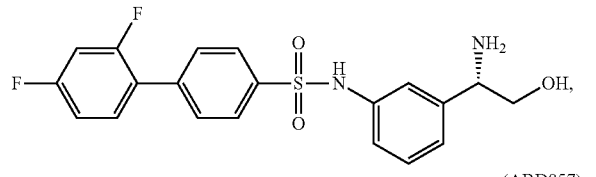
(ABD855)
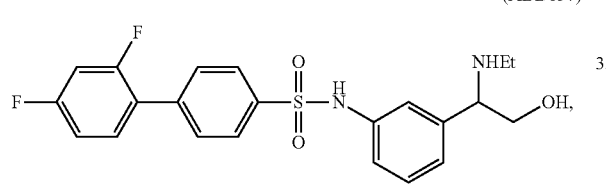
(ABD857)
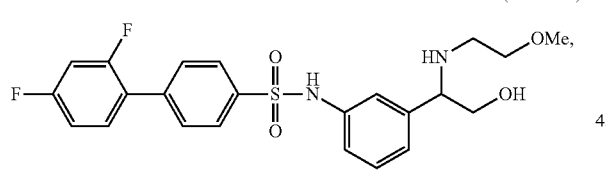
(ABD858)
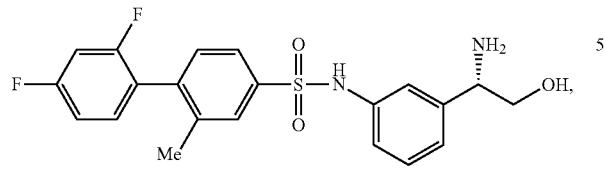
(ABD859)
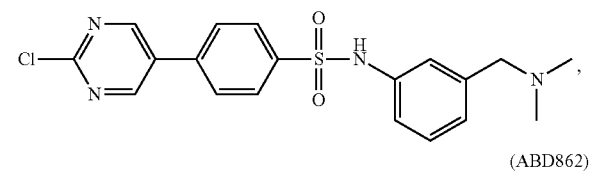
(ABD860)
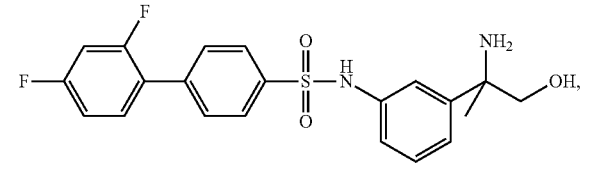
(ABD862)
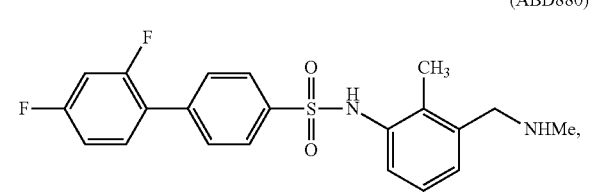
(ABD880)
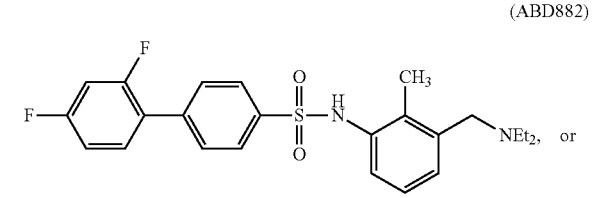
(ABD881)
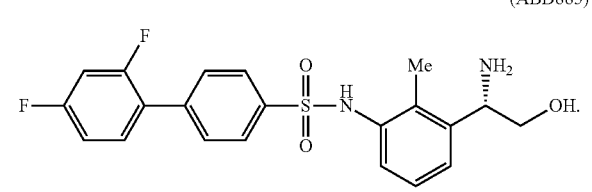
(ABD882)
22. A pharmaceutical composition comprising a compound according to claim 1 and a pharmaceutically acceptable carrier, diluent, or excipient.
* * * * *